US009453236B2

(12) United States Patent
Cahoon et al.

(10) Patent No.: US 9,453,236 B2
(45) Date of Patent: Sep. 27, 2016

(54) POLYNUCLEOTIDES AND POLYPEPTIDES INVOLVED IN POST-TRANSCRIPTIONAL GENE SILENCING

(71) Applicant: E I DU PONT DE NEMOURS AND COMPANY, Wilmington, DE (US)

(72) Inventors: Rebecca E. Cahoon, Lincoln, NE (US); Hajime Sakai, Newark, DE (US); J. Antoni Rafalski, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 75 days.

(21) Appl. No.: 14/284,623

(22) Filed: May 22, 2014

(65) Prior Publication Data

US 2014/0259217 A1   Sep. 11, 2014

Related U.S. Application Data

(60) Division of application No. 13/595,504, filed on Aug. 27, 2012, now Pat. No. 8,748,697, which is a division of application No. 13/208,396, filed on Aug. 12, 2011, now Pat. No. 8,278,431, which is a division of application No. 12/237,540, filed on Sep. 25, 2008, now Pat. No. 8,022,196, which is a continuation of application No. 11/093,888, filed on Mar. 30, 2005, now abandoned, which is a continuation of application No. 10/174,363, filed on Jun. 17, 2002, now abandoned.

(60) Provisional application No. 60/298,973, filed on Jun. 18, 2001.

(51) Int. Cl.
| | |
|---|---|
| *A01H 5/00* | (2006.01) |
| *A01H 5/10* | (2006.01) |
| *C12N 15/82* | (2006.01) |
| *C12N 15/113* | (2010.01) |
| *C07K 14/415* | (2006.01) |
| *C12Q 1/68* | (2006.01) |

(52) U.S. Cl.
CPC ......... *C12N 15/8218* (2013.01); *C07K 14/415* (2013.01); *C12Q 1/6895* (2013.01); *C12N 2799/026* (2013.01)

(58) Field of Classification Search
None
See application file for complete search history.

(56) References Cited

U.S. PATENT DOCUMENTS 8,022,196 B2   9/2011   Cahoon et al.

OTHER PUBLICATIONS

Rajagopalan et al (Genes & Development (2006) pp. 3407-3425).*
Bohmert et al (The EMBO Journal (1998) 17, 170-180).*
Guo et al (PNAS 2004 (101)25, 9205-9210).*
Nicoletta Romano et. al., Molecular Microbiology, vol. 6:3343-3353, 1992, Quelling: Transient Inactivation of Gene Expression in Neurospora Crassa by Transformation With Homologous Sequences.
Julia M. Bosher et. al., Nature Cell Biology, vol. 2:E31-36, 2000, RNA Interference: Genetic Wand and Genetic Watchdog.
Brenda L. Bass, Cell, vol. 101:235-238, 2000, Double-Stranded RNA as a Template for Gene Silencing.
Andrew J. Hamilton et. al., Science, vol. 286:950-952, 1999, A Species of Small Antisense RNA in Posttranscriptional Gene Silencing in Plants.
Philippe Mourrain et. al., Cell, vol. 101:533-542, 2000, *Arabidopsis* SGS2 and SGS3 Genes Are Required for Posttranscriptional Gene Silencing and Natural Virus Resistance.
Karen Bohmert et. al., The EMBO Journal, vol. 17:170-180, 1998, AGO1 Defines a Novel Locus of *Arabidopsis* Controlling Leaf Development.
Mathlide Fagard et. al., Proc. Natl. Acad. Sci., USA, vol. 97:11650-11654, 2000, AGO1, QDE-2, and RDE-1 are Related Proteins Required for Post-Transcriptional Gene Silencing in Plants, Quelling in Fungi, and RNA Interference in Animals.
Hiroaki Tabara et. al., Cell, vol. 99:123-132, 1999, The RDE-1 Gene, RNA Interference and Transposon Silencing in C. Elegans.
Bernard Moussian et. al., The EMBO Journal, vol. 17:1799-1809, 1998, Role of the Zwille Gene in the REgulation of Central Shoot Meristem Cell Fate During *Arabidopsis* Embryogenesis.
Karyn Lynn et. al., Development, vol. 126:469-481, 1999, The Pinhead/Zwille Gene Acts Pleiotrophically in *Arabidopsis* Development and has Overlapping Functions With the Argonaute1 Gene.
National Center for Biotechnology Information General Identifier No. 7248733, Apr. 28, 2000, Catalanotto, C. et al., Genes Silencing in Worms and Fungi.
National Center for Biotechnology Information General Identifier No.3885334, Apr. 5, 2000, Lin, X. et al., Sequence and Analysis of Chromosome 2 of the Plant *Arabidopsis thaliana*.
Lin, X. et A., Nature, vol. 402:761-768, 1999, Sequence and Analysis of Chromosome 2 of the Plant *Arabidopsis thaliana*.
National Center for Biotechnology Information General Identifier No. 6692120, Oct. 11, 2000, Walkerm M. et al., Genomic Sequence for Aradiposis thaliana BAC T19E23 From Chromosome 1.
National Center for Biotechnology Information General Identifier No. 11386626, Jun. 15, 2002, Bohmert, K., et al., AGO1 Defines a Novel Locus of Arabidopsis Controlling Leaf Development.
National Center for Biotechnology Information General Identifier No. 2149640, Jun. 2, 1998, Bohmert, K., et al., AGO1 Defines a Novel Locus of Arabidopsis Controlling Leaf Development.
National Center for Biotechnology Information General Identifier No. 5107374, Jun. 21, 1999, Lynn K. et al., The Pinhead/Zwille Gene Acts Pleiotrophically in Arabidopsis Development and has Overlapping Functions With the Argonaute1 Gene.
National Center for Biotechnology Information General Identifier No. 12643935, Jun. 15, 2002, Lynn K. et al., The Pinhead/Zwille Gene Acts Pleiotrophically in Arabidopsis Development and has Overlapping Functions With the Argonaute1 Gene.

(Continued)

*Primary Examiner* — Lee A Visone
(74) *Attorney, Agent, or Firm* — E I Du Pont De Nemours & Co.

(57) ABSTRACT

This invention relates to isolated nucleic acid fragments encoding polypeptides involved in post-transcriptional gene silencing. The invention also relates to construction of a recombinant DNA construct encoding all or a portion of the polypeptide involved in post-transcriptional gene silencing, in sense or antisense orientation, wherein expression of the recombinant DNA construct results in production of altered levels in a transformed host cell of the polypeptide involved in post-transcriptional gene silencing.

14 Claims, 9 Drawing Sheets

(56) References Cited

OTHER PUBLICATIONS

National Center for Biotechnology Information General Identifier No. 15221177, Jan. 10, 2002, Town, C.D, et al., Arabidopsis thaliana Chromosome 1 CHR1V12152001 Genomic Sequence.
C. Catalanotto et. al., Nature, vol. 404(6775):245, 2000, Gene Silencing in Worms and Fungi.
Hunter, et al., The *Arabidopsis* Heterochronic Gene Zippy Is an Argonaute Family Member, Current Biology, 2003, pp. 1734-1739, vol. 13.
Co-pendina U.S. Appl. No. 60/298,973, filed Jun. 18, 2001.
Co-pending U.S. Appl. No. 10/174,363, filed Jun. 1&, 2002.
Non-Final Office Action in U.S. Appl. No. 10/174,363 mailed Sep. 30, 2004.
Notice of Abandonment in U.S. Appl. No. 10/174,363 mailed Jun. 29, 2005.
Co-pending U.S. Appl. No. 11/093,888, filed Mar. 30, 2005.
Restriction Requirement in U.S. Appl. No. 11/093,888, dated Jun. 27, 2007.
Non-Final Office Action in U.S. Appl. No. 11/093,888, dated Sep. 21, 2007.
Final Office Action in U.S. Appl. No. 11/093,888, dated May 22, 2008.
Advisory Action in U.S. Appl. No. 11/093,888, dated Aug. 15, 2008.
Notice of Abandonment in U.S. Appl. No. 11/093,888, dated Dec. 19, 2008.
Co-pendina U.S. Appl. No. 12/237,540, filed Sep. 25, 2008.
Restriction Requirement in U.S. Appl. No. 12/237,540, dated May 3, 2010.
Non-Final Office Action in U.S. Appl. No. 12/237,540, dated Oct. 28, 2010.
Notice of Allowance in U.S. Appl. No. 12/237,540, dated May 16, 2011.
Notice of Allowability in U.S. Appl. No. 12/237,540, dated Jul. 19, 2011.
Corrected Notice of Allowability in U.S. Appl. No. 12/237,540, dated Jul. 21, 2011.
Co-pending U.S. Appl. No. 13/208,396, filed Aug. 12, 2011.
Restriction Requirement in U.S. Appl. No. 13/208,396, dated Feb. 16, 2012.
Notice of Allowance in U.S. Appl. No. 13/208,396, dated May 25, 2012.
Singh, Manjit, et al., "Production of Viable Gametes without Meiosis in Maize Deficient for an Argonaute Protein"; The Plant Cell, vol. 23, pp. 443-458, Feb. 2011.
Vaucheret et al., The Action of ARGONAUTE1 in the MIRNA Pathway and Its Regulation by the MIRNA Pathway are Crucial for Plant Development, Genes and Dev., 2004, pp. 1187-1197, vol. 18.
GENEBANK Accession No. CG032859, 2003.

* cited by examiner

FIG. 1A

```
              *  *                *******             *              *    **  **    *
SEQ ID NO:08  MES----HNGEANDLPPPPLIA-GVEPLKADETK--------MPLKP--------RSL
SEQ ID NO:22  MGS----HDGEDEELPPPPVPP-DVIPIKAEDAVGESPANHIL------KPKRLL
SEQ ID NO:40  MDSFEPDGNGKESLPPPPVVPSDIVPLKAEE--------VLCTPTEHNKK--KASRLP
SEQ ID NO:42  MES---HG---EDLPPPPLPP-NAEPIKAESADDLPPPPLLPIKPEEAKKISKPKRAL
SEQ ID NO:55  MES----NSGEIEELPPPPLPP-NAEPIKTD-----------DTKKLSKPKRAL
              1                                                        60

*  *      *     ***    ******    *  ***    **  **    *** *
SEQ ID NO:08  VQRNGFGRKGQPIKLITNHFKVSLVNAEFFYHYYVNLKYEDDTPVDRKGSGRKVIEKLQ
SEQ ID NO:22  MDRPGIGRKGQPTQLYSNHFKVAVKSTEDVFFHYVNLKYEDDRPVDGKIGRKVIDKLQ
SEQ ID NO:40  IARSGLGSKGNKIQLLTNHFKVNAKNDGHFFHYSVAFTYEDGRPVEGKGVGRKIIDRVQ
SEQ ID NO:42  IARPGFGKRGNPIQLVTNHFKVSLKTTDEFFHHYYVNLKYEDDRPVDGKGVGRKVIDKLA
SEQ ID NO:55  MARSGCGKKGQPIQLLTNHFKVSLKAADEFFHHYYVNLKYEDDRPVDGKGIGRKVLDKLQ
              61                                                       120

**                *    ***    ***********     *    *    *
SEQ ID NO:08  QTYAAELANKDFAYDGEKSLFTIGALPQVKNEFTVVEDFSTGKTPANGSPGNDSPPGS-
SEQ ID NO:22  QTYRAELSNKDFAYDGEKSLFTVGGLPQKKNEFTVVLEDVSTGKTAANGSPGGNDSPGGG
SEQ ID NO:40  ETYHSDLNGKDFAYDGEKSLFTVGSLPQNKLEFEVVLEFVVLEDVTSNRNNGNCSPDGLGD-NES
SEQ ID NO:42  QTYPSELAHKDFAYDGEKSLFTIGALPQINNEFVVVLEDVSSGKTPANG-SPGNDSP----
SEQ ID NO:55  QTYASELANKDFAYDGEKSLFTIGALPQVNNEFTVVLEDFNTGKSSANGGSPGNDSPGN-
              121                                                      180

**     *    ***  ***   *  *  **   *  *********
SEQ ID NO:08  DRKVRVRRPYNTKTYKVELSFAAKIPMSAISQALRGQESEHTQEAIRVIDIILRQHSAKQG
SEQ ID NO:22  DRKVRVRRPYQTKTFKVEINFAAEVPMSAIGQVIRGEESENSLEAIRVLDIILRQHSAEQG
SEQ ID NO:40  DRKRMRRPYRSKSFKVEISFAAKIPMSAIPMQAIASALRGQETENFQEAIRVLDIILRQHAAKQG
SEQ ID NO:42  DKKRVKRPYQTKTFKVELSFAARIPMSAIAMALKGQESEHTQEAIRVIDIILRQHSAKQG
SEQ ID NO:55  DRKRVRRPYQTKTFKVELNFAAKIPMSAIAQALRGQESENTQEAIRVIDIILRQHSAKQG
              181                                                      240
```

FIG. 1B

```
                   ****  ****  ***  * **** *************** ********   ****
SEQ ID NO:08       CLLVRQSFFHNNPSNFVDLGGGVVGCRGFHSSFRATQSGLSLNIDVSTTMIVKPGPVIDF
SEQ ID NO:22       CLLVKQSFFYNNPSCFVDLGGGVMGCRGFHSSFRGTQSGLSLNVDVSTTMIVKPGPVIDF
SEQ ID NO:40       CLLVRQSFFHNNPNFADVGGGVLGCRGFHSSFRTTQSGLSLNIDVSTTMIISPGPVVDF
SEQ ID NO:42       CLLVRQSFFHNNPSNFVDLGGGVMGCRGFHSSFRATQSGLSLNIDVSTTMIVKPGPVVDF
SEQ ID NO:55       CLLVRQSFFHNNPSNFVDLGGGVMGCRGFHSSFRATQSGLSLNIDVSTTMIVKPGPVVDF
                                                                               300
                   *       **     *     **   **  **  **    **  *****  *
SEQ ID NO:08       LLDNQKVGDSSMIDWAKGKRALKNLRIKISPANQEQKIVGLSERTCREQLFTLKHKNGNN
SEQ ID NO:22       LLSNQNVNDPSRIDWQKAKRALKGLRIRTTPANSEFKIFGLSERICKEQTFPLRQRNGSN
SEQ ID NO:40       LISNQNVRDPFQLDWAKAKARTLKNLRIKTSPSNQEFKISGLSELPCREQTFTLKGKGGGD
SEQ ID NO:42       LLANQKVDHPNKIDWAKAKRALKNLRIKTSPANTEYKIVGLSERNCYEQMFSLKQRNGGN
SEQ ID NO:55       LLANQKVDHPNKIDWAKAKRALKNLRIKTSPANTEYKIVGLSERNCYEQMFTLKQRNG-D
                                                                               360
                   *       **         **      **   ****  **  *******  *******
SEQ ID NO:08       GDSE--EITVYDYFVKQRGIVLQYSGDLPCINVGKLKRPTYFPIELCSLVPLQRYTKALN
SEQ ID NO:22       GDCDTIEITVYDYYAK-KGIDLKYSGDFPCINTGKAKRPTYFPIELCSLVPLQRYTKALS
SEQ ID NO:40       GEDGNEEITVYDYFVVRKIDLRYSADLPCINVGKPKRPTFFPIEVCELVSLQRYTKALS
SEQ ID NO:42       GDPEAIEISVYDYFVKNRGIELRYSGDFPCINVGKPKRPRRPTYFPIELCQLVPLQRYTKSLS
SEQ ID NO:55       GEPEGVEVSVYEYFVKNRGIELRYSGDFPCINVGKPKRPTYFPIELCSLVPLQRYTKALS
                                                                               420
                   ***  ************       *  **          *    **
SEQ ID NO:08       TLQRSSLVEKSRQKPQERMSVLSDVLQRSNYDAEPMLKACGITTARNFTEVDGRVLQPPK
SEQ ID NO:22       TLQRSSLVEKSRQKPEERMITVLNDALQRSNYDSDPMLRACGVSVAPKFTQVEGRILQAPK
SEQ ID NO:40       TLQRASLVEKSRQKPQERMKILSDALRTSNYGAEPMLRNCGISISTGFTEVEGRVLPAPR
SEQ ID NO:42       TLQRSSLVEKSRQKPQERMSVLSDVLKRSSYDTEPMLKACGISIAQGFTQVAGRVLQAPK
SEQ ID NO:55       TLQRSSLVEKSRQKPEERMSVLSDVLKRSNYDSEPMLNSCGISIARGFTQVAGRVLQAPK
                                                                               480
```

FIG. 1C

```
                 *** * ****  *  ******                          *** * ******                                 ***  *           ***
SEQ ID NO:08     LKAGNGEDIFTRNGRWNFNNKRLIRACSVEKWAVVNFSARCNVRDLVRDLIKCGGMKGIM
SEQ ID NO:22     LKAGNGDDIFSRNGRWNFTNRKFYETCSVNKWAVVNFSARCDVRNLIRDLMRNASAKGIQ
SEQ ID NO:40     LKFGNGEDLNPRNGRWMNVSRVKFVEPSKIERWAVANFSARCDVRGLVRDLIVNDLIKCGGMKGIT
SEQ ID NO:42     LKFGNGEDIFTRNGRWNFNNKRLARACVVDRWAVVNFSARCNTMNLIKCGGMKGIT
SEQ ID NO:55     LKAGNGEDLFARNGRWNFNNKRLIKASSIEKWAVVNFSARCNIRDLVRDIIKCGGMKGIK
                 481                                                              540

*          **   *             *  ** *    ***      *   *****  *
SEQ ID NO:08     VDAPFAVFDENPSMRRSPAIRRVEDMFEQVKTKLPGAPKFLLCVLAERKNSDIYGPWKKK
SEQ ID NO:22     MEEPFDVFEESPSMRRAPVSRRVDDMFGQIKSKLPGAPRFLLCLLPERKNCEIYGPWKRK
SEQ ID NO:40     IEQPFDVFDENPQFRRAPPMVREKMFEHIQSKLPGAPQFLLCLLPDRKNCDIYGPWKKK
SEQ ID NO:42     VEKPHIVIEENGSMRRAPAPKRVEDMFEQVKSKLPGAPKFLLCILAERKNSDVYGPWKRK
SEQ ID NO:55     VEDPFDVIEEDPSMRRAPAARRVDGMIDKMQKKLPGQPKFLLCVLAERKNSDIYGPWKRK
                 541                                                              600

* ***          ***  **                     ** ******* *   ***
SEQ ID NO:08     CLAEFGIVTQCVAPTRVNDQYLTNVLLKINAKLGGMNSLLQIETSPAIPLVSKVPTIILG
SEQ ID NO:22     CLAEFGIVTQCLAPLRVNDPYLLNLLMKINAKLGGLNSLLQVEASSSIPHVSQVPTILLG
SEQ ID NO:40     NLADFGIINQCMCPLRVNDQYLTNVMLKINAKLGGLNSLLQIEMSPSIPVVSKAPTLILG
SEQ ID NO:42     CLADFGIVTQCVAPTRVNDQYLTNVLLKINAKLGGMNSLLQIEMSPSIPLVSKVPTLILG
SEQ ID NO:55     CLAEFGIITQCVAPTRVNDQYITNVLLKINAKLGGLNSLLQIETSPSIPLVSKVPTIILG
                 601                                                              660

***********   *          *       *           *   *
SEQ ID NO:08     MDVSHGSPGHSDVPSIAAVVSSREWPLISKYRASVRTQSPKMEMIDSLFKPREA-EDDGL
SEQ ID NO:22     MDVSHGHPGQ-DRPSVAAVVSSRQWPLISRYRASVHTQSARLEMMSSLFKPRGT-DDDGL
SEQ ID NO:40     MDVSHGSPGQTDIPSIAAVVSSRHWPLISKYRACVRTQSAKMEMIDNLFKLVSEKEDEGI
SEQ ID NO:42     MDVSHGSPGQSDIPSIAAVVGSREWPLVSKYRASVRSQSPKLEMIDSLFKPQGT-DDDGL
SEQ ID NO:55     MDVSHGSPGQSDIPSIAAVVSSREWPLVSKYRASVRSQSPKLEMIDGLFKPQGAQEDDGL
                 661                                                              720
```

FIG. 1D

```
SEQ ID NO:08   **  *   ***  *  ************* *  **** *  ****  ***********  *   ***
SEQ ID NO:22   IRECLIDFYTSSGKRKPDQVIIFRDGVSESQFNQVLNIELQQIIEACKFLDEKWNPKFTL
SEQ ID NO:40   IRESLIDFHTSSGKRKPEHIIFRDGVSESQFTQVININIELDQIIEACKFLDEKWSPKFTV
SEQ ID NO:42   IRELLLDFYTTSGRRKPENIIFRDGVSESQFNQVLNIELDRIIEACKFLDENWEPKFVV
SEQ ID NO:55   VRECLIDFYTSSGKRKPDQIIFRDGVSESQFNQVLNIELDQIIEACKFLDENWNPKFTL
               IRELLVDFYTSTGKRKPDQVIIFRDGVSESQFTQVLNIELDQIIEACKFLDENWSPKFTL
                                                                        780

SEQ ID NO:08   * ******** ***    ***    ** **  ************ *******  *******
SEQ ID NO:22   IIAQKNHHTKFFIPGKPDNVPPGTVVDNKVCHPKNFDFYMCAHAGMIGTTRPTHYHILHD
SEQ ID NO:40   IVAQKNHHTKFFFQTASPDNVLPGTVVDSKVCHPKNFDFYMCAHAGMIGTTRPTHYHVLHD
SEQ ID NO:42   IVAQKNHHTRFFQPGSPDNVPPGTVIDNKICHPRNYDFYLCAHAGMIGTSRPTHYHVLLD
SEQ ID NO:55   IVAQKNHHTKFFIPGSPDNVPPGTVVDNAVCHPRNYDFYMCAHAGMIGTTRPTHYHILHD
               IVAQKNHHTKFFVPGSQNNVPPGTVVDNAVCHPRNNDFYMCAHAGMIGTTRPTHYHILHD
                                                                        840

SEQ ID NO:08   *   *    *    ***********  ***  *********      * *   ***   *
SEQ ID NO:22   EIGFSPDDLQELVHSLSYVYQRSTTAISVVAPICYAHLAAAQVGQFIKFDEMSETSSSHG
SEQ ID NO:40   EIGFSADEMQEFVHSLSYVYQRSTTAISVVAPVCYAHLAAAQVSTFLRLEEMSDASSSQG
SEQ ID NO:42   QVGFSPDQLQELVHSLSYVYQRSTTAISVVAPICYAHLAATQLGQFMKFEDKSETSSSHG
SEQ ID NO:55   EIHFAADDLQDLIVHSLSYVVSPICYAHLAAAQVAQFIKFDEMSETSSSQG
               EIGFSADDLQELVHSLSYVYQRSTTAISVVAPICYAHLAAAQVSQFIKFDEMSETSSSHG
                                                                        900

SEQ ID NO:08   **  *       *  **   ****
SEQ ID NO:22   G-HTSAGSVPVQELPRLHEKVRSSMFFC
SEQ ID NO:40   GGHTSAGSAPVPELPRLHDKVRSSMFFC
SEQ ID NO:42   G-LSGASAVPVPQLPPLQENVRNTMFFC
SEQ ID NO:55   GGHTSAGSAPVQELPRLHEKVRSSMFFC
               G-HTSAGSAPVPELPRLHNKVRSSMFFC
                                        928
```

FIG. 2A

```
                       *  **                    *                  * ***                  *  ***               *      *  *
SEQ ID NO:12    MVRKKRTGPGGSGETSG--ESSGASGQGSSQQPERTQQPGGRGWVP---------QQGHGG
SEQ ID NO:14    MVRKKRTGPGGSGETSG--ESSGASGQGSSQRPERTQQPGAGRGWVP---------QQGGRGG
SEQ ID NO:28    MMRKKKTEPRNAGESSGTQQATGAPGRGPSQRPERAQHGGG-GWQPANPQYAQQAGRGG
SEQ ID NO:38    MVRKRRTELIPSGGESSEAQRPAER--SAPPQQQAAAAAPGGA----------GPQGGRGW
SEQ ID NO:56    MVRKRRTDAPSEGGEGGSGSREAGPVSGGGRGSQRGGFQQGGG----------QHQGGRGY
                1                                                            60

***  **                    **  ***      ** ***         ****  ******
SEQ ID NO:12    GQHQGRDRHYQGRGGPGPHHLGSGAPEY-HPREYQGRGGEYQGHGGEYQGRGGDYQGRGG
SEQ ID NO:14    GQHQGRGGHYQGRGGPGPHHPG-GLPEY-HQREYQGRGGEYQGG---------YQGRGG
SEQ ID NO:28    GQHQGRGGRYQGRGGPTSHQPGGGPVEY-QAHEYYGRGVQ-------------
SEQ ID NO:38    GPQGGRGG-Y--GGGRSRGMP---QQQYGAPPEYQGRGRGGPSQQG---GRGG-Y---GG
SEQ ID NO:56    TPQPQQGG----RGGRGYGQPPQQQQQYGGPQEYQGRGRGGPHQG---GRGG-Y---GG
                61                                                           120

*  *****                                *            *
SEQ ID NO:12    GRSRGGMPQPYYGGHRGGNVGRNVPPGPSRTVPELHQAPYVQPAPVVSPSPGPGSSSQ
SEQ ID NO:14    ARSRGGISQPYYGGHRGGSVGRNVPPGPSRTVPELHQAPYVQYQAPVISPSPGPGSSSQ
SEQ ID NO:28    --RQGGMPQ------HRSGSGGHGVPASPSRTVPELHQASQDYQATVVAPSPSRTGPSSL
SEQ ID NO:38    GRSGGGM-------GSGRG--VGPSYGGPSRPPAPELHQATSVQFYQTGVSSQPALSEASS-
SEQ ID NO:56    GRGGG---------------PSSGPPQRQSVPELHQATSPTY--QAVSSQPTLSEVSP-
                121                                                          180

*                       *           **    *      * ******
SEQ ID NO:12    PMAEVSSGQVQQQFQQLADRGQSSTSQEIQVAPASSKSVRFPLRPGKGTYGDRCIVKANH
SEQ ID NO:14    PMAEVSSGQVQQQFEQLAIHGQSSMSQEVQVAPASSKSVRFPLRPGKGTYGDRCIVKANH
SEQ ID NO:28    PV-EASSEEVQHQFQELAIQGQSPTSQAIQPAPPSSKSVRFPMRPGKGTFGDRCIVKANH
SEQ ID NO:38    SLPPPEPVDLEQSMAQMVLH-SEAAPS---PPPASKSSMRFPLRPGKGSYGTKCVVKANH
SEQ ID NO:56    T-QVPEPTVLAQQFEQLSVE-QGAPSQAIQPIPSSSKAFKFPMRPGKGQSGKRCIVKANH
                181                                                          240
```

FIG. 2B

```
                  *******  ****  ******  ****  *****  *   ***  *****  ***   ********** **********
SEQ ID NO:12      FFAELPDKDLHQYDVSITPEVTSRGVNRAVMGELVTIYRQSHLGGRLPAYDGRKSLYTAG
SEQ ID NO:14      FFAELPDKDLHQYDVTITPEVTSRGVNRAVMGELVTLYRQSHLGGRLPAYDGRKSLYTAG
SEQ ID NO:28      FFAELPDKDLHQYDVSITPEVPSRGVNRAVIGEIVTQYRQSHLGGRLPVYDGRKSLYTAG
SEQ ID NO:38      FFAELPNKDLHQYDVTITPEVTSRGVNRAVMEQIVRLYRESHLGKRLPAYDGRKSLYTAG
SEQ ID NO:56      FFAELPDKDLHHYDVTITPEVTSRGVNRAVMKQLVDNYRDSHLGSRLPAYDGRKSLYTAG
                                                                               300
                  ******  *  *        ** ** *  **  *  * ****  ********* ** *** ***
SEQ ID NO:12      PLPFTSMAFEITLQDEEDSLGGRQGGHRRERVFRVVIKFAARADLHHLAMFLAGRQADAP
SEQ ID NO:14      PLPFTSMTFEITLQDEEDSVGGGQGGQRRERVFRVVIKFAARADLHHLAMFLAGRQADAP
SEQ ID NO:28      PLPFTSRTFDVILQDEEESLAVGQGAQRRERPFKVVIKFAARADLHHLAMFLAGRQADAP
SEQ ID NO:38      PLPFMSKEFRIVLADDD----EGAGGQRRDREFKVVIKLAARADLHHLGLFLQGRQTDAP
SEQ ID NO:56      PLPFNSKEFRINLLDEE----VGAGGQRREREFKVVIKLVARADLHHLGMFLEGKQSDAP
                                                                               360
                  ***** *******  **  **  *  ************* * ********* **********
SEQ ID NO:12      QEALQVLDIVLRELPTARYSPVGRSFYSPNLGRRQKLGEGLESWRGFYQSIRPTQMGLSL
SEQ ID NO:14      QEALQVLDIVLRELPTARYSPVGRSFYSPNLGRRQQLGEGLESWRGFYQSIRPTQMGLSL
SEQ ID NO:28      QEALQVLDIVLRELPTARYSPVARSFYSPNLGRRQQLGEGLESWRGFYQSIRPTQMGLSL
SEQ ID NO:38      QEALQVLDIVLRELPTTRYCPVGRSFYSPDLGRRQPLGEGLESWRGFYQSIRPTQMGLSL
SEQ ID NO:56      QEALQVLDIVLRELPTSRYIPVGRSFYSPDIGKKQSLGDGLESWRGFYQSIRPTQMGLSL
                                                                               420
                  ************ ***  **  *   ******* *** *********************
SEQ ID NO:12      NIDMSSTAFIEPLPVIDFVAQLLNRDISVRPLSDSDRVKIKKALRGVKVEVTHRGNMRRK
SEQ ID NO:14      NIDMSSTAFIEPLPVIDFVAQLLNRDISVRPLSDSDRVKIKKALRGVKVEVTHRGNMRRK
SEQ ID NO:28      NIDMSSTAFIEPLPVIDFVQLLNRDISVRPLSDADRVKIKKALRGVKVEVTHRGNMRRK
SEQ ID NO:38      NIDMSSTAFIEPLPVIDFVNQLLNRDVSARPLSDADRVKIKKALRGIKVEVTHRGNMRRK
SEQ ID NO:56      NIDMSSTAFIEANPVIQFVCDLLNRDISSRPLSDADRVKIKKALRGVKVEVTHRGNMRRK
                                                                               480
```

FIG. 2C

```
              *******  ******    *     * ** ******  *  *********  ***********
SEQ ID NO:12  YRISGLTSQATRELSFPVDDRGTVKTVVQYFMETYGFSIQHTTLPCLQVGNQQRPNYLPM
SEQ ID NO:14  YRISGLTSQATRELSFPVDDRGTVKTVVQYFMETYGFSIQHTTLPCLQVGNQQRPNYLPM
SEQ ID NO:28  YRISGLTSQATRELSFPIDNHGTVKTVVQYFQETYGFNIKHTTLPCLQVGNQQRPNYLPM
SEQ ID NO:38  YRISGLTSQATRELTFPVDERGTMKSVVEYFYETYGFVIQHTQWPCLQVGNTQRPNYLPM
SEQ ID NO:56  YRISGLTAVATRELTFPVDERNTQKSVVEYFHETYGFRIQHTQLPCLQVGNSNRPNYLPM
                                                                          540

**************                    * *********  ** ****
SEQ ID NO:12  EVCKIVEGQRYSKRLNEKQITALLKVTCQRPQERELDILQTVHHNAYYEDPYALEFGIRI
SEQ ID NO:14  EVCKIVEGQRYSKRLNEKXITALLKVTCQRPQERELDILQTVHHNAYYEDPYAQEFGIRI
SEQ ID NO:28  EVCKIVEGQRYSKRLNEKQITALLKVTCQRPQERELDILQTVHHNAYHQDPYAQEFGIRI
SEQ ID NO:38  EVCKIVEGQRYSKRLNERQITALLKVTCQRPVERERDIMQTVHHNAYHEDPYAKEFGIKI
SEQ ID NO:56  EVCKIVEGQRYSKRLNERQITALLKVTCQRPIDREKDILQTVQLNDYAKDNYAQEFGIKI
                                                                          600

*  *  ***** *  ***       *    *  *  ***  *  ******
SEQ ID NO:12  DERLAAVEARVLPPPRLKYHDSGREKDVLPRVGQWNMMNKKMVNGGRVSNWACINFSRNV
SEQ ID NO:14  DERLAAVEARVLPPPRLKYHDSGREKDVLPRVGQWNMMNKKMVNGGRVSNWACINFSRNV
SEQ ID NO:28  DERLASVEARVLPPPWLKYHDSGREKDVLPRIGQWNMMNKKMVNGGRVNNWTCINFSRHV
SEQ ID NO:38  SEKLAQVEARILPAPWLKYHDTGREKDCLPQVGQWNMMNKKMVNGGTVNNWFCINFSRNV
SEQ ID NO:56  STSLASVEARILPPPWLKYHESGREGTCLPQVGQWNMMNKKMINGGTVNNWICINFSRQV
                                                                          660

**   ***  ****  ***   **       *  ** ******   **  *******
SEQ ID NO:12  QDSAARGFSHELAVMCQISGMDFALEPVLPPVTARPEHVERALKARYQDAMNILRPQGRE
SEQ ID NO:14  QDSAARGFCHELAIMCQISGMDFSLEPVLPPVTARPEHVERALKARYQDAMNILRPQGRE
SEQ ID NO:28  QDNAARSFCRELAIMCQISGMDFSIDPVVPLVTARPEHVERALKARYQEAMNILKPQGGE
SEQ ID NO:38  QDSVARGFCYELAQMCYISGMAFTPEPVVPPVSARPDQVEKVLKTRYHDAKNKL--QGKE
SEQ ID NO:56  QDNLARTFCQELAQMCYVSGMAFNPEPVLPPVSARPEQVEKVLKTRYHDATSKL-SQGKE
                                                                          720
```

FIG. 2D

```
SEQ ID NO:12    LDLLIVILPDNNGSLYGDLKRICETELGLVSQCCLTKHVFKMSKQYLANVALKINVKVGG
SEQ ID NO:14    LDLLIVILPDINGSLYGDLKRICETDLGLVSQCCLTKHVFKMSKQYLANVALKINVKVGG
SEQ ID NO:28    LDLLIAILPDNNGSLYGDLKRICETDLGLVSQCCLTKHVFKMSKQYLANVALKINVKVGG
SEQ ID NO:38    LDLLIVILPDNNGSLYGDLKRICETDLGLVSQCCLTKHVFKMSKQYLANVALKINVKVGG
SEQ ID NO:56    IDLLIVILPDNNGSLYGDLKRICETELGLVSQCCLTKHVFKMSKQYMANVALKINVKVGG
                                                                      780

SEQ ID NO:12    RNTVLLDALSRRIPLVSDRPTIIFGADVTHPHPGEDSSPSIAAVVASQDWPEVTKYAGLV
SEQ ID NO:14    RNTVLVDALTRRIPLVSDRPTIIFGADVTHPHPGEDSSPSIAAVVASQDWPEVTKYAGLV
SEQ ID NO:28    RNTVLVDALTRRIPLVSDRPTIIFGADVTHPHPGEDSSPSIAAVVASQDWPEVTKYAGLV
SEQ ID NO:38    RNTVLVDALSRRIPLVSDRPTIIFGADVTHPHPGEDSSPSIAAVVASQDYPEITKYAGLV
SEQ ID NO:56    RNTVLVDALSRRIPLVSDRPTIIFGADVTHPHPGEDSSPSIAAVVASQDWPEITKYAGLV
                                                                      840

SEQ ID NO:12    SAQAHRQELIQDLFKVWQDPQRRTVTGGMIKELLISFKRATGQKPQRIIFYRDGVSEGQF
SEQ ID NO:14    SAQAHRQELIQDLFKVWQDPQRRTVTGGMIKELLISFKRATGQKPQRIIFYRDGVSEGQF
SEQ ID NO:28    SAQAHRQELIQDLFKVWQDPHRGTVTGGMIKELLISFKRATGQKPQRIIFYRDGVSEGQF
SEQ ID NO:38    CAQAHRQELIQDLFKVWQDPVRGTVTGGMIKELLISFRRATGQKPQRIIFYRDGVSEGQF
SEQ ID NO:56    CAQAHRQELIQDLFKEWKDPQKGVVTGGMIKELLIAFRRSTGHKPLRIIFYRDGVSEGQF
                                                                      900

SEQ ID NO:12    YQVLLYELDAIRKACASLEPNYQPPVTFVVVQKRHHTRLFANNHSDQRTVDRSGNILPGT
SEQ ID NO:14    YQVLLYELDAIRKACASLEPNYQPPVTFVVVQKRHHTRLFANNHSDQRTVDRSGNILPGT
SEQ ID NO:28    YQVLLYELDAIRKACASLEPNYQPPVTFVVVQKRHHTRLFANNHNDQRTVDRSGNILPGT
SEQ ID NO:38    YQVLLFELDAIRKACASLEPNYQPPVTFVVVQKRHHTRLFASNHHDKSSFDRSGNILPGT
SEQ ID NO:56    YQVLLYELDAIRKACASLEAGYQPPVTFVVVQKRHHTRLFAQNHNDRHSVDRSGNILPGT
                                                                      960
```

FIG. 2E

```
            ****************************************************** ***** ** ***************
SEQ ID NO:12   VVDSKICHPTEFDFYLCSHAGIQGTSRPAHYHVLWDENKFTADELQTLTNNLCYTYARCT
SEQ ID NO:14   VVDSKICHPTEFDFYLCSHAGIQGTSRPAHYHVLWDENKFTADELQTLTNNLCYTYARCT
SEQ ID NO:28   VVDSKICHPTEFDFYLCSHAGIQGTSRPAHYHVLWDENKFTADELQTLTNNLCYTYARCT
SEQ ID NO:38   VVDSKICHPTEFDFYLCSHAGIQGTSRPAHYHVLWDENNFTADALQTLTNNLCYTYARCT
SEQ ID NO:56   VVDSKICHPTEFDFYLCSHAGIQGTSRPAHYHVLWDENNFTADGLQSLTNNLCYTYARCT
             961                                                        1020

************************************************ ** **** *
SEQ ID NO:12   RSVSIVPPAYYAHLAAFRARFYMEPDTSDSGSLASGA---RGPPPG----AARSSTRGAG
SEQ ID NO:14   RSVSIVPPAYYAHLAAFRARFYMEPDTSDSGSMASGA---RGPPPG----AARS-MRGAG
SEQ ID NO:28   RSVSIVPPAYYAHLAAFRARFYMEPETSDSGSMASGAATSRGLPPG---V--RSARVAG
SEQ ID NO:38   RSVSIVPPAYYAHLAAFRARFYMEPETSDSGSMTSGAVAGRGMGGGGGVGRSTRAPGA
SEQ ID NO:56   RSVSIVPPAYYAHLAAFRARFYMEPETSDSGSMASGSMAR------GGGMAGRSTRGPNV
              1021                                                       1080

****************************
SEQ ID NO:12   SVEVRPLPALKENVKRVMFYC
SEQ ID NO:14   SVAVRPLPALKENVKRVMFYC
SEQ ID NO:28   NVAVRPLPALKENVKRVMFYC
SEQ ID NO:38   NAAVRPLPALKENVKRVMFYC
SEQ ID NO:56   NAAVRPLPALKENVKRVMFYC
              1081                1101
```

POLYNUCLEOTIDES AND POLYPEPTIDES INVOLVED IN POST-TRANSCRIPTIONAL GENE SILENCING

REFERENCE TO RELATED APPLICATIONS

This application is a divisional application of U.S. patent application Ser. No. 13/595,504, filed on Aug. 27, 2012, now U.S. Pat. No. 8,748,697, which is a divisional application of U.S. patent application Ser. No. 13/208,396, filed on Aug. 12, 2011, now U.S. Pat. No. 8,278,431, which is a divisional application of U.S. patent application Ser. No. 12/237,540, filed on Sep. 25, 2008, now U.S. Pat. No. 8,022,196, which is a continuation application of U.S. patent application Ser. No. 11/093,888, filed on Mar. 30, 2005, now abandoned, which is a continuation application of U.S. patent application Ser. No. 10/174,363, filed on Jun. 17, 2002, now abandoned, which claims the benefit of U.S. Provisional Application No. 60/298,973, filed Jun. 18, 2001, now expired, the entire contents of each of which are herein incorporated by reference.

REFERENCE TO SEQUENCE LISTING SUBMITTED ELECTRONICALLY

The official copy of the sequence listing is submitted electronically via EFS-Web as an ASCII formatted sequence listing with a file named 20140522_BB1454USDIV3_SequenceListing created on May 22, 2014 and having a size of 220 kilobytes and is filed concurrently with the specification. The sequence listing contained in this ASCII formatted document is part of the specification and is herein incorporated by reference in its entirety.

FIELD OF THE INVENTION

This invention is in the field of plant molecular biology. More specifically, this invention pertains to nucleic acid fragments encoding polypeptides in plants and seeds involved in post-transcriptional gene silencing.

BACKGROUND OF THE INVENTION

Post-transcriptional gene silencing (PTGS), which operates at the level of sequence-specific RNA degradation, has emerged as a major phenomenon through which transgene expression in plants is down-regulated. It was first recognized in plants, and similar mechanisms since then have been observed in non-plant systems, where it is known by different names, to wit, quelling in the fungus *Neurospora crassa* (Romano and Macino (1992) *Mol Microbiol* 6:3343-3353), and RNA interference (RNAi) in worms, flies, and mammals (Bosher and Labouesse (2000) *Nat Cell Biol* 2:E31-36).

Although the mechanism remains to be fully elucidated, it appears that double-stranded RNA (dsRNA) serve as key intermediates in PTGS (Bass (2000) *Cell* 101:235-238). The involvement of dsRNA is supported by identification of small complementary RNA (cRNA), 21-25 nucleotides long, which can bind the target RNA to form dsRNA, in PTG-silenced plants (Hamilton and Baulcombe (1999) *Science* 286:950-952), and the finding that a protein similar to RNA-dependent RNA polymerase, the enzyme involved in cRNA synthesis, is required for PTGS (Mourrain et al. (2000) *Cell* 101:533-542).

Another protein identified to be required for PTGS is the ARGONAUTE (AGO1) protein (Bohmert et al. (1998) *EMBO J* 17:170-180; Fagard et al. (2000) *Proc Natl Acad Sci USA* 97:11650-11654). AGO1 protein shares homology with the RDE1 and QDE-2 proteins which have been found to be required for RNAi in *C. elegans* and for quelling in *Neurospora*, respectively, thus reinforcing the notion that PTGS, RNAi, and quelling are similar processes at the mechanistic level. AGO1/RDE1/QDE-2 proteins are similar to eIF2C, a protein important for protein translation. It is therefore hypothesized that dsRNA mediates PTGS by disrupting proper positioning of eIF2C in the translation machinery complex, thereby preventing translation of the target mRNA (Tabara et al. (1999) *Cell* 99:123-132; Fagard et al. (2000) *Proc Natl Acad Sci USA* 97:11650-11654).

It is apparent that PTGS is an important process, which if manipulated properly, may be used to control transgene expression. Disclosed herein are sequences very homologous to the AGO1 protein family, which includes the ZWILLE (ZLL) or PINHEAD (PNH) protein involved in plant development (Moussian et al. (1998) *EMBO J* 17:1799-1809; Lynn et al. (1999) *Development* 126:469-481), and the RDE-1 protein involved in transposon silencing (Tabara et al. (1999) *Cell* 99:123-132). These sequences may be used to manipulate PTGS. Since some of the AGO1 family members have also been shown to be involved in transposon silencing, meristem development, and differentiation of meristematic tissue, the polynucleotides disclosed herein may also be used to manipulate transposon activity, meristem activity, plant architecture and development, and proliferation of undifferentiated plant cells in culture, which would be useful in callus propagation.

SUMMARY OF INVENTION

The present invention includes isolated polynucleotides comprising: (a) a first nucleotide sequence encoding a first polypeptide having post-transcriptional gene silencing activity wherein the amino acid sequence of the first polypeptide and the amino acid sequence of SEQ ID NO:12, 14, 22, 28, 40 or 54 have at least 80% sequence identity, or (b) a second nucleotide sequence encoding a second polypeptide having post-transcriptional gene silencing activity wherein the amino acid sequence of the second polypeptide and the amino acid sequence of SEQ ID NO:8, 38 or 42 have at least 85% sequence identity. For the first polypeptide, it is preferred that the identity be at least 85%, it is more preferred that the identity is at least 90%, and it is even more preferred that the identity be at least 95%. For the second polypeptide, it is preferred that the identity be at least 90%, and it is more preferred that the identity be at least 95%. More preferably, the present invention includes isolated polynucleotides encoding the amino acid sequence of SEQ ID NO:8, 12, 14, 22, 28, 38, 40, 42 or 54 or nucleotide sequences comprising the nucleotide sequence of SEQ ID NO:7, 11, 13, 21, 27, 37, 39, 41 or 53. The present invention also includes isolated polynucleotides comprising the complement of nucleotide sequences of the present invention.

The present invention also includes:

in a preferred first embodiment, an isolated polynucleotide comprising: (a) a first nucleotide sequence encoding a first polypeptide, wherein the amino acid sequence of the first polypeptide and the amino acid sequence of SEQ ID NO:12, 14, 22, 28, 40 or 54 have at least 80%, 85%, 90%, or 95% sequence identity, (b) a second nucleotide sequence encoding a second polypeptide, wherein the amino acid sequence of the second polypeptide and the amino acid sequence of SEQ ID SEQ ID NO:8, 38 or 42 have at least 85%, 90%, or 95% sequence identity, or (c) the complement of the nucleotide sequence of (a) or (b); the first polypeptide preferably comprises the amino acid sequence of SEQ ID NO:12, 14, 22, 28, 40 or 54; the second polypeptide preferably comprises the amino acid sequence of SEQ ID NO:8, 38 or 42; the first nucleotide sequence preferably comprises the nucleotide sequence of SEQ ID NO:11, 13, 21, 27, 39 or 53; the second nucleotide sequence preferably comprises the nucleotide sequence of SEQ ID NO:7, 37 or 41; the first and second polypeptides preferably have post-transcriptional gene silencing activity;

in a preferred second embodiment, a recombinant DNA construct comprising any of the isolated polynucleotides of the present invention operably linked to at least one regulatory sequence, and a cell, a plant, and a seed comprising the recombinant DNA construct;

in a preferred third embodiment, a vector comprising any of the isolated polynucleotides of the present invention;

in a preferred fourth embodiment, an isolated polynucleotide comprising a nucleotide sequence comprised by any of the polynucleotides of the first embodiment, wherein the nucleotide sequence contains at least 30, 40, or 60 nucleotides;

in a preferred fifth embodiment, a method for transforming a cell comprising transforming a cell with any of the isolated polynucleotides of the present invention, and the cell transformed by this method, advantageously, the cell is eukaryotic, e.g., a yeast or plant cell, or prokaryotic, e.g., a bacterium;

in a preferred sixth embodiment, a method for producing a transgenic plant comprising transforming a plant cell with any of the isolated polynucleotides of the present invention and regenerating a plant from the transformed plant cell, a transgenic plant produced by this method, and seed obtained from this transgenic plant;

in a preferred seventh embodiment, an isolated polypeptide comprising: (a) a first amino acid sequence, wherein the first amino acid sequence and the amino acid sequence of SEQ ID NO:12, 14, 22, 28, 40 or 54 have at least 80%, 85%, 90% or 95% sequence identity, or (b) a second amino acid sequence, wherein the second amino acid sequence and the amino acid sequence of SEQ ID NO:8, 38 or 42 have at least 85%, 90% or 95% sequence identity; the first amino acid sequence preferably comprises the amino acid sequence of SEQ ID NO:12, 14, 22, 28, 40 or 54, and the second amino acid sequence preferably comprises the amino acid sequence of SEQ ID NO:8, 38 or 42; the polypeptide preferably has post-transcriptional gene silencing activity;

in a preferred eight embodiment, a method for isolating a polypeptide encoded by polynucleotides of the present invention comprising isolating the polypeptide from cultivated cells, from the culture medium, or from both the cultivated cells and the culture medium, wherein the cells contain a recombinant DNA construct comprising the polynucleotide operably linked to at least one regulatory sequence;

in a preferred ninth embodiment, a virus, preferably a baculovirus, comprising any of the isolated polynucleotides of the present invention or any of the recombinant DNA constructs of the present invention;

in a preferred tenth embodiment, a method of selecting an isolated polynucleotide that affects the level of expression in a host cell, preferably a plant cell, of a gene encoding a polypeptide having post-transcriptional gene silencing activity, the method comprising the steps of: (a) constructing an isolated polynucleotide of the present invention or an isolated recombinant DNA construct of the present invention; (b) introducing the isolated polynucleotide or the isolated recombinant DNA construct into a host cell; (c) measuring the level of the polypeptide involved in post-transcriptional gene silencing or its activity in the host cell containing the isolated polynucleotide or the isolated recombinant DNA construct; and (d) comparing the level of the polypeptide involved in post-transcriptional gene silencing or its activity in the host cell containing the isolated polynucleotide or the isolated recombinant DNA construct with the level of the polypeptide involved in post-transcriptional gene silencing or its activity in the host cell that does not contain the isolated polynucleotide or the isolated recombinant DNA construct;

in a preferred eleventh embodiment, a method of obtaining a nucleic acid fragment encoding a substantial portion of a polypeptide involved in post-transcriptional gene silencing comprising the steps of: synthesizing an oligonucleotide primer comprising a nucleotide sequence of at least 30 (preferably at least 40, most preferably at least 60) contiguous nucleotides derived from a nucleotide sequence of SEQ ID NO:1, 3, 5, 7, 9, 11, 13, 15, 17, 19, 21, 23, 25, 27, 29, 31, 33, 35, 37, 39, 41, 43, 45, 47, 49, 51 or 53, or the complement of such nucleotide sequences; and amplifying a nucleic acid fragment (preferably a cDNA inserted in a cloning vector) using the oligonucleotide primer; the amplified nucleic acid fragment preferably will encode a substantial portion of a polypeptide involved in post-transcriptional gene silencing;

in a preferred twelfth embodiment, a method of obtaining a nucleic acid fragment encoding all or a substantial portion of the amino acid sequence encoding a polypeptide involved in post-transcriptional gene silencing comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone;

in a preferred thirteenth embodiment, a method for positive selection of a transformed cell comprising: (a) transforming a host cell with a recombinant DNA construct of the present invention or an expression cassette of the present invention; and (b) growing the transformed host cell, preferably a plant cell, such as a monocot or a dicot, under conditions which allow expression of the polypeptide involved in post-transcriptional gene silencing polynucleotide in an amount sufficient to complement a null mutant to provide a positive selection means; and in a preferred fourteenth embodiment, a method of altering the level of expression of a polypeptide involved in post-transcriptional gene silencing in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the polypeptide involved in post-transcriptional gene silencing in the transformed host cell.

BRIEF DESCRIPTION OF THE DRAWINGS AND SEQUENCE LISTING

The invention can be more fully understood from the following detailed description and the accompanying drawings and Sequence Listing which form a part of this application.

FIGS. 1A, 1B, 1C and 1D depict the amino acid sequence alignment of the polypeptides involved in post-transcriptional gene silencing encoded by the following: (a) nucleotide sequence derived from corn clone cle1f.pk002.k13 (SEQ ID NO:8), (b) nucleotide sequence derived from corn clone p0119.cmtmm21r (SEQ ID NO:22), (c) nucleotide sequence derived from soybean clone ssl1c.pk003.g3 (SEQ ID NO:40), (d) nucleotide sequence of a contig assembled from nucleotide sequences obtained from wheat clone wdk1c.pk012.i2 and PCR fragments (SEQ ID NO:42), and (e) nucleotide sequence from *Oryza sativa* (NCBI GenBank Identifier (GI) No. 6539559; SEQ ID NO:55). Amino acids which are conserved among all and at least two sequences with an amino acid at that position are indicated with an asterisk (*). Dashes are used by the program to maximize alignment of the sequences.

FIGS. 2A, 2B, 2C, 2D and 2E depict the amino acid sequence alignment of the polypeptides involved in post-transcriptional gene silencing encoded by the following: (a) nucleotide sequence derived from corn clone csc1c.pk006.j19 (SEQ ID NO:12), (b) nucleotide sequence derived from corn clone ctn1c.pk003.i20 (SEQ ID NO:14), (c) nucleotide sequence of a contig assembled from nucleotide sequences obtained from rice clone rlm1n.pk001.m11 and PCR fragments (SEQ ID NO:28), (d) nucleotide sequence of a contig assembled from nucleotide sequences obtained from soybean clone sdc2c.pk001.p4 and PCR fragments (SEQ ID NO: 38), and (e) nucleotide sequence from *Arabidopsis thaliana* (NCBI GenBank Identifier (GI) No. 2149640; SEQ ID NO:56). Amino acids which are conserved among all and at least two sequences with an amino acid at that position are indicated with an asterisk (*). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more EST, FIS or PCR sequences ("Contig"), or sequences encoding the entire protein, or functionally active polypeptide, derived from an EST, an FIS, or a contig ("CGS"). The sequence descriptions and Sequence Listing attached hereto comply with the rules governing nucleotide and/or amino acid sequence disclosures in patent applications as set forth in 37 C.F.R. §1.821-1.825.

TABLE 1

Polypeptides Involved in Post-Transcriptional Gene Silencing

| Polypeptide (Plant Source) | Clone Designation | Status | SEQ ID NO: (Nucleotide) | SEQ ID NO: (Amino Acid) |
|---|---|---|---|---|
| Zwille Homolog (Corn) | p0102.cerba57r | FIS | 1 | 2 |
| Zwille Homolog (Soybean) | ses2w.pk0009.g6 | FIS | 3 | 4 |
| Zwille Homolog (Soybean) | ssm.pk0063.a4 | FIS | 5 | 6 |
| Argonaute Homolog (Corn) | cle1f.pk002.k13 (FIS) | CGS | 7 | 8 |
| Argonaute Homolog (Corn) | cpf1c.pk008.j24 | FIS | 9 | 10 |
| Argonaute Homolog (Corn) | csc1c.pk006.j19 (FIS) | CGS | 11 | 12 |
| Argonaute Homolog (Corn) | ctn1c.pk003.i20 (FIS) | CGS | 13 | 14 |
| Argonaute Homolog (Corn) | Contig of p0002.cgevj06r p0125.czaab55r (FIS) p0125.czaat57r | contig | 15 | 16 |
| Argonaute Homolog (Corn) | p0102.cerae32ra | EST | 17 | 18 |
| Argonaute Homolog (Corn) | p0107.cbcbd69r | EST | 19 | 20 |
| Argonaute Homolog (Corn) | p0119.cmtmm21r (FIS) | CGS | 21 | 22 |
| Argonaute Homolog (Rice) | rca1n.pk018.b3 | FIS | 23 | 24 |
| Argonaute Homolog (Rice) | rl0n.pk124.g8 | FIS | 25 | 26 |
| Argonaute Homolog (Rice) | Contig of rlm1n.pk001.m11 (FIS) PCR fragment sequence | CGS | 27 | 28 |
| Argonaute Homolog (Rice) | rls6.pk0082.d4 | FIS | 29 | 30 |
| Argonaute Homolog (Rice) | rsl1n.pk004.d12 | FIS | 31 | 32 |
| Argonaute Homolog (Rice) | rtc1c.pk008.k19.f | EST | 33 | 34 |
| Argonaute Homolog (Soybean) | sdc1c.pk0004.d11 | FIS | 35 | 36 |
| Argonaute Homolog (Soybean) | Contig of sdc2c.pk001.p4 (FIS) PCR fragment sequence | CGS | 37 | 38 |
| Argonaute Homolog (Soybean) | ssl1c.pk003.g3 (FIS) | CGS | 39 | 40 |
| Argonaute Homolog (Wheat) | Contig of wdk1c.pk012.i2 (FIS) PCR fragment sequence | CGS | 41 | 42 |
| Argonaute Homolog (Wheat) | wlm96.pk029.c23 | FIS | 43 | 44 |
| Argonaute Homolog (Wheat) | wne1g.pk003.f8 | EST | 45 | 46 |
| Argonaute Homolog (Wheat) | wr1.pk0073.c7 | EST | 47 | 48 |
| Argonaute Homolog (Wheat) | wre1n.pk0001.h6 | FIS | 49 | 50 |
| Argonaute Homolog (Wheat) | wre1n.pk162.h10 | EST | 51 | 52 |
| Argonaute Homolog (Rice) | rdi2c.pk002.d14:fis | CGS | 53 | 54 |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

The problem to be solved, therefore, was to identify polynucleotides that encode polypeptides involved in post-transcriptional gene silencing. These polynucleotides may be used in plant cells to alter the post-transcriptional gene silencing pathway. More specifically, the polynucleotides of the instant invention may be used to create transgenic plants where the levels of polypeptides involved in post-transcriptional gene silencing are altered with respect to non-transgenic plants which would result in plants with an enhancement or a deficiency in post-transcriptional gene silencing. The present invention has solved this problem by providing polynucleotide and deduced polypeptide sequences corresponding to novel polypeptides involved in post-transcriptional gene silencing from corn (*Zea mays*), rice (*Oryza sativa*), soybean (*Glycine max*) and wheat (*Triticum aestivum*).

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NOs:1, 3, 5, 7, 9, 11, 13, 15, 17, 19, 21, 23, 25, 27, 29, 31, 33, 35, 37, 39, 41, 43, 45, 47, 49, 51 or 53, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises any of the isolated polynucleotides of the present invention operably linked to at least one regulatory sequence.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence of SEQ ID NOs:1, 3, 5, 7, 9, 11, 13, 15, 17, 19, 21, 23, 25, 27, 29, 31, 33, 35, 37, 39, 41, 43, 45, 47, 49, 51 or 53, and the complement of such nucleotide sequences may be used to affect the expression and/or function of a polypeptide involved in post-transcriptional gene silencing in a host cell. A method of using an isolated polynucleotide to affect the level of expression of a polypeptide in a host cell (eukaryotic, such as plant or yeast, prokaryotic such as bacterial) may comprise the steps of: constructing an isolated polynucleotide of the present invention or an isolated recombinant DNA construct of the present invention; introducing the isolated polynucleotide or the isolated recombinant DNA construct into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%. Sequence alignments and percent identity calculations were performed using the Megalign program of the LASERGENE bioinformatics computing suite (DNASTAR Inc., Madison, Wis.). Multiple alignment of the sequences was performed using the ClustalV method of alignment (Higgins and Sharp (1989) CABIOS. 5:151-153) with the default parameters (GAP PENALTY=10, GAP LENGTH PENALTY=10). Default parameters for pairwise alignments using the ClustalV method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403-410; see also the explanation of the BLAST algorithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, recombinant DNA constructs, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632). A "mitochondrial signal peptide" is an amino acid sequence which directs a precursor protein into the mitochondria (Zhang and Glaser (2002) *Trends Plant Sci* 7:14-21).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277; Ishida Y. et al. (1996) *Nature Biotech.* 14:745-750) and particle-accelerated or "gene gun" transformation technology (Klein et al. (1987) *Nature* (London) 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The term "transformation" as used herein refers to both stable transformation and transient transformation.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be used by itself or may be used in conjunction with a vector. If a vector is used, the choice of vector is dependent upon the method that will be used to transform host plants as is well known to those skilled in the art.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"Motifs" or "subsequences" refer to short regions of conserved sequences of nucleic acids or amino acids that comprise part of a longer sequence. For example, it is expected that such conserved subsequences would be important for function, and could be used to identify new homologues in plants. It is expected that some or all of the elements may be found in a homologue. Also, it is expected that one or two of the conserved amino acids in any given motif may differ in a true homologue.

"PCR" or "polymerase chain reaction" is well known by those skilled in the art as a technique used for the amplification of specific DNA segments (U.S. Pat. Nos. 4,683,195 and 4,800,159).

The present invention includes an isolated polynucleotide comprising: (a) a first nucleotide sequence encoding a first polypeptide comprising at least 100 amino acids, wherein the amino acid sequence of the first polypeptide and the amino acid sequence of SEQ ID NO:16, SEQ ID NO:18, SEQ ID NO:20, SEQ ID NO:30, SEQ ID NO:36, SEQ ID NO:44, SEQ ID NO:48, or SEQ ID NO:52 have at least 70%, 80%, 85%, 90%, or 95% identity based on the ClustalV alignment method, (b) a second nucleotide sequence encoding a second polypeptide comprising at least 200 amino acids, wherein the amino acid sequence of the second polypeptide and the amino acid sequence of SEQ ID NO:24 have at least 70%, 80%, 85%, 90%, or 95% identity based on the ClustalV alignment method, (c) a third nucleotide sequence encoding a third polypeptide comprising at least 100 amino acids, wherein the amino acid sequence of the third polypeptide and the amino acid sequence of SEQ ID NO:34 have at least 80%, 85%, 90%, or 95% identity based on the ClustalV alignment method, (d) a fourth nucleotide sequence encoding a fourth polypeptide comprising at least 150 amino acids, wherein the amino acid sequence of the fourth polypeptide and the amino acid sequence of SEQ ID NO:10 have at least 80%, 85%, 90%, or 95% identity based on the ClustalV alignment method, (e) a fifth nucleotide sequence encoding a fifth polypeptide comprising at least 200 amino acids, wherein the amino acid sequence of the fifth polypeptide and the amino acid sequence of SEQ ID NO:2, SEQ ID NO:6, SEQ ID NO:22, or SEQ ID NO:50 have at least 80%, 85%, 90%, or 95% identity based on the ClustalV alignment method, (f) a sixth nucleotide sequence encoding a sixth polypeptide comprising at least 300 amino acids, wherein the amino acid sequence of the sixth polypeptide and the amino acid sequence of SEQ ID NO:28, SEQ ID NO:40 or SEQ ID NO:54 have at least 80%, 85%, 90%, or 95% identity based on the ClustalV alignment method, (g) a seventh nucleotide sequence encoding a seventh polypeptide comprising at least 100 amino acids, wherein the amino acid sequence of the seventh polypeptide and the amino acid sequence of SEQ ID NO:26 have at least 85%, 90%, or 95% identity based on the ClustalV alignment method, (h) an eighth nucleotide sequence encoding an eighth polypeptide comprising at least 200 amino acids, wherein the amino acid sequence of the eighth polypeptide and the amino acid sequence of SEQ ID NO:14 or SEQ ID NO:32 have at least 85%, 90%, or 95% identity based on the ClustalV alignment method, (i) a ninth nucleotide sequence encoding a ninth polypeptide comprising at least 250 amino acids, wherein the amino acid sequence of the ninth polypeptide and the amino acid sequence of SEQ ID NO:8 or SEQ ID NO:12 have at least 85%, 90%, or 95% identity based on the ClustalV alignment method, (j) a tenth nucleotide sequence encoding a tenth polypeptide comprising at least 300 amino acids, wherein the amino acid sequence of the tenth polypeptide and the amino acid sequence of SEQ ID NO:42 have at least 85%, 90%, or 95% identity based on the ClustalV alignment method, (k) an eleventh nucleotide sequence encoding an eleventh polypeptide comprising at least 100 amino acids, wherein the amino acid sequence of the eleventh polypeptide and the amino acid sequence of SEQ ID NO:46 have at least 90% or 95% identity based on the ClustalV alignment method, (l) a twelfth nucleotide sequence encoding a twelfth polypeptide comprising at least 150 amino acids, wherein the amino acid sequence of the twelfth polypeptide and the amino acid sequence of SEQ ID NO:4 have at least 90% or 95% identity based on the ClustalV alignment method, (m) a thirteenth nucleotide sequence encoding a thirteenth polypeptide comprising at least 250 amino acids, wherein the amino acid sequence of the thirteenth polypeptide and the amino acid sequence of SEQ ID NO:38 have at least 90% or 95% identity based on the ClustalV alignment method, or (n) the complement of the first, second, third, fourth, fifth, sixth, seventh, eighth, ninth, tenth, eleventh, twelfth, or thirteenth nucleotide sequence, wherein the complement and the first, second, third, fourth, fifth, sixth, seventh, eighth, ninth, tenth, eleventh, twelfth, or thirteenth nucleotide sequence contain the same number of nucleotides and are 100% complementary. The first polypeptide preferably comprises the amino acid sequence of SEQ ID NO:16, SEQ ID NO:18, SEQ ID NO:20, SEQ ID NO:30, SEQ ID NO:36, SEQ ID NO:44, SEQ ID NO:48, or SEQ ID NO:52, the second polypeptide preferably comprises the amino acid sequence of SEQ ID NO:24, the third polypeptide preferably comprises the amino acid sequence of SEQ ID NO:34, the fourth polypeptide preferably comprises the amino acid sequence of SEQ ID NO:10, the fifth polypeptide preferably comprises the amino acid sequence of SEQ ID NO:2, SEQ ID NO:6, SEQ ID NO:22, or SEQ ID NO:50, the sixth polypeptide preferably comprises the amino acid sequence of SEQ ID NO:28, SEQ ID NO:40 or SEQ ID NO:54, the seventh polypeptide preferably comprises the amino acid sequence of SEQ ID NO:26, the eighth polypeptide preferably comprises the amino acid sequence of SEQ ID NO:14 or SEQ ID NO:32, the ninth polypeptide preferably comprises the amino acid sequence of SEQ ID NO:8 or SEQ ID NO:12, the tenth polypeptide preferably comprises the amino acid sequence of SEQ ID NO:42, the eleventh polypeptide preferably comprises the amino acid sequence of SEQ ID NO:46, the twelfth polypeptide preferably comprises the amino acid sequence of SEQ ID NO:4, and the thirteenth polypeptide preferably comprises the amino acid sequence of SEQ ID NO:38. The first nucleotide sequence preferably comprises the nucleotide sequence of SEQ ID NO:15, SEQ ID NO:17, SEQ ID NO:19, SEQ ID NO:29, SEQ ID NO:35, SEQ ID NO:43, SEQ ID NO:47, or SEQ ID NO:51, the second nucleotide sequence preferably comprises the nucleotide sequence of SEQ ID NO:23, the third nucleotide sequence preferably comprises the nucleotide sequence of SEQ ID NO:33, the fourth nucleotide sequence preferably comprises the nucleotide sequence of SEQ ID NO:9, the fifth nucleotide sequence preferably comprises the nucleotide sequence of SEQ ID NO:1, SEQ ID NO:5, SEQ ID NO:21, or SEQ ID NO:49, the sixth nucleotide sequence preferably comprises the nucleotide sequence of SEQ ID NO:27, SEQ ID NO:39, or SEQ ID NO:53, the seventh nucleotide sequence preferably comprises the nucleotide sequence of SEQ ID NO:25, the eighth nucleotide sequence preferably comprises the nucleotide sequence of SEQ ID NO:13 or SEQ ID NO:31, the ninth nucleotide sequence preferably comprises the nucleotide sequence of SEQ ID NO:7 or SEQ ID NO:11, the tenth nucleotide sequence preferably comprises the nucleotide sequence of SEQ ID NO:41, the eleventh nucleotide sequence preferably comprises the nucleotide sequence of SEQ ID NO:45, the twelfth nucleotide sequence preferably comprises the nucleotide sequence of SEQ ID NO:3, and the thirteenth nucleotide sequence preferably comprises the nucleotide sequence of SEQ ID NO:37. The first, second, third, fourth, fifth, sixth, seventh, eighth, ninth, tenth, eleventh, twelfth, and thirteenth polypeptides preferably are polypeptides involved in post-transcriptional gene silencing.

This invention also includes the isolated complement of such polynucleotides, wherein the complement and the polynucleotide preferably consist of the same number of nucleotides, and the nucleotide sequences of the complement and the polynucleotide preferably have 100% complementarity.

Nucleic acid fragments encoding at least a portion of several polypeptides involved in post-transcriptional gene silencing have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other polypeptides involved in post-transcriptional gene silencing, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence of SEQ ID NOs:1, 3, 5, 7, 9, 11, 13, 15, 17, 19, 21, 23, 25, 27, 29, 31, 33, 35, 37, 39, 41, 43, 45, 47, 49, 51 or 53, and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another preferred embodiment, this invention includes viruses and host cells comprising either the recombinant DNA constructs of the invention as described herein or isolated polynucleotides of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of PTGS in those plants. Since some of the AGO1 family members have also been shown to be involved in transposon silencing, meristem development, and differentiation of meristematic tissue, the polynucleotides disclosed herein may also be used to manipulate transposon activity, meristem activity, plant architecture and development, and proliferation of undifferentiated plant cells in culture, which would be useful in callus propagation.

Overexpression of the proteins of the instant invention may be accomplished by first constructing a recombinant DNA construct in which the coding region is operably linked to a promoter capable of directing expression of a gene in the desired tissues at the desired stage of development. The recombinant DNA construct may comprise promoter sequences and translation leader sequences derived from the same genes. 3' Non-coding sequences encoding transcription termination signals may also be provided. The instant recombinant DNA construct may also comprise one or more introns in order to facilitate gene expression.

Plasmid vectors comprising the instant isolated polynucleotide(s) (or recombinant DNA construct(s)) may be constructed. The choice of plasmid vector is dependent upon the method that will be used to transform host plants. The skilled artisan is well aware of the genetic elements that must be present on the plasmid vector in order to successfully transform, select and propagate host cells containing the recombinant DNA construct or chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the recombinant DNA construct(s) described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), nuclear localization signals (Raikhel (1992) *Plant Phys.* 100: 1627-1632) or mitochondrial signal sequences (Zhang and Glaser (2002) *Trends Plant Sci* 7:14-21) with or without removing targeting sequences that are already present.

While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another preferred embodiment, the present invention includes an isolated polypeptide comprising: (a) a first amino acid sequence comprising at least 100 amino acids, wherein the first amino acid sequence and the amino acid sequence of SEQ ID NO:16, SEQ ID NO:18, SEQ ID NO:20, SEQ ID NO:30, SEQ ID NO:36, SEQ ID NO:44, SEQ ID NO:48, or SEQ ID NO:52 have at least 70%, 80%, 85%, 90%, or 95% identity based on the ClustalV alignment method, (b) a second amino acid sequence comprising at least 200 amino acids, wherein the second amino acid sequence and the amino acid sequence of SEQ ID NO:24 have at least 70%, 80%, 85%, 90%, or 95% identity based on the ClustalV alignment method, (c) a third amino acid sequence comprising at least 100 amino acids, wherein the third amino acid sequence and the amino acid sequence of SEQ ID NO:34 have at least 80%, 85%, 90%, or 95% identity based on the ClustalV alignment method, (d) a fourth amino acid sequence comprising at least 150 amino acids, wherein the fourth amino acid sequence and the amino acid sequence of SEQ ID NO:10 have at least 80%, 85%, 90%, or 95% identity based on the ClustalV alignment method, (e) a fifth amino acid sequence comprising at least 200 amino acids, wherein the fifth amino acid sequence and the amino acid sequence of SEQ ID NO:2, SEQ ID NO:6, SEQ ID NO:22, or SEQ ID NO:50 have at least 80%, 85%, 90%, or 95% identity based on the ClustalV alignment method, (f) a sixth amino acid sequence comprising at least 300 amino acids, wherein the sixth amino acid sequence and the amino acid sequence of SEQ ID NO:28, SEQ ID NO:40 or SEQ ID NO:54 have at least 80%, 85%, 90%, or 95% identity based on the ClustalV alignment method, (g) a seventh amino acid sequence comprising at least 100 amino acids, wherein the seventh amino acid sequence and the amino acid sequence of SEQ ID NO:26 have at least 85%, 90%, or 95% identity based on the ClustalV alignment method, (h) an eighth amino acid sequence comprising at least 200 amino acids, wherein the eighth amino acid sequence and the amino acid sequence of SEQ ID NO:14 or SEQ ID NO:32 have at least 85%, 90%, or 95% identity based on the ClustalV alignment method, (i) a ninth amino acid sequence comprising at least 250 amino acids, wherein the ninth amino acid sequence and the amino acid sequence of SEQ ID NO:8 or SEQ ID NO:12 have at least 85%, 90%, or 95% identity based on the ClustalV alignment method, (j) a tenth amino acid sequence comprising at least 300 amino acids, wherein the tenth amino acid sequence and the amino acid sequence of SEQ ID NO:42 have at least 85%, 90%, or 95% identity based on the ClustalV alignment method, (k) an eleventh amino acid sequence comprising at least 100 amino acids, wherein the eleventh amino acid sequence and the amino acid sequence of SEQ ID NO:46 have at least 90% or 95% identity based on the ClustalV alignment method, (l) a twelfth amino acid sequence comprising at least 150 amino acids, wherein the twelfth amino acid sequence and the amino acid sequence of SEQ ID NO:4 have at least 90% or 95% identity based on the ClustalV alignment method, or (m) a thirteenth amino acid sequence comprising at least 250 amino acids, wherein the thirteenth amino acid sequence and the amino acid sequence of SEQ ID NO:38 have at least 90% or 95% identity based on the ClustalV alignment method. The first amino acid sequence preferably comprises the amino acid sequence of SEQ ID NO:16, SEQ ID NO:18, SEQ ID NO:20, SEQ ID NO:30, SEQ ID NO:36, SEQ ID NO:44, SEQ ID NO:48, or SEQ ID NO:52, the second amino acid sequence preferably comprises the amino acid sequence of SEQ ID NO:24, the third amino acid sequence preferably comprises the amino acid sequence of SEQ ID NO:34, the fourth amino acid sequence preferably comprises the amino acid sequence of SEQ ID NO:10, the fifth amino acid sequence preferably comprises the amino acid sequence of SEQ ID NO:2, SEQ ID NO:6, SEQ ID NO:22, or SEQ ID NO:50, the sixth amino acid sequence preferably comprises the amino acid sequence of SEQ ID NO:28, SEQ ID NO:40 or SEQ ID NO:54, the seventh amino acid sequence preferably comprises the amino acid sequence of SEQ ID NO:26, the eighth amino acid sequence preferably comprises the amino acid sequence of SEQ ID NO:14 or SEQ ID NO:32, the ninth amino acid sequence preferably comprises the amino acid sequence of SEQ ID NO:8 or SEQ ID NO:12, the tenth amino acid sequence preferably comprises the amino acid sequence of SEQ ID NO:42, the eleventh amino acid sequence preferably comprises the amino acid sequence of SEQ ID NO:46, the twelfth amino acid sequence preferably comprises the amino acid sequence of SEQ ID NO:4, and the thirteenth amino acid sequence preferably comprises the amino acid sequence of SEQ ID NO:38. The polypeptide preferably is a polypeptide involved in post-transcriptional gene silencing.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct recombinant DNA constructs for production of the instant polypeptides. This recombinant DNA construct could then be introduced into appropriate microorganisms via transformation to provide high level expression of the encoded polypeptides involved in post-transcriptional gene silencing. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

Nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several kb to several hundred kb; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding one of the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding one of the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various corn (*Zea mays*), soybean (*Glycine max*), rice (*Oryza sativa*), and wheat (*Triticum aestivum*) tissues were prepared. The characteristics of the libraries are described below.

TABLE 2 cDNA Libraries from Corn, Rice, Soybean, and Wheat

| Library | Tissue | Clone |
| --- | --- | --- |
| cle1f | Corn Leaf at VE-V5 Stage** | cle1f.pk002.k13 |
| cpf1c | Corn Treated with Chemicals Related to Protein Synthesis*** | cpf1c.pk008.j24 |
| csc1c | Corn 20 Day Seedling (Germination Cold Stress) | csc1c.pk006.j19 |
| ctn1c | Corn Tassel, Night Harvested | ctn1c.pk003.i20 |
| p0002 | Corn Tassel, Premeiotic Cells to Early Uninucleate Stage | p0002.cgevj06r |
| p0102 | Corn Early Meiosis Tassels* | p0102.cerae32ra p0102.cerba57r |
| p0107 | Corn Whole Kernels 7 Days After Pollination* | p0107.cbcbd69r |
| p0119 | Corn V12 Stage** Ear Shoot With Husk, Night Harvested* | p0119.cmtmm21r |
| p0125 | Corn Anther Prophase I* | p0125.czaab55r p0125.czaat57r |
| rca1n | Rice Callus* | rca1n.pk018.b3 |
| rdi2c | Rice (*Oryza sativa*, Nipponbare) developing inflorescence at rachis branch-floral organ primordia formation | rdi2c.pk002.d14 |
| rl0n | Rice 15 Day Old Leaf* | rl0n.pk124.g8 |
| rlm1n | Rice Leaf 15 Days After Germination, Harvested 2-72 Hours Following Infection With *Magnaporta grisea* (4360-R-62 and 4360-R-67)* | rlm1n.pk001.m11 |
| rls6 | Susceptible Rice Leaf 15 Days After Germination, 6 Hours After Infection of Strain *Magnaporthe grisea* 4360-R-67 (AVR2-YAMO) | rls6.pk0082.d4 |
| rsl1n | Rice 15-Day-Old Seedling* | rsl1n.pk004.d12 |
| rtc1c | Rice Leaf Inoculated with *Magnaporthe grisea* Strain 0184 at 4, 8, and 24 Hours | rtc1c.pk008.k19.f |
| sdc1c | Soybean Developing Cotyledon (3-5 mm) | sdc1c.pk0004.d11 |
| sdc2c | Soybean Developing Cotyledon (6-7 mm) | sdc2c.pk001.p4 |
| ses2w | Soybean Embryogenic Suspension 2 Weeks After Subculture | ses2w.pk0009.g6 |
| ssl1c | Soybean Seed 25 Days After Fertilization | ssl1c.pk003.g3 |
| ssm | Soybean Shoot Meristem | ssm.pk0063.a4 |
| wdk1c | Wheat Developing Kernel, 3 Days After Anthesis | wdk1c.pk012.i2 |

TABLE 2-continued cDNA Libraries from Corn, Rice, Soybean, and Wheat

| Library | Tissue | Clone |
| --- | --- | --- |
| wlm96 | Wheat Seedlings 96 Hours After Inoculation With *Erysiphe graminis* f. sp *tritici* | wlm96.pk029.c23 |
| wne1g | Wheat Nebulized Genomic Library | wne1g.pk003.f8 |
| wr1 | Wheat Root From 7 Day Old Light Grown Seedling | wr1.pk0073.c7 |
| wre1n | Wheat Root From 7 Day Old Etiolated Seedling* | wre1n.pk0001.h6 wre1n.pk162.h10 |

*These libraries were normalized essentially as described in U.S. Pat. No. 5,482,845, incorporated herein by reference.
**Corn developmental stages are explained in the publication "How a corn plant develops" from the Iowa State University Coop. Ext. Service Special Report No. 48 reprinted June 1993.
***Chemicals used included chloramphenicol, cyclohexamide, aurintricarboxylic acid, all of which are commercially available from Calbiochem-Novabiochem Corp. (1-800-628-8470)

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phred/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding polypeptides involved in post-transcriptional gene silencing were identified by conducting BLAST (Basic Local Alignment Search Tool; Altschul et al. (1993) *J. Mol. Biol.* 215:403-410; see also the explanation of the BLAST algorithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389-3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Polypeptides Involved in Post-Transcriptional Gene Silencing The BLASTX search using the EST sequences from clones listed in Table 3 revealed similarity of the polypeptides encoded by the cDNAs to polypeptides involved in post-transcriptional gene silencing and AGO1 family members from *Neurospora crassa* (NCBI GenBank Identifier (GI) No. 7248733), *Arabidopsis thaliana* (NCBI GI Nos. 3885334, 6692120, 11386626, 2149640, 5107374, 12643935 and 15221177), and *Oryza sativa* (NCBI GI No. 6539559). The following three *Arabidopsis thaliana* sequences each represent the same 1048 amino acid sequence: GI No. 11386626; GI No. 2149640; and GI No. 15221177. The following two *Arabidopsis thaliana* sequences each represent the same 988 amino acid sequence: GI No. 5107374 and GI No. 12643935. Shown in Table 3 are the BLAST results for individual ESTs ("EST"), the sequences of the entire cDNA inserts comprising the indicated cDNA clones ("FIS"), the sequences of contigs assembled from two or more EST, FIS or PCR sequencess ("Contig"), or sequences encoding an entire protein, or functionally active polypeptide, derived from an FIS or a contig ("CGS"):

TABLE 3

Ptions BLAST Results for Sequences Encoding Polypeptides Homologous to Polypeptides Involved in Post-Transcriptional Gene Silencing (AGO1 Protein Family)

| | | BLAST Results | |
|---|---|---|---|
| Clone | Status | NCBI GI No. | BLAST pLog Score |
| p0102.cerba57r | FIS | 12643935 | >180.00 |
| ses2w.pk0009.g6 | FIS | 5107374 | >180.00 |
| ssm.pk0063.a4 | FIS | 5107374 | >180.00 |
| cle1f.pk002.k13 (FIS) | CGS | 6539559 | >180.00 |
| cpf1c.pk008.j24 | FIS | 2149640 | >180.00 |
| csc1c.pk006.j19 (FIS) | CGS | 2149640 | >180.00 |
| ctn1c.pk003.i20 (FIS) | CGS | 2149640 | >180.00 |
| Contig of p0002.cgevj06r p0125.czaab55r (FIS) p0125.czaat57r | Contig | 11386626 | >180.00 |
| p0102.cerae32ra | EST | 5107374 | 31.10 |
| p0107.cbcbd69r | EST | 2149640 | 57.15 |
| p0119.cmtmm21r (FIS) | CGS | 6539559 | >180.00 |
| rca1n.pk018.b3 | FIS | 2149640 | >180.00 |
| rl0n.pk124.g8 | FIS | 2149640 | 131.00 |
| Contig of rlm1n.pk001.m11 (FIS) PCR fragment sequence | CGS | 11386626 | >180.00 |
| rls6.pk0082.d4 | FIS | 6539559 | 31.70 |
| rsl1n.pk004.d12 | FIS | 11386626 | 171.00 |
| rtc1c.pk008.k19.f | EST | 2149640 | 64.22 |
| sdc1c.pk0004.d11 | FIS | 6692120 | 76.05 |
| Contig of sdc2c.pk001.p4 (FIS) PCR fragment sequence | CGS | 2149640 | >180.00 |
| ssl1c.pk003.g3 (FIS) | CGS | 3885334 | >180.00 |
| Contig of wdk1c.pk012.i2 (FIS) PCR fragment sequence | CGS | 6539559 | >180.00 |
| wlm96.pk029.c23 | FIS | 7248733 | 45.30 |
| wne1g.pk003.f8 | EST | 2149640 | 47.10 |
| wr1.pk0073.c7 | EST | 2149640 | 27.70 |
| wre1n.pk0001.h6 | FIS | 6539559 | >180.00 |
| wre1n.pk162.h10 | EST | 2149640 | 30.70 |
| rdi2c.pk002.d14 (FIS) | CGS | 15221177 | >180.00 |

FIGS. 1A-1D present an alignment of the amino acid sequences set forth in SEQ ID NOs:8, 22, 40, and 42, and the *Oryza sativa* sequence (NCBI GI No. 6539559; SEQ ID NO:55). FIGS. 2A-2E present an alignment of the amino acid sequences set forth in SEQ ID NOs:12, 14, 28, and 38, and the *Arabidopsis thaliana* sequence (NCBI GI No. 2149640; SEQ ID NO:56). The data in Table 5 represents a calculation of the percent identity of the amino acid sequences set forth in SEQ ID NOs:8, 12, 14, 22, 28, 38, 40, and 42, the *Oryza sativa* sequence (NCBI GI No. 6539559; SEQ ID NO: 55), and the *Arabidopsis thaliana* sequence (NCBI GI No. 2149640; SEQ ID NO: 56).

TABLE 5

Percent Identity of Amino Acid Sequences Deduced From the Nucleotide Sequences Encoding Polypeptides Homologous to Polypeptides Involved in Post-Transcriptional Gene Silencing (AGO1 Protein Family)

| SEQ ID NO. | NCBI GI No. | Percent Identity |
|---|---|---|
| 8 | 6539559 | 82.2 |
| 12 | 2149640 | 72.1 |
| 14 | 2149640 | 72.6 |
| 22 | 6539559 | 73.2 |
| 28 | 2149640 | 72.2 |
| 38 | 2149640 | 78.2 |
| 40 | 6539559 | 68.8 |
| 42 | 6539559 | 83.7 |
| 54 | 2149640 | 73.3 |

Sequence alignments and percent identity calculations were performed using the Megalign program of the LASERGENE bioinformatics computing suite (DNASTAR Inc., Madison, Wis.). Multiple alignment of the sequences was performed using the ClustalV method of alignment (Higgins and Sharp (1989) *CABIOS.* 5:151-153) with the default parameters (GAP PENALTY=10, GAP LENGTH PENALTY=10). Default parameters for pairwise alignments using the ClustalV method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a polypeptide involved in post-transcriptional gene silencing. These sequences represent the first corn and wheat sequences indicated to encode polypeptides involved in post-transcriptional gene silencing (AGO1 protein family) known to Applicants.

Example 4

Expression of Recombinant DNA Constructs in Monocot Cells

A recombinant DNA construct comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone, plant cDNA or plant cDNA libraries using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptide, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialaphos (5 mg per liter) and lacks casein or proline. The tissue continues to grow slowly on this medium. After an additional 2 weeks the tissue can be transferred to fresh N6 medium containing bialaphos. After 6 weeks, areas of about 1 cm in diameter of actively growing callus can be identified on some of the plates containing the bialaphos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Plants in which PTGS has been elevated or diminished can be assayed by making the following two sexual crosses: (1) a first transgenic plant, transformed with a gene encoding a polypeptide involved in PTGS, is crossed with a second transgenic plant that contains an active reporter transgene, such as the GUS gene, and (2), the first transgenic plant is crossed with a third transgenic plant that contains a post-transcriptionally silenced reporter gene. If PTGS has been elevated, reporter gene expression in the progeny plants from the first cross should be reduced. If PTGS has been diminished, reporter gene expression in progeny plants from the second cross should be increased. Also, if PTGS has been diminished, a correlated decrease in the methylation state of the reporter transgene in the progeny of the second cross would be expected (Fagard et al. (2000) *Proc Natl Acad Sci USA* 97:11650-11654).

Example 5

Expression of Recombinant DNA Constructs in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone, plant cDNA or plant cDNA libraries, using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Recombinant DNA Constructs in Microbial Cells

The cDNA fragment of the gene may be generated by polymerase chain reaction (PCR) of the cDNA clone, plant cDNA or plant cDNA libraries, using appropriate oligonucleotide primers. The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and Hind III sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Expression of Recombinant DNA Constructs in Yeast Cells

The polypeptides encoded by the polynucleotides of the instant invention may be expressed in a yeast (*Saccharomyces cerevisiae*) strain YPH. Plasmid DNA, plant cDNA or plant cDNA libraries, may be used as template to amplify the portion encoding the polypeptide involved in post-transcriptional gene silencing. Amplification may be performed using the GC melt kit (Clontech) with a 1 M final concentration of GC melt reagent and using a Perkin Elmer 9700 thermocycler. The amplified insert may then be incubated with a modified pRS315 plasmid (NCBI General Identifier No. 984798; Sikorski, R. S. and Hieter, P. (1989) *Genetics* 122:19-27) that has been digested with Not I and Spe I. Plasmid pRS315 has been previously modified by the insertion of a bidirectional gall/10 promoter between the Xho I and Hind III sites. The plasmid may then be transformed into the YPH yeast strain using standard procedures where the insert recombines through gap repair to form the desired transformed yeast strain (Hua, S. B. et al. (1997) *Plasmid* 38:91-96).

Yeast cells may be prepared according to a modification of the methods of Pompon et al. (Pompon, D. et al. (1996) *Meth. Enz.* 272:51-64). Briefly, a yeast colony will be grown overnight (to saturation) in SG (-Leucine) medium at 30° C. with good aeration. A 1:50 dilution of this culture will be made into 500 mL of YPGE medium with adenine supplementation and allowed to grow at 30° C. with good aeration to an $OD_{600}$ of 1.6 (24-30 h). Fifty mL of 20% galactose will be added, and the culture allowed to grow overnight at 30° C. The cells will be recovered by centrifugation at 5,500 rpm for five minutes in a Sorvall GS-3 rotor. The cell pellet resuspended in 500 mL of 0.1 M potassium phosphate buffer (pH 7.0) and then allowed to grow at 30° C. for another 24 hours.

The cells may be recovered by centrifugation as described above and the presence of the polypeptide of the instant invention determined by HPLC/mass spectrometry or any other suitable method.

Example 8

Expression of Recombinant DNA Constructs in Insect Cells

The cDNA fragment of the gene may be generated by polymerase chain reaction (PCR) of the cDNA clone, plant cDNA or plant cDNA libraries, using appropriate oligonucleotide primers. The cDNAs encoding the instant polypeptides may be introduced into the baculovirus genome itself. For this purpose the cDNAs may be placed under the control of the polyhedron promoter, the 1E1 promoter, or any other one of the baculovirus promoters. The cDNA, together with appropriate leader sequences is then inserted into a baculovirus transfer vector using standard molecular cloning techniques. Following transformation of *E. coli* DH5α, isolated colonies are chosen and plasmid DNA is prepared and is analyzed by restriction enzyme analysis. Colonies containing the appropriate fragment are isolated, propagated, and plasmid DNA is prepared for cotransfection.

*Spodoptera frugiperda* cells (Sf-9) are propagated in ExCell® 401 media (JRH Biosciences, Lenexa, Kans.) supplemented with 3.0% fetal bovine serum. Lipofectin® (50 µL at 0.1 mg/mL, Gibco/BRL) is added to a 50 µL aliquot of the transfer vector containing the toxin gene (500 ng) and linearized polyhedrin-negative AcNPV (2.5 µg, Baculogold® viral DNA, Pharmigen, San Diego, Calif.). Sf-9 cells (approximate 50% monolayer) are co-transfected with the viral DNA/transfer vector solution. The supernatant fluid from the co-transfection experiment is collected at 5 days post-transfection and recombinant viruses are isolated employing standard plaque purification protocols, wherein only polyhedrin-positive plaques are selected (O'Reilly et al. (1992), *Baculovirus Expression Vectors: A Laboratory Manual*, W. H. Freeman and Company, New York.). Sf-9 cells in 35 mM petri dishes (50% monolayer) are inoculated with 100 µL of a serial dilution of the viral suspension, and supernatant fluids are collected at 5 days post infection. In order to prepare larger quantities of virus for characterization, these supernatant fluids are used to inoculate larger tissue cultures for large-scale propagation of recombinant viruses.

What is claimed is:

1. A recombinant DNA construct comprising a polynucleotide operably linked to at least one heterologous regulatory sequence, said polynucleotide comprising:
   (a) a nucleotide sequence encoding a polypeptide, wherein the amino acid sequence of the polypeptide has at least 95% sequence identity to the amino acid sequence of SEQ ID NO:8, wherein a transgenic maize plant expressing the polynucleotide has an elevated level of transposon silencing compared to a non-transgenic plant, or
   (b) the full-length complement of the nucleotide sequence of (a), wherein a transgenic maize plant expressing the polynucleotide has a dimished level of transposon silencing compared to a non-transgenic plant.

2. The recombinant DNA construct of claim 1, wherein the amino acid sequence of the polypeptide comprises the amino acid sequence of SEQ ID NO:8.

3. The recombinant DNA construct of claim 1, wherein the nucleotide sequence comprises the nucleotide sequence of SEQ ID NO:7.

4. A vector comprising the recombinant DNA construct of claim 1.

5. The recombinant DNA construct of claim 1, wherein the at least one heterologous regulatory sequence is a promoter.

6. A method for transforming a cell, comprising transforming a cell with the recombinant DNA construct of claim 1.

7. A cell comprising the recombinant DNA construct of claim 1.

8. A method for production of a polypeptide comprising an amino acid sequence having at least 95% identity to the amino acid sequence of SEQ ID NO:8, the method comprising the steps of cultivating a cell comprising the recombinant DNA construct of claim 1 (a) in a culture medium under conditions that allow for the synthesis of the polypeptide and isolating the polypeptide from the cultivated cells, from the culture medium, or from both the cultivated cells and the culture medium.

9. A method for producing a transgenic plant comprising transforming a plant cell with the recombinant DNA construct of claim 1 and regenerating a transgenic plant from the transformed plant cell.

10. A plant comprising the recombinant DNA construct of claim 1.

11. A seed comprising the recombinant DNA construct of claim 1.

12. A cDNA comprising a nucleotide sequence encoding a polypeptide having at least 95% sequence identity to the amino acid sequence of SEQ ID NO:8, and wherein said polypeptide has post-transcriptional gene silencing activity when expressed in a maize plant cell.

13. The cDNA of claim 12, wherein the amino acid sequence of the polypeptide comprises the amino acid sequence of SEQ ID NO:8.

14. The cDNA of claim 12, wherein the nucleotide sequence comprises the nucleotide sequence of SEQ ID NO:7.

* * * * *

SEQUENCE LISTING

```
<160> NUMBER OF SEQ ID NOS: 56

<210> SEQ ID NO 1
<211> LENGTH: 2042
<212> TYPE: DNA
<213> ORGANISM: Zea mays

<400> SEQUENCE: 1
ccacgcgtcc gatgaaatct gtcgtggagt acttcaagga aatgtatggt ttcaccattc      60
agcatcctca tcttccttgc cttcaggttg gaaaccaaaa gaaggcgaac tatttaccaa     120
tggaggcctg caagatcgtt gaaggccaga gatacacgaa gaggttgaat gaaaaacaga     180
tcacatcgtt gctaaaggtt acatgccaaa ggcctcgaga acaagagatg gatattttac     240
agacagttca tcaaaatgga tatgagcaag atccatatgc gaaggaattt gggatcaaca     300
ttagtgagaa gctaacctat gttgaagccc gagtccttcc tgcaccttgg ctgaagtatc     360
atgacactgg aaaagagaaa gagtgcttac cacaggttgg tcagtggaac atggtaaaca     420
agaaagtgat aaacggatgc aaggtgagcc actgggcatg tataaacttc tcaaggagtg     480
ttccagaagc cacagctcgg ggattttgcc aggaattggc acaaatgtgt caaatttcgg     540
gcatggaatt taacagtgag cccgtgatgc caatatattc agctagacca gatcaagtag     600
tgaaggcact taaaagtgtg tataatattg cactgaacaa actcaagggt aaagaacttg     660
```

```
aacttcttct ggctatactc cccgacaaca atggtccgtt atatggtgac atcaaacgta      720
tttgtgaaac tgatttggga ttgatatcac aatgttgctt aaccaagcat gttttaaga      780 tcagcaaaca gtacttggca aatgtctcac tgaaaattaa tgttaagatg ggaggaagaa      840
acactgtgct cctggacgca ataagttgga gcattccttt ggtcagtgac atcccaacta      900
ttatatttgg tgcagatgta acacaccctg aaaccgggga ggactcaagt ccatcaatcg      960
ctgccgttgt tgcttctcaa gattggccag aagttacaaa gtatgctgga ttggtttgtg     1020
ctcaggcaca ccggcaagag ctcattcagg acctttacaa acatggcac gatcctcaga      1080 gaggcactgt aacaggcggc atgatcaggg agctgttaat atccttcagg aaggccactg     1140
ggcagaagcc attgagaata atattctaca gggacggtgt tagtgaaggc cagttctatc     1200
aagttctcct ttacgagtta gatgccatcc gtaaggcatg cgcatcccta gaaccaaatt     1260
accagcctcc tgtaacattt gtggtggttc aaaaacgtca tcatacgaga ctatttacaa     1320
acaatcacaa agacagaagt agcatggaca agagtggaaa tattttgcca ggaactgttg     1380
ttgattctaa gatatgccac ccaacagagt ttgattctca cctctgtagt catgctggaa     1440
tccagggaac aagtaggccc gctcactacc atgtcctctg ggatgagaac aatttcacag     1500
cagacgaaat gcaaacactg acaaacaacc tttgctacac ttatgcccgg tgcacacgct     1560
cggtttctgt tgtccctcct gcatactacg cacacctggc agcattccgg gcgcggttct     1620
acatggaacc agagatgtcg gagaaccaga cgtcgaagag ctccaatggc acgaacggag     1680
gcttggtgaa gcccctgcct gctgtgaagg agaaggtgaa aagggtgatg ttctactgct     1740
gacgaggtga ccgctttaac aaccattcac atgctgtagc taacttggta gggttcagta     1800
ggggattaga ttagctttct ccaggaacga agaggaaacg ggatgcgtat tggatcatg      1860 aacaatcaat ctgttagcga tcgctgtaaa atactcggaa atgcctgtat aatagttctt     1920
gttggttcag atgcatgcat ccaatgttcc agtgtactat gaaaaggggg tgtagaagaa     1980
accttctggt gttttctagg ttgaaaaaaa aaaaaaaaaa aaaaaacaaa aaaaaaaaa      2040 aa                                                                   2042
```

<210> SEQ ID NO 2
<211> LENGTH: 577
<212> TYPE: PRT
<213> ORGANISM: Zea mays

<400> SEQUENCE: 2

```
Pro Met Lys Ser Val Val Glu Tyr Phe Lys Glu Met Tyr Gly Phe Thr
 1               5                  10                  15

Ile Gln His Pro His Leu Pro Cys Leu Gln Val Gly Asn Gln Lys Lys
            20                  25                  30

Ala Asn Tyr Leu Pro Met Glu Ala Cys Lys Ile Val Glu Gly Gln Arg
        35                  40                  45

Tyr Thr Lys Arg Leu Asn Glu Lys Gln Ile Thr Ser Leu Leu Lys Val
    50                  55                  60

Thr Cys Gln Arg Pro Arg Glu Gln Glu Met Asp Ile Leu Gln Thr Val
65                  70                  75                  80

His Gln Asn Gly Tyr Glu Gln Asp Pro Tyr Ala Lys Glu Phe Gly Ile
                85                  90                  95

Asn Ile Ser Glu Lys Leu Thr Tyr Val Glu Ala Arg Val Leu Pro Ala
            100                 105                 110

Pro Trp Leu Lys Tyr His Asp Thr Gly Lys Glu Lys Glu Cys Leu Pro
        115                 120                 125
```

-continued

Gln Val Gly Gln Trp Asn Met Val Asn Lys Lys Val Ile Asn Gly Cys
130                 135                 140

Lys Val Ser His Trp Ala Cys Ile Asn Phe Ser Arg Ser Val Pro Glu
145                 150                 155                 160

Ala Thr Ala Arg Gly Phe Cys Gln Glu Leu Ala Gln Met Cys Gln Ile
                165                 170                 175

Ser Gly Met Glu Phe Asn Ser Glu Pro Val Met Pro Ile Tyr Ser Ala
            180                 185                 190

Arg Pro Asp Gln Val Val Lys Ala Leu Lys Ser Val Tyr Asn Ile Ala
        195                 200                 205

Leu Asn Lys Leu Lys Gly Lys Glu Leu Glu Leu Leu Ala Ile Leu
210                 215                 220

Pro Asp Asn Asn Gly Pro Leu Tyr Gly Asp Ile Lys Arg Ile Cys Glu
225                 230                 235                 240

Thr Asp Leu Gly Leu Ile Ser Gln Cys Cys Leu Thr Lys His Val Phe
            245                 250                 255

Lys Ile Ser Lys Gln Tyr Leu Ala Asn Val Ser Leu Lys Ile Asn Val
        260                 265                 270

Lys Met Gly Gly Arg Asn Thr Val Leu Leu Asp Ala Ile Ser Trp Ser
        275                 280                 285

Ile Pro Leu Val Ser Asp Ile Pro Thr Ile Ile Phe Gly Ala Asp Val
290                 295                 300

Thr His Pro Glu Thr Gly Glu Asp Ser Ser Pro Ser Ile Ala Ala Val
305                 310                 315                 320

Val Ala Ser Gln Asp Trp Pro Glu Val Thr Lys Tyr Ala Gly Leu Val
            325                 330                 335

Cys Ala Gln Ala His Arg Gln Glu Leu Ile Gln Asp Leu Tyr Lys Thr
        340                 345                 350

Trp His Asp Pro Gln Arg Gly Thr Val Thr Gly Gly Met Ile Arg Glu
        355                 360                 365

Leu Leu Ile Ser Phe Arg Lys Ala Thr Gly Gln Lys Pro Leu Arg Ile
370                 375                 380

Ile Phe Tyr Arg Asp Gly Val Ser Glu Gly Gln Phe Tyr Gln Val Leu
385                 390                 395                 400

Leu Tyr Glu Leu Asp Ala Ile Arg Lys Ala Cys Ala Ser Leu Glu Pro
            405                 410                 415

Asn Tyr Gln Pro Pro Val Thr Phe Val Val Gln Lys Arg His His
        420                 425                 430

Thr Arg Leu Phe Thr Asn Asn His Lys Asp Arg Ser Ser Met Asp Lys
        435                 440                 445

Ser Gly Asn Ile Leu Pro Gly Thr Val Val Asp Ser Lys Ile Cys His
450                 455                 460

Pro Thr Glu Phe Asp Phe Tyr Leu Cys Ser His Ala Gly Ile Gln Gly
465                 470                 475                 480

Thr Ser Arg Pro Ala His Tyr His Val Leu Trp Asp Glu Asn Asn Phe
            485                 490                 495

Thr Ala Asp Glu Met Gln Thr Leu Thr Asn Asn Leu Cys Tyr Thr Tyr
        500                 505                 510

Ala Arg Cys Thr Arg Ser Val Ser Val Val Pro Pro Ala Tyr Tyr Ala
        515                 520                 525

His Leu Ala Ala Phe Arg Ala Arg Phe Tyr Met Glu Pro Glu Met Ser
530                 535                 540

| Glu | Asn | Gln | Thr | Ser | Lys | Ser | Ser | Asn | Gly | Thr | Asn | Gly | Gly | Leu | Val |
|-----|-----|-----|-----|-----|-----|-----|-----|-----|-----|-----|-----|-----|-----|-----|-----|
| 545 |     |     |     |     | 550 |     |     |     |     | 555 |     |     |     |     | 560 |

| Lys | Pro | Leu | Pro | Ala | Val | Lys | Glu | Lys | Val | Lys | Arg | Val | Met | Phe | Tyr |
|-----|-----|-----|-----|-----|-----|-----|-----|-----|-----|-----|-----|-----|-----|-----|-----|
|     |     |     |     | 565 |     |     |     |     | 570 |     |     |     |     | 575 |     |

Cys

<210> SEQ ID NO 3
<211> LENGTH: 2827
<212> TYPE: DNA
<213> ORGANISM: Glycine max

<400> SEQUENCE: 3

```
ttctagaaca gtaaacaggt ctatcatagc agaactagtg aggctgtata aagagtctga      60
cttggggatg agacttccag catatgatgg cagaaaaagt ttgtacactg cagggcagct     120
tcccttttgct tggagagagt ttaagattaa gcttatagat gaagaggatg gagttaatgg    180
ccctaaaagg gaaagagagt acagggtggt gatcaagttc gttgctcggg ctaacttgta    240
tcacttggga cagtttctag ctggtaggcg tgctgatgca ccgcaagagg cacttcaaat    300
tcttgacatt gtattaagag agctgtcaac taagaggtat tgccctattg ggaggtcctt    360
cttttcacct gatattagaa caccgcaacg gcttggagag ggattagaat catggtgtgg    420
attttaccag agtataaggc ctacacaaat gggccttttcc cttaatattg atatggcgtc    480
tgctgcgttt attgagcctc ttccagtagt ggaatttgtt ggccagctat agcaaaaga    540
tgtgctgtca aggccattgt cagatgctga tcgcattaag attaagaaag cccttagagg    600
agttaaagtt gaagtaacac acagaggaag tgtgagaaga aaatatcgtg tttctggatt    660
gacttctcaa ccaaccagag aacttgtgtt tcctgttgat gagaactcaa ctatgaaatc    720
agtagttgaa tacttccaag agatgtatgg tttcactatt caatatactc accttccttg    780
ccttcaagta ggaaaccaaa agaaggctaa ctatttacct atggaggcct gcaaaattgt    840
tgaggggcaa cgttatacaa aaagattgaa tgagaagcaa attacagctc tgttgaaagt    900
tacttgccag agacctcgcg atcgggaaaa tgacatttta cggaccgttc aacataatgc    960
ttatgatcaa gatccttatg caaggaattt ggaattaaaa atcagtgaaa agctagcttc   1020
tgttgaagca cgaattcttc cggcccttg gcttaaatat cacgaaagtg ggaaagagaa   1080
gaactgttta ccccaagttg gtcagtggaa tatgatgaac aagaaaatga ttaatggaat   1140
gactgttagc cggtgggcat gcataaattt ttcaaggagc gtgcaagata tgttgctcg    1200
cacttttgt aatgaacttg ctcaaatgtg tcaagtatct ggcatggaat ttaatccaga    1260
gtctgttatt cccatctaca atgccaaacc tgaacaggtg gaaaaagctt tgaaacatgt    1320
ttaccatgtg tcagggagca aaattaaagg aaaggaattg gagcttttgt tagcaatatt    1380
gccagacaat aacgggtctc tctatggtga tctcaagcga atttgtgaaa ctgaccttgg    1440
tttaatttca caatgctgtc tgacaaagca tgtcttcaaa atcactaaac agtacttggc    1500
taatgtgtct ctgaagatca atgtgaagat gggaggtaga aacactgtac ttcttgatgc    1560
tgtaagcagc agaataccat tggttagtga catgccaacc ataattttcg gagcagatgt    1620
aacccaccct gaaaatggag aagaattgag cccttcaata gcagctgtag tcgcatccca    1680
ggactggccc gaagtgacaa aatatgccgg tttagtatgt gctcaagctc ataggcagga    1740
acttatacaa gatttgtaca aaacttggca agaccctgtt cgtggcacag ttagtggtgg    1800
catgatccga gatttactgg tttccttcag aaaggcaaca ggacaaaagc cactacgaat    1860
tatattttac agggatggtg taagtgaagg acaatttac caagttttac tttatgagtt    1920
```

```
agatgcaatt cggaaggcat gtgcttcctt agaaccaaac taccagcctc cagtaacttt     1980
catagttgtg caaaaaagac atcataccog gttatttgca aacaactaca gggacagaag     2040
cagtacagat cggagtggga atatattgcc tgggactgtt gttgatacca aaatctgcca     2100
tccaacagaa tttgattttt atctctgcag ccatgctggc atccagggta ctagtcggcc     2160
agctcattat catgtcctgt gggatgaaaa caacttcaca cctgatggaa ttcagtctct     2220
gacaaacaac ctttgttata catatgccag gtgtacacgc tcagtatcag ttgttcctcc     2280
agcatattat gcacatttag cagcgtttcg agcacgtttc tatatggaac cagatatgca     2340
agacaatggc tctgcaggtg acggtaatgg tcatggtgcc aaagcaacac gagcagctgg     2400
tgattatagt gtcaagccat tgccagactt gaaagaaaat gtgaagagag tcatgtttta     2460
ctgttagact gcttagtggc ttggccttgg tagaatgata gatatatggg gcaagcatca     2520
acatgataag caagttttca atcatggag tgcaatgttc acctcacatt actttgtaca     2580
ttagtcgtgt aggttttgct gtggtagatc catgattaca gttcttgagc catagtttag     2640
aatgaatttc tacaagcatt attaggtttt atatagatgc caaatttagc attgtaaaaa     2700
atattctctg tcaatctttg tagaaaattt tgccataagg cctttacaga tgctggagta     2760
gaaatttcct tcatctttgc aaggaggga agttttttcc tagtaaaaaa aaaaaaaaaa     2820
aaaaaaa                                                                2827
```

<210> SEQ ID NO 4
<211> LENGTH: 821
<212> TYPE: PRT
<213> ORGANISM: Glycine max

<400> SEQUENCE: 4

```
Ser Arg Thr Val Asn Arg Ser Ile Ile Ala Glu Leu Val Arg Leu Tyr
  1               5                  10                  15

Lys Glu Ser Asp Leu Gly Met Arg Leu Pro Ala Tyr Asp Gly Arg Lys
             20                  25                  30

Ser Leu Tyr Thr Ala Gly Gln Leu Pro Phe Ala Trp Arg Glu Phe Lys
         35                  40                  45

Ile Lys Leu Ile Asp Glu Glu Asp Gly Val Asn Gly Pro Lys Arg Glu
     50                  55                  60

Arg Glu Tyr Arg Val Val Ile Lys Phe Val Ala Arg Ala Asn Leu Tyr
 65                  70                  75                  80

His Leu Gly Gln Phe Leu Ala Gly Arg Arg Ala Asp Ala Pro Gln Glu
                 85                  90                  95

Ala Leu Gln Ile Leu Asp Ile Val Leu Arg Glu Leu Ser Thr Lys Arg
            100                 105                 110

Tyr Cys Pro Ile Gly Arg Ser Phe Phe Ser Pro Asp Ile Arg Thr Pro
        115                 120                 125

Gln Arg Leu Gly Glu Gly Leu Glu Ser Trp Cys Gly Phe Tyr Gln Ser
    130                 135                 140

Ile Arg Pro Thr Gln Met Gly Leu Ser Leu Asn Ile Asp Met Ala Ser
145                 150                 155                 160

Ala Ala Phe Ile Glu Pro Leu Pro Val Val Glu Phe Val Gly Gln Leu
                165                 170                 175

Leu Ala Lys Asp Val Leu Ser Arg Pro Leu Ser Asp Ala Asp Arg Ile
            180                 185                 190

Lys Ile Lys Lys Ala Leu Arg Gly Val Lys Val Glu Val Thr His Arg
        195                 200                 205
```

-continued

```
Gly Ser Val Arg Arg Lys Tyr Arg Val Ser Gly Leu Thr Ser Gln Pro
    210                 215                 220

Thr Arg Glu Leu Val Phe Pro Val Asp Glu Asn Ser Thr Met Lys Ser
225                 230                 235                 240

Val Val Glu Tyr Phe Gln Glu Met Tyr Gly Phe Thr Ile Gln Tyr Thr
                245                 250                 255

His Leu Pro Cys Leu Gln Val Gly Asn Gln Lys Lys Ala Asn Tyr Leu
            260                 265                 270

Pro Met Glu Ala Cys Lys Ile Val Glu Gly Gln Arg Tyr Thr Lys Arg
        275                 280                 285

Leu Asn Glu Lys Gln Ile Thr Ala Leu Leu Lys Val Thr Cys Gln Arg
    290                 295                 300

Pro Arg Asp Arg Glu Asn Asp Ile Leu Arg Thr Val Gln His Asn Ala
305                 310                 315                 320

Tyr Asp Gln Asp Pro Tyr Ala Lys Glu Phe Gly Ile Lys Ile Ser Glu
                325                 330                 335

Lys Leu Ala Ser Val Glu Ala Arg Ile Leu Pro Ala Pro Trp Leu Lys
            340                 345                 350

Tyr His Glu Ser Gly Lys Glu Lys Asn Cys Leu Pro Gln Val Gly Gln
        355                 360                 365

Trp Asn Met Met Asn Lys Lys Met Ile Asn Gly Met Thr Val Ser Arg
    370                 375                 380

Trp Ala Cys Ile Asn Phe Ser Arg Ser Val Gln Asp Ser Val Ala Arg
385                 390                 395                 400

Thr Phe Cys Asn Glu Leu Ala Gln Met Cys Gln Val Ser Gly Met Glu
                405                 410                 415

Phe Asn Pro Glu Ser Val Ile Pro Ile Tyr Asn Ala Lys Pro Glu Gln
            420                 425                 430

Val Glu Lys Ala Leu Lys His Val Tyr His Val Ser Gly Ser Lys Ile
        435                 440                 445

Lys Gly Lys Glu Leu Glu Leu Leu Ala Ile Leu Pro Asp Asn Asn
    450                 455                 460

Gly Ser Leu Tyr Gly Asp Leu Lys Arg Ile Cys Glu Thr Asp Leu Gly
465                 470                 475                 480

Leu Ile Ser Gln Cys Cys Leu Thr Lys His Val Phe Lys Ile Thr Lys
                485                 490                 495

Gln Tyr Leu Ala Asn Val Ser Leu Lys Ile Asn Val Lys Met Gly Gly
            500                 505                 510

Arg Asn Thr Val Leu Leu Asp Ala Val Ser Ser Arg Ile Pro Leu Val
        515                 520                 525

Ser Asp Met Pro Thr Ile Ile Phe Gly Ala Asp Val Thr His Pro Glu
    530                 535                 540

Asn Gly Glu Glu Leu Ser Pro Ser Ile Ala Ala Val Val Ala Ser Gln
545                 550                 555                 560

Asp Trp Pro Glu Val Thr Lys Tyr Ala Gly Leu Val Cys Ala Gln Ala
                565                 570                 575

His Arg Gln Glu Leu Ile Gln Asp Leu Tyr Lys Thr Trp Gln Asp Pro
            580                 585                 590

Val Arg Gly Thr Val Ser Gly Gly Met Ile Arg Asp Leu Leu Val Ser
        595                 600                 605

Phe Arg Lys Ala Thr Gly Gln Lys Pro Leu Arg Ile Ile Phe Tyr Arg
    610                 615                 620
```

| Asp | Gly | Val | Ser | Glu | Gly | Gln | Phe | Tyr | Gln | Val | Leu | Leu | Tyr | Glu | Leu |
| --- | --- | --- | --- | --- | --- | --- | --- | --- | --- | --- | --- | --- | --- | --- | --- |
| 625 | | | | 630 | | | | | 635 | | | | | 640 | |

| Asp | Ala | Ile | Arg | Lys | Ala | Cys | Ala | Ser | Leu | Glu | Pro | Asn | Tyr | Gln | Pro |
| --- | --- | --- | --- | --- | --- | --- | --- | --- | --- | --- | --- | --- | --- | --- | --- |
| | | | | 645 | | | | | 650 | | | | | 655 | |

| Pro | Val | Thr | Phe | Ile | Val | Val | Gln | Lys | Arg | His | His | Thr | Arg | Leu | Phe |
| --- | --- | --- | --- | --- | --- | --- | --- | --- | --- | --- | --- | --- | --- | --- | --- |
| | | | 660 | | | | | 665 | | | | | 670 | | |

| Ala | Asn | Asn | Tyr | Arg | Asp | Arg | Ser | Ser | Thr | Asp | Arg | Ser | Gly | Asn | Ile |
| --- | --- | --- | --- | --- | --- | --- | --- | --- | --- | --- | --- | --- | --- | --- | --- |
| | | | 675 | | | | | 680 | | | | | 685 | | |

| Leu | Pro | Gly | Thr | Val | Val | Asp | Thr | Lys | Ile | Cys | His | Pro | Thr | Glu | Phe |
| --- | --- | --- | --- | --- | --- | --- | --- | --- | --- | --- | --- | --- | --- | --- | --- |
| | | 690 | | | | | 695 | | | | | 700 | | | |

| Asp | Phe | Tyr | Leu | Cys | Ser | His | Ala | Gly | Ile | Gln | Gly | Thr | Ser | Arg | Pro |
| --- | --- | --- | --- | --- | --- | --- | --- | --- | --- | --- | --- | --- | --- | --- | --- |
| 705 | | | | 710 | | | | | 715 | | | | | 720 | |

| Ala | His | Tyr | His | Val | Leu | Trp | Asp | Glu | Asn | Asn | Phe | Thr | Pro | Asp | Gly |
| --- | --- | --- | --- | --- | --- | --- | --- | --- | --- | --- | --- | --- | --- | --- | --- |
| | | | | 725 | | | | | 730 | | | | | 735 | |

| Ile | Gln | Ser | Leu | Thr | Asn | Asn | Leu | Cys | Tyr | Thr | Tyr | Ala | Arg | Cys | Thr |
| --- | --- | --- | --- | --- | --- | --- | --- | --- | --- | --- | --- | --- | --- | --- | --- |
| | | | 740 | | | | | 745 | | | | | 750 | | |

| Arg | Ser | Val | Ser | Val | Val | Pro | Pro | Ala | Tyr | Tyr | Ala | His | Leu | Ala | Ala |
| --- | --- | --- | --- | --- | --- | --- | --- | --- | --- | --- | --- | --- | --- | --- | --- |
| | | | 755 | | | | | 760 | | | | | 765 | | |

| Phe | Arg | Ala | Arg | Phe | Tyr | Met | Glu | Pro | Asp | Met | Gln | Asp | Asn | Gly | Ser |
| --- | --- | --- | --- | --- | --- | --- | --- | --- | --- | --- | --- | --- | --- | --- | --- |
| 770 | | | | | 775 | | | | | 780 | | | | | |

| Ala | Gly | Asp | Gly | Asn | Gly | His | Gly | Ala | Lys | Ala | Thr | Arg | Ala | Ala | Gly |
| --- | --- | --- | --- | --- | --- | --- | --- | --- | --- | --- | --- | --- | --- | --- | --- |
| 785 | | | | 790 | | | | | 795 | | | | | 800 | |

| Asp | Tyr | Ser | Val | Lys | Pro | Leu | Pro | Asp | Leu | Lys | Glu | Asn | Val | Lys | Arg |
| --- | --- | --- | --- | --- | --- | --- | --- | --- | --- | --- | --- | --- | --- | --- | --- |
| | | | | 805 | | | | | 810 | | | | | 815 | |

| Val | Met | Phe | Tyr | Cys |
| --- | --- | --- | --- | --- |
| | | | | 820 |

<210> SEQ ID NO 5
<211> LENGTH: 1501
<212> TYPE: DNA
<213> ORGANISM: Glycine max

<400> SEQUENCE: 5

```
gttttgccaa cagttagttc aaatatgcca aatctcaggc atggaattta gtcaagaccc      60
tgtgattcca atatattcag caaaacctga tctggtaaag aaagccttga agtatgtaca     120
ttctgctgta cttgataaac ttggtgggaa agaactagag ttgttgattg ccattcttcc     180
agacaacaat ggctctctgt atggcgatct caaaagaatc tgtgaaaccg atctgggggtt    240
gatttctcag tgctgtctta caaaacacgt attcaagatc aataggcagt atttggcaaa     300
tgtggcacta aagatcaatg tcaagatggg aggaaggaac acagtacttt tggatgccct     360
aagttggagg atcccattgg ttagtgacat tccaacaata attttttggag cagatgtaac    420
acatccagaa tctggagagg acccttgtcc atccattgct gctgttgtag cctcccagga     480
ctggccggaa gtaacaaagt acgcaggatt ggtatgcgct cagcctcatc gtgaggaact     540
cattcaagat cttttttaaat gttggaagga tcctcatcat ggtatagttt atggtggcat    600
gatcagagag ctgttactct cttttaagaa ggcaaccgga caaaaaccat tgaggataat     660
attttacagg gatggggtaa gtgaaggaca gttctaccag gttttgttgt atgagcttga     720
tgccatccgt aaggcttgtg catctttgga acctagttac caacctccgg taacatttgt     780
tgtggttcaa aagcgacatc acactagact cttctcaaac aatcatgacg acagaaatag     840
cactgataag agtgggaata tcttacctgg tactgtggtg gattctaaga tctgtcatcc     900
tacggaattc gacttctatt tatgcagtca tgcgggaatt cagggtacaa gtagaccagc     960
```

-continued

```
tcattatcat gttctgtggg acgagaacaa tttcactgct gatgagatcc aatctctgac    1020
caacaacttg tgctacacct atgcaagatg tacacgatca gtttctgtag tgcctcctgc    1080
gtactatgct catttggcag cttacagagc tcgattctac atggaaccta atgtccatga    1140
aattgctaaa tctcgaggtg caaggtcaaa agatgagtca gttcggccac tacctgctct    1200
gaaagagaag gtgaagaatg taatgtttta ttgttgaatg agacaaaata gagagacatc    1260
taagtagaga aacagcagca tatgtaggaa aaggaaatta aattagcaga gctcagaaag    1320
ctcaatatgt acaacctaac gtgttcataa ttcataattc tccgcatgga aaatttttgac    1380 aaagtctagg ttgttttttca gtatttctag tgcttaggga aggtaataac ttatgtagaa    1440
attatttgtg tatcggtttt cgagcttcaa gacaaaaaaa aaaaaaaaaa aaaaaaaaa    1500 a    1501
```

<210> SEQ ID NO 6
<211> LENGTH: 411
<212> TYPE: PRT
<213> ORGANISM: Glycine max

<400> SEQUENCE: 6

```
Phe Cys Gln Gln Leu Val Gln Ile Cys Gln Ile Ser Gly Met Glu Phe
 1               5                  10                  15

Ser Gln Asp Pro Val Ile Pro Ile Tyr Ser Ala Lys Pro Asp Leu Val
            20                  25                  30

Lys Lys Ala Leu Lys Tyr Val His Ser Ala Val Leu Asp Lys Leu Gly
        35                  40                  45

Gly Lys Glu Leu Glu Leu Ile Ala Ile Leu Pro Asp Asn Asn Gly
    50                  55                  60

Ser Leu Tyr Gly Asp Leu Lys Arg Ile Cys Glu Thr Asp Leu Gly Leu
65                  70                  75                  80

Ile Ser Gln Cys Cys Leu Thr Lys His Val Phe Lys Ile Asn Arg Gln
                85                  90                  95

Tyr Leu Ala Asn Val Ala Leu Lys Ile Asn Val Lys Met Gly Gly Arg
            100                 105                 110

Asn Thr Val Leu Leu Asp Ala Leu Ser Trp Arg Ile Pro Leu Val Ser
        115                 120                 125

Asp Ile Pro Thr Ile Ile Phe Gly Ala Asp Val Thr His Pro Glu Ser
    130                 135                 140

Gly Glu Asp Pro Cys Pro Ser Ile Ala Ala Val Val Ala Ser Gln Asp
145                 150                 155                 160

Trp Pro Glu Val Thr Lys Tyr Ala Gly Leu Val Cys Ala Gln Pro His
                165                 170                 175

Arg Glu Glu Leu Ile Gln Asp Leu Phe Lys Cys Trp Lys Asp Pro His
            180                 185                 190

His Gly Ile Val Tyr Gly Gly Met Ile Arg Glu Leu Leu Ser Phe
        195                 200                 205

Lys Lys Ala Thr Gly Gln Lys Pro Leu Arg Ile Ile Phe Tyr Arg Asp
    210                 215                 220

Gly Val Ser Glu Gly Gln Phe Tyr Gln Val Leu Leu Tyr Glu Leu Asp
225                 230                 235                 240

Ala Ile Arg Lys Ala Cys Ala Ser Leu Glu Pro Ser Tyr Gln Pro Pro
                245                 250                 255

Val Thr Phe Val Val Val Gln Lys Arg His His Thr Arg Leu Phe Ser
            260                 265                 270
```

```
Asn Asn His Asp Asp Arg Asn Ser Thr Asp Lys Ser Gly Asn Ile Leu
            275                 280                 285

Pro Gly Thr Val Val Asp Ser Lys Ile Cys His Pro Thr Glu Phe Asp
    290                 295                 300

Phe Tyr Leu Cys Ser His Ala Gly Ile Gln Gly Thr Ser Arg Pro Ala
305                 310                 315                 320

His Tyr His Val Leu Trp Asp Glu Asn Asn Phe Thr Ala Asp Glu Ile
                325                 330                 335

Gln Ser Leu Thr Asn Asn Leu Cys Tyr Thr Tyr Ala Arg Cys Thr Arg
            340                 345                 350

Ser Val Ser Val Val Pro Pro Ala Tyr Tyr Ala His Leu Ala Ala Tyr
            355                 360                 365

Arg Ala Arg Phe Tyr Met Glu Pro Asn Val His Glu Ile Ala Lys Ser
    370                 375                 380

Arg Gly Ala Arg Ser Lys Asp Glu Ser Val Arg Pro Leu Pro Ala Leu
385                 390                 395                 400

Lys Glu Lys Val Lys Asn Val Met Phe Tyr Cys
            405                 410

<210> SEQ ID NO 7
<211> LENGTH: 3096
<212> TYPE: DNA
<213> ORGANISM: Zea mays

<400> SEQUENCE: 7
gtttcggtgg ggttcttgcc gctgcggttg ttcgtgcggc gcggatttag ggagggttct      60
gaggcgaggg cttttgcccc cctcgagcga tttgcagctt tgggtccgat acagtgctca     120
tcaaggctca ctaaatggag tctcacaatg gcgaggccaa tgacttgcct ccaccacctc     180
ctctgattgc tggtgttgaa ccacttaaag ctgatgaaac aaagatgcca ttgaaaccta     240
ggagtctggt ccagagaaat ggatttggca gaaaggggca gccaataaag ctgataacaa     300
atcacttcaa agtttctctt gtgaatgctg aagaattttt ctaccattac tatgtcaatt     360
tgaagtatga agatgataca ccggttgatc gcaaagggtc aggaaggaaa gtgattgaaa     420
aactgcagca aacttatgct gctgaacttg caaataaaga ttttgcctat gatggtgaga     480
agagcctgtt cacaattggt gctcttcctc aagttaaaaa tgagtttact gtcgtggttg     540
aagatttttc aactggaaag actcctgcaa acggcagtcc aggaaatgac agtcctcccg     600
gaagtgacag gaaagggtc agaaggcctt acaatacaaa gacctataag gtcgagctct     660
cttttgcagc aaaaattcct atgagtgcaa tctcacaggc cttaagaggt caggaatcag     720
agcacactca ggaagcaatt cgagtgattg acattattct gaggcagcac tcagctaagc     780
agggttgcct attagtaagg caatcattct tccacaacaa tccttccaat tttgttgacc     840
tgggtggtgg tgtagtgggc tgtagaggtt ttcattctag ttttcgagca cccagagtg     900 gactttcact caatatcgat gtgtcgacta caatgatagt gaaacctggt cctgtcattg     960
attttctgct tgacaatcag aaagttggtg attcaagcat gattgattgg ctaagggca    1020 agcgtgcact gaagaacttg aggataaaaa taagtccagc gaaccaagaa cagaagattg    1080
ttggtctcag cgaaagaact tgtcgtgagc aattattcac actgaaacat aaaaatggta    1140
acaatggtga ctctgaagag atcactgttt atgattactt cgtaaagcag cgtggcatag    1200
tgctgcaata ctctggtgat cttccttgca tcaatgtggg aaaactaaag cggccaacat    1260
attttccaat tgagttatgc agtcttgtgc ctttacaaag atacactaaa gctttgaaca    1320
```

| | |
|---|---|
| cacttcagag gtcatcactc gtggagaaat ctaggcagaa accgcaggaa aggatgtctg | 1380 |
| ttttatctga tgtgctgcaa agaagcaact atgatgcaga gcccatgttg aaggcatgcg | 1440 |
| ggattacaat tgctagaaat tcacagaaag ttgatggtag ggtattgcag ccacctaagc | 1500 |
| ttaaagctgg gaatggtgaa gacattttta cacgcaatgg tagatggaac ttcaacaata | 1560 |
| agaggctcat tagagcttgt agtgtcgaga atgggcggt ggtaaacttt tctgcacgat | 1620 |
| gcaatgtcag ggatcttgtc cgggatctca tcaagtgtgg aggcatgaag ggcattatgg | 1680 |
| ttgatgctcc ttttgctgta tttgatgaga atccttcaat gagacggtca cctgctataa | 1740 |
| gaagggttga agacatgttt gaacaagtga aaactaagct tcctggagca ccaaagtttc | 1800 |
| ttttgtgtgt tctagctgaa aggaagaatt ctgatattta tgggccttgg aagaagaaat | 1860 |
| gccttgctga atttgggatc gttacacaat gtgtggcacc aactagagtg aacgaccagt | 1920 |
| atcttacaaa tgtcctactt aagataaatg caaagctggg tggcatgaat tcgttgctcc | 1980 |
| aaattgaaac atccccagca attcctcttg tatccaaggt cccaactata atcttgggaa | 2040 |
| tggatgtgtc acacggttct cctggacatt ctgatgtacc atctattgct gctgttgtta | 2100 |
| gttctcgtga atggcctctt atctcgaaat acagagcttc tgtccgcacc caatcaccta | 2160 |
| aaatggaaat gattgactca ttgtttaagc cacgggaagc tgaagatgat ggtctgatcc | 2220 |
| gggagtgtct gattgacttc tacaccagtt ctgggaagag aaagcctgac caagttatca | 2280 |
| tattcaggga cggtgttagc gaaagtcagt ttaatcaggt gctgaacatt gagttgcaac | 2340 |
| aaatcatcga ggcttgcaaa tttcttgatg agaaatggaa tcccaagttc acgttgatta | 2400 |
| ttgcccagaa gaatcatcac actaaatttt tcattcctgg aaagccagat aatgtcccac | 2460 |
| caggaactgt ggtggacaac aaagtctgcc atccaaagaa cttcgatttc tacatgtgtg | 2520 |
| cgcatgctgg aatgatcggg actacgaggc caactcacta ccacatcctg catgatgaga | 2580 |
| taggcttcag tcctgatgat ctgcaggagc tggtgcattc gctctcttat gtgtaccaaa | 2640 |
| ggagcacaac agccatatca gtcgttgctc ccatctgcta cgcacatctg gcagctgctc | 2700 |
| aggttggcca gttcataaag ttcgatgaga tgtcggagac gtcctccagt catggcgggc | 2760 |
| atacttcggc gggcagcgtt ccggtccagg agctgccgcg cctgcatgag aaagtgagga | 2820 |
| gctcgatgtt cttttgctga gccgtggttt tactttttg gtggatggtg aacccctcta | 2880 |
| gttatgtcgg tagacgctct tggatgacgc tctagttgtg gtccaggaag gctcgagctg | 2940 |
| gtacgatgtt aaatgttagt ttttaagcg tcgctgcggc tatgttggtg cctcaggaag | 3000 |
| acttggaacc tggttaggat gtcgttaaat ctacccctta tcgttcctgg ttaaaaaaaa | 3060 |
| aaaaaaaaaa aaaaaaaaaa aaaaaaaaaa aaaaaa | 3096 |

<210> SEQ ID NO 8
<211> LENGTH: 901
<212> TYPE: PRT
<213> ORGANISM: Zea mays

<400> SEQUENCE: 8

Met Glu Ser His Asn Gly Glu Ala Asn Asp Leu Pro Pro Pro Pro Pro
1               5                   10                  15

Leu Ile Ala Gly Val Glu Pro Leu Lys Ala Asp Glu Thr Lys Met Pro
            20                  25                  30

Leu Lys Pro Arg Ser Leu Val Gln Arg Asn Gly Phe Gly Arg Lys Gly
        35                  40                  45

Gln Pro Ile Lys Leu Ile Thr Asn His Phe Lys Val Ser Leu Val Asn
    50                  55                  60

```
Ala Glu Glu Phe Phe Tyr His Tyr Tyr Val Asn Leu Lys Tyr Glu Asp
 65                  70                  75                  80

Asp Thr Pro Val Asp Arg Lys Gly Ser Gly Arg Lys Val Ile Glu Lys
                 85                  90                  95

Leu Gln Gln Thr Tyr Ala Ala Glu Leu Ala Asn Lys Asp Phe Ala Tyr
                100                 105                 110

Asp Gly Glu Lys Ser Leu Phe Thr Ile Gly Ala Leu Pro Gln Val Lys
                115                 120                 125

Asn Glu Phe Thr Val Val Glu Asp Phe Ser Thr Gly Lys Thr Pro
130                 135                 140

Ala Asn Gly Ser Pro Gly Asn Asp Ser Pro Gly Ser Asp Arg Lys
145                 150                 155                 160

Arg Val Arg Arg Pro Tyr Asn Thr Lys Thr Tyr Lys Val Glu Leu Ser
                165                 170                 175

Phe Ala Ala Lys Ile Pro Met Ser Ala Ile Ser Gln Ala Leu Arg Gly
                180                 185                 190

Gln Glu Ser Glu His Thr Gln Glu Ala Ile Arg Val Ile Asp Ile Ile
                195                 200                 205

Leu Arg Gln His Ser Ala Lys Gln Gly Cys Leu Leu Val Arg Gln Ser
210                 215                 220

Phe Phe His Asn Asn Pro Ser Asn Phe Val Asp Leu Gly Gly Gly Val
225                 230                 235                 240

Val Gly Cys Arg Gly Phe His Ser Ser Phe Arg Ala Thr Gln Ser Gly
                245                 250                 255

Leu Ser Leu Asn Ile Asp Val Ser Thr Thr Met Ile Val Lys Pro Gly
                260                 265                 270

Pro Val Ile Asp Phe Leu Leu Asp Asn Gln Lys Val Gly Asp Ser Ser
                275                 280                 285

Met Ile Asp Trp Ala Lys Gly Lys Arg Ala Leu Lys Asn Leu Arg Ile
290                 295                 300

Lys Ile Ser Pro Ala Asn Gln Glu Gln Lys Ile Val Gly Leu Ser Glu
305                 310                 315                 320

Arg Thr Cys Arg Glu Gln Leu Phe Thr Leu Lys His Lys Asn Gly Asn
                325                 330                 335

Asn Gly Asp Ser Glu Glu Ile Thr Val Tyr Asp Tyr Phe Val Lys Gln
                340                 345                 350

Arg Gly Ile Val Leu Gln Tyr Ser Gly Asp Leu Pro Cys Ile Asn Val
                355                 360                 365

Gly Lys Leu Lys Arg Pro Thr Tyr Phe Pro Ile Glu Leu Cys Ser Leu
                370                 375                 380

Val Pro Leu Gln Arg Tyr Thr Lys Ala Leu Asn Thr Leu Gln Arg Ser
385                 390                 395                 400

Ser Leu Val Glu Lys Ser Arg Gln Lys Pro Gln Glu Arg Met Ser Val
                405                 410                 415

Leu Ser Asp Val Leu Gln Arg Ser Asn Tyr Asp Ala Glu Pro Met Leu
                420                 425                 430

Lys Ala Cys Gly Ile Thr Ile Ala Arg Asn Phe Thr Glu Val Asp Gly
                435                 440                 445

Arg Val Leu Gln Pro Pro Lys Leu Lys Ala Gly Asn Gly Glu Asp Ile
                450                 455                 460

Phe Thr Arg Asn Gly Arg Trp Asn Phe Asn Asn Lys Arg Leu Ile Arg
465                 470                 475                 480
```

-continued

```
Ala Cys Ser Val Glu Lys Trp Ala Val Val Asn Phe Ser Ala Arg Cys
                485                 490                 495

Asn Val Arg Asp Leu Val Arg Asp Leu Ile Lys Cys Gly Gly Met Lys
            500                 505                 510

Gly Ile Met Val Asp Ala Pro Phe Ala Val Phe Asp Glu Asn Pro Ser
            515                 520                 525

Met Arg Arg Ser Pro Ala Ile Arg Arg Val Glu Asp Met Phe Glu Gln
            530                 535                 540

Val Lys Thr Lys Leu Pro Gly Ala Pro Lys Phe Leu Leu Cys Val Leu
545                 550                 555                 560

Ala Glu Arg Lys Asn Ser Asp Ile Tyr Gly Pro Trp Lys Lys Lys Cys
                565                 570                 575

Leu Ala Glu Phe Gly Ile Val Thr Gln Cys Val Ala Pro Thr Arg Val
            580                 585                 590

Asn Asp Gln Tyr Leu Thr Asn Val Leu Leu Lys Ile Asn Ala Lys Leu
            595                 600                 605

Gly Gly Met Asn Ser Leu Leu Gln Ile Glu Thr Ser Pro Ala Ile Pro
610                 615                 620

Leu Val Ser Lys Val Pro Thr Ile Ile Leu Gly Met Asp Val Ser His
625                 630                 635                 640

Gly Ser Pro Gly His Ser Asp Val Pro Ser Ile Ala Ala Val Val Ser
                645                 650                 655

Ser Arg Glu Trp Pro Leu Ile Ser Lys Tyr Arg Ala Ser Val Arg Thr
                660                 665                 670

Gln Ser Pro Lys Met Glu Met Ile Asp Ser Leu Phe Lys Pro Arg Glu
            675                 680                 685

Ala Glu Asp Asp Gly Leu Ile Arg Glu Cys Leu Ile Asp Phe Tyr Thr
            690                 695                 700

Ser Ser Gly Lys Arg Lys Pro Asp Gln Val Ile Ile Phe Arg Asp Gly
705                 710                 715                 720

Val Ser Glu Ser Gln Phe Asn Gln Val Leu Asn Ile Glu Leu Gln Gln
                725                 730                 735

Ile Ile Glu Ala Cys Lys Phe Leu Asp Glu Lys Trp Asn Pro Lys Phe
            740                 745                 750

Thr Leu Ile Ile Ala Gln Lys Asn His His Thr Lys Phe Phe Ile Pro
            755                 760                 765

Gly Lys Pro Asp Asn Val Pro Pro Gly Thr Val Val Asp Asn Lys Val
            770                 775                 780

Cys His Pro Lys Asn Phe Asp Phe Tyr Met Cys Ala His Ala Gly Met
785                 790                 795                 800

Ile Gly Thr Thr Arg Pro Thr His Tyr His Ile Leu His Asp Glu Ile
                805                 810                 815

Gly Phe Ser Pro Asp Asp Leu Gln Glu Leu Val His Ser Leu Ser Tyr
            820                 825                 830

Val Tyr Gln Arg Ser Thr Thr Ala Ile Ser Val Val Ala Pro Ile Cys
            835                 840                 845

Tyr Ala His Leu Ala Ala Ala Gln Val Gly Gln Phe Ile Lys Phe Asp
850                 855                 860

Glu Met Ser Glu Thr Ser Ser Ser His Gly Gly His Thr Ser Ala Gly
865                 870                 875                 880

Ser Val Pro Val Gln Glu Leu Pro Arg Leu His Glu Lys Val Arg Ser
                885                 890                 895

Ser Met Phe Phe Cys
```

900

<210> SEQ ID NO 9
<211> LENGTH: 2446
<212> TYPE: DNA
<213> ORGANISM: Zea mays

<400> SEQUENCE: 9

```
gcacgagatc aaatttgctg ctcgcgctga tctccaccat ttggctatgt ttcttgctgg      60
gaggcagcca gatgcccctc aagaggctct tcaagtactt gacatcgtgc tacgtgaaat     120
gcctactgcc aagtattgtc ctgttggtag atcattttat tctcccaagt tagggagacc     180
tcagcaactt ggtgaaggtt tggaaacttg gcgtggtttc taccaaagca taaggcccac     240
acagatgggt ctttctctga atattgatat gtcctctact gcattttttg aggccctccc     300
tgtaattgat tttgtttctc agcttcttaa tagagatatc tcagttagac cattgtctga     360
ttctgatcgc gtgaagatta aaaaagcct acgaggtgtg aaagtggagg tcacacaccg     420
tggaaacatg cgtaggaaat atcggatatc tggcctact ccacaagcaa caagggagtt     480
atcattccct attgatgatc gtggtactgt taagactgtg gtgcaatact tcctggagac     540
ttatggtttc agtattcagc acaccacttt accttgtttg caagtgggca atcagcaaag     600
accaaattat ctgcctatgg aggtctgtaa gatagttgag gggcagcgct actcaaaacg     660
acttaatgat aaacagatca ctgctctact gaaggtgact tgccaacgtc cccaagcgcg     720
tgagaaggac atcttggaga ctgtgtatca caatgcctac tccaaggatc cttatgccca     780
ggaatttggt ataacgattg atgagcgtct tgcatcggtt gaagctcgtg ttctgcctcc     840
cccaaggctg aaataccatg atagtggcag agaaagggat gtattgccaa agttggcca     900
gtggaacatg atgaataaga aaatggtcaa tggtggtaga gttagcagct gggcatgcat     960
taacttctca cggaatgtgc aagatggtgc tgccgggggt ttctgtcatg aattggcttt    1020
gatgtgccaa gtatcaggaa tggattttgt acttgaacct gtgctgtcac cttgctatgc    1080
aaggcctgaa cttgttgaaa gagcactaaa gggacgctat caagatgcga tgaacatact    1140
cgggcctcag gccgagaac tcgacttgct gattgttata ctgcctgaca ataatggttc    1200
tctttacggg gatgtcaaaa ggatctgtga gactaatctt ggattggtct cccaatgctg    1260
tctgactaaa catgttttca aggtgaacaa gcagcagtat cttgcaaatg ttgccctgaa    1320
aataaatgtg aaggttgggg gaaggaatac tgtgcttgtt gatgctttgg caaggagaat    1380
ccccttgtc agtgacatag cgactattat ctttggtgct gatgtgaccc atccccatcc    1440
tggggaagat tctagtcctt ccattgcagc tgtggttgct tctcaagact ggcctgaggt    1500
tacaaagtat gcaggattgg tgagtgctca agcccatcgt caagaattga tacaggatct    1560
tttcaaggta tggcaagatc ccgaaagggg gactgtctct ggtggcatga tcagggagct    1620
tctcatatct ttctggaggg caactggaca gaaaccaaag aggatcatat tctacaggga    1680
tggcgtcagt gagggacaat tctaccaagt tctgttgtat gaacttgatg ccattagaaa    1740
ggcctgtgcg tcattggagt ctgactacca gcctccagtt acttttgtcg tggtccagaa    1800
gcgtcatcac accaggttgt ttgctaataa tcacaatgat aatcgtgctg tcgataaaag    1860
cgggaacata ctgcctggca ccgtggtgga ctcgaagatc tgccatccaa ctgagtttga    1920
tttctacctg tgcagccatg ctggcattca gggaacaagc cgccctgccc attaccatgt    1980
tctgtgggat gagaacaact ttacggctga tgggttgcaa actctcacca acaacttgtg    2040
ttacacgtat gctaggtgca cacgctcagt atcgattgtt cctcctgcat actatgctca    2100
```

-continued

```
cctggcagcc ttccgagctc ggttctacat ggagccagat acgagtgaca gtggatctat    2160
ggcaagccgt ggccctccac caggggggcg caacaccaag gctgccggtg ttgggaatgt    2220
tgctgtgagg ccattacctg ccctcaagga aaacgtgaag cgggtcatgt tctactgcta    2280
agactgatgc tgttaaggca gagctacctt ttattattac agtatatcgt gaagactaga    2340
gtattttttt ccacgtactt gatgatgctg agctaccttt taaaaaaaaa aaaaaaaaa     2400 aaaaaaaaa aaaaaaaaa aaaaaaaaa aaaaaaaaa aaaaa                        2446
```

<210> SEQ ID NO 10
<211> LENGTH: 757
<212> TYPE: PRT
<213> ORGANISM: Zea mays

<400> SEQUENCE: 10

```
Ile Lys Phe Ala Ala Arg Ala Asp Leu His His Leu Ala Met Phe Leu
 1               5                  10                  15

Ala Gly Arg Gln Pro Asp Ala Pro Gln Glu Ala Leu Gln Val Leu Asp
            20                  25                  30

Ile Val Leu Arg Glu Met Pro Thr Ala Lys Tyr Cys Pro Val Gly Arg
        35                  40                  45

Ser Phe Tyr Ser Pro Lys Leu Gly Arg Pro Gln Gln Leu Gly Glu Gly
    50                  55                  60

Leu Glu Thr Trp Arg Gly Phe Tyr Gln Ser Ile Arg Pro Thr Gln Met
65                  70                  75                  80

Gly Leu Ser Leu Asn Ile Asp Met Ser Ser Thr Ala Phe Phe Glu Ala
                85                  90                  95

Leu Pro Val Ile Asp Phe Val Ser Gln Leu Leu Asn Arg Asp Ile Ser
           100                 105                 110

Val Arg Pro Leu Ser Asp Ser Asp Arg Val Lys Ile Lys Lys Ala Leu
       115                 120                 125

Arg Gly Val Lys Val Glu Val Thr His Arg Gly Asn Met Arg Arg Lys
   130                 135                 140

Tyr Arg Ile Ser Gly Leu Thr Pro Gln Ala Thr Arg Glu Leu Ser Phe
145                 150                 155                 160

Pro Ile Asp Asp Arg Gly Thr Val Lys Thr Val Gln Tyr Phe Leu
                165                 170                 175

Glu Thr Tyr Gly Phe Ser Ile Gln His Thr Thr Leu Pro Cys Leu Gln
           180                 185                 190

Val Gly Asn Gln Gln Arg Pro Asn Tyr Leu Pro Met Glu Val Cys Lys
       195                 200                 205

Ile Val Glu Gly Gln Arg Tyr Ser Lys Arg Leu Asn Asp Lys Gln Ile
   210                 215                 220

Thr Ala Leu Leu Lys Val Thr Cys Gln Arg Pro Gln Ala Arg Glu Lys
225                 230                 235                 240

Asp Ile Leu Glu Thr Val Tyr His Asn Ala Tyr Ser Lys Asp Pro Tyr
                245                 250                 255

Ala Gln Glu Phe Gly Ile Thr Ile Asp Glu Arg Leu Ala Ser Val Glu
           260                 265                 270

Ala Arg Val Leu Pro Pro Arg Leu Lys Tyr His Asp Ser Gly Arg
       275                 280                 285

Glu Arg Asp Val Leu Pro Lys Val Gly Gln Trp Asn Met Met Asn Lys
   290                 295                 300

Lys Met Val Asn Gly Gly Arg Val Ser Ser Trp Ala Cys Ile Asn Phe
```

```
           305                 310                 315                 320
Ser Arg Asn Val Gln Asp Gly Ala Ala Gly Gly Phe Cys His Glu Leu
                    325                 330                 335

Ala Leu Met Cys Gln Val Ser Gly Met Asp Phe Val Leu Glu Pro Val
                    340                 345                 350

Leu Ser Pro Cys Tyr Ala Arg Pro Glu Leu Val Glu Arg Ala Leu Lys
                    355                 360                 365

Gly Arg Tyr Gln Asp Ala Met Asn Ile Leu Gly Pro Gln Gly Arg Glu
                    370                 375                 380

Leu Asp Leu Leu Ile Val Ile Leu Pro Asp Asn Asn Gly Ser Leu Tyr
385                 390                 395                 400

Gly Asp Val Lys Arg Ile Cys Glu Thr Asn Leu Gly Leu Val Ser Gln
                    405                 410                 415

Cys Cys Leu Thr Lys His Val Phe Lys Val Asn Lys Gln Gln Tyr Leu
                    420                 425                 430

Ala Asn Val Ala Leu Lys Ile Asn Val Lys Val Gly Gly Arg Asn Thr
                    435                 440                 445

Val Leu Val Asp Ala Leu Ala Arg Arg Ile Pro Leu Val Ser Asp Ile
                    450                 455                 460

Ala Thr Ile Ile Phe Gly Ala Asp Val Thr His Pro His Pro Gly Glu
465                 470                 475                 480

Asp Ser Ser Pro Ser Ile Ala Ala Val Val Ala Ser Gln Asp Trp Pro
                    485                 490                 495

Glu Val Thr Lys Tyr Ala Gly Leu Val Ser Ala Gln Ala His Arg Gln
                    500                 505                 510

Glu Leu Ile Gln Asp Leu Phe Lys Val Trp Gln Asp Pro Glu Arg Gly
                    515                 520                 525

Thr Val Ser Gly Gly Met Ile Arg Glu Leu Leu Ile Ser Phe Trp Arg
                    530                 535                 540

Ala Thr Gly Gln Lys Pro Lys Arg Ile Ile Phe Tyr Arg Asp Gly Val
545                 550                 555                 560

Ser Glu Gly Gln Phe Tyr Gln Val Leu Leu Tyr Glu Leu Asp Ala Ile
                    565                 570                 575

Arg Lys Ala Cys Ala Ser Leu Glu Ser Asp Tyr Gln Pro Pro Val Thr
                    580                 585                 590

Phe Val Val Val Gln Lys Arg His His Thr Arg Leu Phe Ala Asn Asn
                    595                 600                 605

His Asn Asp Asn Arg Ala Val Asp Lys Ser Gly Asn Ile Leu Pro Gly
                    610                 615                 620

Thr Val Val Asp Ser Lys Ile Cys His Pro Thr Glu Phe Asp Phe Tyr
625                 630                 635                 640

Leu Cys Ser His Ala Gly Ile Gln Gly Thr Ser Arg Pro Ala His Tyr
                    645                 650                 655

His Val Leu Trp Asp Glu Asn Asn Phe Thr Ala Asp Gly Leu Gln Thr
                    660                 665                 670

Leu Thr Asn Asn Leu Cys Tyr Thr Tyr Ala Arg Cys Thr Arg Ser Val
                    675                 680                 685

Ser Ile Val Pro Pro Ala Tyr Tyr Ala His Leu Ala Ala Phe Arg Ala
                    690                 695                 700

Arg Phe Tyr Met Glu Pro Asp Thr Ser Asp Ser Gly Ser Met Ala Ser
705                 710                 715                 720

Arg Gly Pro Pro Pro Gly Gly Arg Asn Thr Lys Ala Ala Gly Val Gly
                    725                 730                 735
```

Asn Val Ala Val Arg Pro Leu Pro Ala Leu Lys Glu Asn Val Lys Arg
            740                 745                 750

Val Met Phe Tyr Cys
        755

<210> SEQ ID NO 11
<211> LENGTH: 3808
<212> TYPE: DNA
<213> ORGANISM: Zea mays

<400> SEQUENCE: 11

| | | | | | |
|---|---|---|---|---|---|
| ctgctttctc | cagtgagccg | caccgcact | accgctgacg | ctaattaacc | acaagcgacc | 60 |
| gtcgccttcc | cccacctcct | cccttcctca | aaaaaaggcg | gaggcgggag | tggtggtggt | 120 |
| gctcgtgggc | acgcagcgga | gcaccctgta | cagcagcagc | gctgcggcag | tagagagtgc | 180 |
| cattggtgga | gctggtaact | agccctcccc | cctccgttcc | cgtcccgcgc | gcagccgtct | 240 |
| gccgagcctg | ctcagtgccc | atcatggtga | ggaagaagag | aactggccct | ggtggctctg | 300 |
| gagaaacttc | tggagagtct | tcaggagcct | ctggacaagg | ttcctcacag | cagcctgagc | 360 |
| gaactcaaca | acctggggga | ggacgtggct | gggtgcctca | acagggtggc | catggtggtg | 420 |
| ggcaacacca | gggtcgtgat | cgacattatc | agggacgtgg | aggaccaggg | ccacatcacc | 480 |
| ttggtagtgg | ggcacctgag | tatcacccgc | gtgaatacca | gggacgtggt | ggtgaatatc | 540 |
| agggacatgg | tggtgagtac | cagggacggg | gtggtgacta | ccagggacgt | ggtggtggcc | 600 |
| gctccagagg | tggaatgcca | cagccatact | atggtgggca | tagggaggt | aatgttggac | 660 |
| gcaatgttcc | tccaggtccg | tccaggacag | ttcccgagct | gcaccaagcc | ccatatgtcc | 720 |
| agtatccagc | cccggtggtt | tcgccctccc | catcgggacc | tggctcatcc | tcacagccta | 780 |
| tggcagaggt | gagctctgga | caagtccagc | aacagtttca | gcaacttgcc | gatcgtggtc | 840 |
| agagttccac | gagccaagaa | attcaagtgg | caccagcatc | aagcaaatcg | gttcgattcc | 900 |
| cgttacggcc | cggcaagggc | acttatgggg | acaggtgcat | tgtgaaggca | aatcattttt | 960 |
| ttgctgagct | tcctgacaaa | gaccttcacc | aatatgatgt | atctataaca | cctgaggtta | 1020 |
| cttcacgtgg | cgtcaatcgt | gctgtcatgg | gtgagcttgt | aacaatatat | agacaatccc | 1080 |
| atttgggtgg | gcgtctacct | gcatacgatg | aagaaagag | cctgtatact | gctggaccat | 1140 |
| tgccatttac | ttctatggca | tttgaaatta | ccttgcaaga | tgaggaagat | agtcttggcg | 1200 |
| gtcgccaagg | tggacatagg | cgtgagagag | tatttagggt | ggtgatcaaa | tttgcagccc | 1260 |
| gtgctgatct | ccaccatctg | gctatgtttc | tagctggaag | gcaagcagat | gcccctcagg | 1320 |
| aagctcttca | agtgcttgac | attgtactac | gtgaattgcc | taccgcgagg | tattctcctg | 1380 |
| tcggtaggtc | attttactct | cccaacttag | ggagacgtca | aaaacttggt | gagggattgg | 1440 |
| aaagttggcg | tggttttac | caaagcataa | ggccgacaca | gatgggcctt | tcactgaata | 1500 |
| ttgatatgtc | ctctactgca | tttatcgagc | ctctccctgt | gatcgatttt | gttgctcagc | 1560 |
| ttccttaacag | agatatctca | gttaggccat | tgtctgattc | tgatcgcgtg | aagattaaaa | 1620 |
| aagccctaag | aggtgtgaag | gttgaggtga | ctcacagggg | aaacatgcgc | agaaaatatc | 1680 |
| gcatttctgg | cctcacctca | caagcaacaa | gagagctatc | attccctgtt | gatgatcgtg | 1740 |
| gtactgtgaa | gactgtggtg | caatacttca | tggagactta | tggttttagt | atccagcaca | 1800 |
| ccactttacc | atgcttgcaa | gtgggtaatc | aacaaagacc | aaattatctg | cctatggagg | 1860 |
| tttgcaagat | agttgaagga | cagcgttact | caaagcgact | caatgagaaa | caaatcactg | 1920 |

```
ctctactgaa agtgacctgc cagcgccctc aagagcgcga gctggacatc ttacagactg    1980
tgcatcacaa tgcatactat gaagacccct atgcactgga atttggtata agaattgatg    2040
aacgtcttgc tgcagttgaa gctcgtgttc tgccaccacc aagacttaaa taccatgata    2100
gtggccgaga gaaggatgtt ttgcccagag ttggccaatg aacatgatg aataagaaaa     2160 tggttaatgg tggcagagtg agcaactggg catgtattaa cttctctcgg aatgtgcaag    2220
atagtgccgc tagggttttc tctcatgagt tggcagtcat gtgccaaata tcaggaatgg    2280
attttgctct tgagcctgtg ctgcctccag tgactgcaag gccagaacat gttgagagag    2340
cgttaaaggc acgttatcaa gatgcaatga acatactgag gccacaggga agggaacttg    2400
atctgctgat cgtaatactg cctgacaaca atggttctct ttatggggat ctcaaaagga    2460
tctgtgagac tgaactcgga ttggtctccc agtgttgtct gactaaacat gtttttaaga    2520
tgagcaagca gtaccttgca aatgttgcac tcaaaataaa tgttaaggtt ggggaagga    2580 atactgtact tttagatgct ttgtcaagga gaatcccccct tgtcagtgac agaccgacca    2640
taatatttgg tgctgatgtt acccatccac atcctggaga agattccagt ccttccattg    2700
cagccgttgt tgcttcgcaa gactggcccg aggtcacgaa atacgctgga ctagtgagtg    2760
cgcaagccca tcgccaggag ctgatacagg atctttttcaa agtatggcag acccgcaga    2820 gaaggacggt aactggcggc atgataaagg aacttctcat ttcttttcaag agggcaactg    2880 gacagaagcc ccagaggatc atattctaca gggatggtgt cagtgaggga cagttctatc    2940
aagtattgct gtacgaactt gatgccatta gaaaggcctg tgcgtccctg gagcccaact    3000
accagcctcc agttactttt gtcgtggtac agaagcgcca tcacactagg ctgtttgcga    3060
acaaccacag tgatcagcgc acagtcgata gaagcggaaa catactgcct ggcaccgtgg    3120
tcgattcgaa gatttgccat cctactgagt ttgacttcta cctgtgtagc catgctggca    3180
ttcagggaac gagccgccct gctcactacc atgtcctgtg ggacgagaac aagttcacag    3240
ctgacgagct gcagaccctg acgaacaacc tgtgctacac gtacgctagg tgcacccgct    3300
ccgtgtccat cgtgccccg gcgtactacg ctcatctggc agccttccga gctcgcttct    3360
acatggagcc agacacctct gacagcgggt cactggccag cggtgcccgt ggcccccac    3420 ccggtgcggc acgcagcagc acgagagggg ccgggagtgt cgaggtcagg cccctacctg    3480
ctctcaagga gaacgtgaag cgtgtcatgt tttactgctg agacgctggt gggctgcctt    3540
cgccaaggaa aatgccctgg agcattccca tgtacccgca ctgtttcggt gatacagtac    3600
tatctaacgc cgattttgcg cgttaagact tccagtgatc tgggaaattt cttgtacgac    3660
tgttgtagtg ttgtgtattc gtaatgtgat gacgcggcag ttcttctagg agcttagtgc    3720
cgtgtaaaat atctgttgta agttgtaacc tgtcaccctc tagtgttatg tcatgatgaa    3780
ccaaattaaa aaaaaaaaa aaaaaaaa                                        3808
```

<210> SEQ ID NO 12
<211> LENGTH: 1085
<212> TYPE: PRT
<213> ORGANISM: Zea mays

<400> SEQUENCE: 12

```
Met Val Arg Lys Lys Arg Thr Gly Pro Gly Gly Ser Gly Glu Thr Ser
  1               5                  10                  15

Gly Glu Ser Ser Gly Ala Ser Gly Gln Gly Ser Ser Gln Gln Pro Glu
             20                  25                  30

Arg Thr Gln Gln Pro Gly Gly Gly Arg Gly Trp Val Pro Gln Gln Gly
```

```
                 35                  40                  45
Gly His Gly Gly Gly Gln His Gln Gly Arg Asp Arg His Tyr Gln Gly
             50                  55                  60

Arg Gly Gly Pro Gly Pro His His Leu Gly Ser Gly Ala Pro Glu Tyr
 65                  70                  75                  80

His Pro Arg Glu Tyr Gln Gly Arg Gly Gly Glu Tyr Gln Gly His Gly
                 85                  90                  95

Gly Glu Tyr Gln Gly Arg Gly Gly Asp Tyr Gln Gly Arg Gly Gly Gly
                100                 105                 110

Arg Ser Arg Gly Gly Met Pro Gln Pro Tyr Tyr Gly Gly His Arg Gly
            115                 120                 125

Gly Asn Val Gly Arg Asn Val Pro Pro Gly Pro Ser Arg Thr Val Pro
            130                 135                 140

Glu Leu His Gln Ala Pro Tyr Val Gln Tyr Pro Ala Pro Val Val Ser
145                 150                 155                 160

Pro Ser Pro Ser Gly Pro Gly Ser Ser Gln Pro Met Ala Glu Val
                165                 170                 175

Ser Ser Gly Gln Val Gln Gln Phe Gln Gln Leu Ala Asp Arg Gly
            180                 185                 190

Gln Ser Thr Ser Gln Glu Ile Gln Val Ala Pro Ala Ser Ser Lys
        195                 200                 205

Ser Val Arg Phe Pro Leu Arg Pro Gly Lys Gly Thr Tyr Gly Asp Arg
210                 215                 220

Cys Ile Val Lys Ala Asn His Phe Phe Ala Glu Leu Pro Asp Lys Asp
225                 230                 235                 240

Leu His Gln Tyr Asp Val Ser Ile Thr Pro Glu Val Thr Ser Arg Gly
                245                 250                 255

Val Asn Arg Ala Val Met Gly Glu Leu Val Thr Ile Tyr Arg Gln Ser
            260                 265                 270

His Leu Gly Gly Arg Leu Pro Ala Tyr Asp Gly Arg Lys Ser Leu Tyr
        275                 280                 285

Thr Ala Gly Pro Leu Pro Phe Thr Ser Met Ala Phe Glu Ile Thr Leu
    290                 295                 300

Gln Asp Glu Glu Asp Ser Leu Gly Gly Arg Gln Gly Gly His Arg Arg
305                 310                 315                 320

Glu Arg Val Phe Arg Val Val Ile Lys Phe Ala Ala Arg Ala Asp Leu
                325                 330                 335

His His Leu Ala Met Phe Leu Ala Gly Arg Gln Ala Asp Ala Pro Gln
            340                 345                 350

Glu Ala Leu Gln Val Leu Asp Ile Val Leu Arg Glu Leu Pro Thr Ala
        355                 360                 365

Arg Tyr Ser Pro Val Gly Arg Ser Phe Tyr Ser Pro Asn Leu Gly Arg
    370                 375                 380

Arg Gln Lys Leu Gly Glu Gly Leu Glu Ser Trp Arg Gly Phe Tyr Gln
385                 390                 395                 400

Ser Ile Arg Pro Thr Gln Met Gly Leu Ser Leu Asn Ile Asp Met Ser
                405                 410                 415

Ser Thr Ala Phe Ile Glu Pro Leu Pro Val Ile Asp Phe Val Ala Gln
            420                 425                 430

Leu Leu Asn Arg Asp Ile Ser Val Arg Pro Leu Ser Asp Ser Asp Arg
        435                 440                 445

Val Lys Ile Lys Lys Ala Leu Arg Gly Val Lys Val Glu Val Thr His
    450                 455                 460
```

```
Arg Gly Asn Met Arg Arg Lys Tyr Arg Ile Ser Gly Leu Thr Ser Gln
465                 470                 475                 480

Ala Thr Arg Glu Leu Ser Phe Pro Val Asp Asp Arg Gly Thr Val Lys
                485                 490                 495

Thr Val Val Gln Tyr Phe Met Glu Thr Tyr Gly Phe Ser Ile Gln His
            500                 505                 510

Thr Thr Leu Pro Cys Leu Gln Val Gly Asn Gln Gln Arg Pro Asn Tyr
            515                 520                 525

Leu Pro Met Glu Val Cys Lys Ile Val Glu Gly Gln Arg Tyr Ser Lys
            530                 535                 540

Arg Leu Asn Glu Lys Gln Ile Thr Ala Leu Leu Lys Val Thr Cys Gln
545                 550                 555                 560

Arg Pro Gln Glu Arg Glu Leu Asp Ile Leu Gln Thr Val His His Asn
                565                 570                 575

Ala Tyr Tyr Glu Asp Pro Tyr Ala Leu Glu Phe Gly Ile Arg Ile Asp
            580                 585                 590

Glu Arg Leu Ala Ala Val Glu Ala Arg Val Leu Pro Pro Arg Leu
                595                 600                 605

Lys Tyr His Asp Ser Gly Arg Glu Lys Asp Val Leu Pro Arg Val Gly
            610                 615                 620

Gln Trp Asn Met Met Asn Lys Lys Met Val Asn Gly Arg Val Ser
625                 630                 635                 640

Asn Trp Ala Cys Ile Asn Phe Ser Arg Asn Val Gln Asp Ser Ala Ala
                645                 650                 655

Arg Gly Phe Ser His Glu Leu Ala Val Met Cys Gln Ile Ser Gly Met
                660                 665                 670

Asp Phe Ala Leu Glu Pro Val Leu Pro Pro Val Thr Ala Arg Pro Glu
            675                 680                 685

His Val Glu Arg Ala Leu Lys Ala Arg Tyr Gln Asp Ala Met Asn Ile
            690                 695                 700

Leu Arg Pro Gln Gly Arg Glu Leu Asp Leu Leu Ile Val Ile Leu Pro
705                 710                 715                 720

Asp Asn Asn Gly Ser Leu Tyr Gly Asp Leu Lys Arg Ile Cys Glu Thr
                725                 730                 735

Glu Leu Gly Leu Val Ser Gln Cys Cys Leu Thr Lys His Val Phe Lys
            740                 745                 750

Met Ser Lys Gln Tyr Leu Ala Asn Val Ala Leu Lys Ile Asn Val Lys
            755                 760                 765

Val Gly Gly Arg Asn Thr Val Leu Leu Asp Ala Leu Ser Arg Arg Ile
            770                 775                 780

Pro Leu Val Ser Asp Arg Pro Thr Ile Ile Phe Gly Ala Asp Val Thr
785                 790                 795                 800

His Pro His Pro Gly Glu Asp Ser Ser Pro Ser Ile Ala Ala Val Val
                805                 810                 815

Ala Ser Gln Asp Trp Pro Glu Val Thr Lys Tyr Ala Gly Leu Val Ser
            820                 825                 830

Ala Gln Ala His Arg Gln Glu Leu Ile Gln Asp Leu Phe Lys Val Trp
            835                 840                 845

Gln Asp Pro Gln Arg Arg Thr Val Thr Gly Gly Met Ile Lys Glu Leu
            850                 855                 860

Leu Ile Ser Phe Lys Arg Ala Thr Gly Gln Lys Pro Gln Arg Ile Ile
865                 870                 875                 880
```

```
Phe Tyr Arg Asp Gly Val Ser Glu Gly Gln Phe Tyr Gln Val Leu Leu
                885                 890                 895

Tyr Glu Leu Asp Ala Ile Arg Lys Ala Cys Ala Ser Leu Glu Pro Asn
            900                 905                 910

Tyr Gln Pro Pro Val Thr Phe Val Val Gln Lys Arg His His Thr
        915                 920                 925

Arg Leu Phe Ala Asn Asn His Ser Asp Gln Arg Thr Val Asp Arg Ser
        930                 935                 940

Gly Asn Ile Leu Pro Gly Thr Val Val Asp Ser Lys Ile Cys His Pro
945                 950                 955                 960

Thr Glu Phe Asp Phe Tyr Leu Cys Ser His Ala Gly Ile Gln Gly Thr
                965                 970                 975

Ser Arg Pro Ala His Tyr His Val Leu Trp Asp Glu Asn Lys Phe Thr
            980                 985                 990

Ala Asp Glu Leu Gln Thr Leu Thr Asn Asn Leu Cys Tyr Thr Tyr Ala
        995                 1000                1005

Arg Cys Thr Arg Ser Val Ser Ile Val Pro Pro Ala Tyr Tyr Ala His
    1010                1015                1020

Leu Ala Ala Phe Arg Ala Arg Phe Tyr Met Glu Pro Asp Thr Ser Asp
1025                1030                1035                1040

Ser Gly Ser Leu Ala Ser Gly Ala Arg Gly Pro Pro Gly Ala Ala
                1045                1050                1055

Arg Ser Ser Thr Arg Gly Ala Gly Ser Val Glu Val Arg Pro Leu Pro
            1060                1065                1070

Ala Leu Lys Glu Asn Val Lys Arg Val Met Phe Tyr Cys
        1075                1080                1085

<210> SEQ ID NO 13
<211> LENGTH: 3714
<212> TYPE: DNA
<213> ORGANISM: Zea mays
<220> FEATURE:
<221> NAME/KEY: unsure
<222> LOCATION: (1789)
<223> OTHER INFORMATION: n = A, C, G or T

<400> SEQUENCE: 13
gccttccccc cctcccctcc tcaaaaaagg cggagaggtg gtggtgctcg tgggcacgca      60
gtggagcacc cagtacagca gcagcgctgc ggcagtggag ttaggagctt agcactccgc     120
ctccgttccc atcccgcgcg cagccgtcgg ccgagcctgc tcagtgccca tcatggtgag     180
gaagaagaga actggccctg gcggctctgg agaaacttct ggagagtctt caggagcttc     240
tggacaaggt tcctcacagc ggcctgaacg gactcaacaa cctgggcag gacgtggctg     300
ggtgcctcag cagggtggcc gtggtggcgg caacaccag gtcgtggtg gacattatca     360
aggccgtgga gggccaggtc cacatcaccc tggtggactg cctgagtatc accagcgtga     420
ataccaggga cgaggtggtg agtaccaggg acagtaccag gggcgtggtg gtgcccgctc     480
cagaggtgga atttcacagc catactatgg tgggcatagg ggaggtagtg ttggacgaaa     540
tgttcctcca ggtccatcca gaacagttcc cgagctgcac caagccccat acgtccagta     600
tcaagccccg gtgatttcac catccccatc gggacctggc tcatcctcac agcctatggc     660
agaggtgagc tctggacaag tccagcaaca gtttgagcaa cttgccattc atggtcagag     720
ttccatgagt caagaagttc aagtggcacc agcatcaagc aaatcggttc gattcccatt     780
acgccccggc aagggcactt atggggacag gtgcattgtg aaggcgaatc atttttttgc     840
```

```
tgagcttcct gacaaagacc ttcaccaata tgatgtaact ataacacctg aagttacttc    900
acgtggcgtt aatcgtgctg tcatgggaga gcttgtaaca ctatatagac aatcccattt    960
gggcgggcgt ctacctgcgt acgatggaag aaagagcctt ataccgctg gaccattgcc    1020 ttttacttct atgacatttg aaattacctt gcaagatgag gaagatagtg ttggcggtgg    1080
ccagggcgga caaaggcgcg agagagtatt tagggtggtg atcaaatttg cggcccgtgc    1140
tgatctccat catctggcta tgtttctagc tggaaggcaa gcagacgctc ctcaagaagc    1200
tcttcaagtg cttgacattg tactacgtga attgcctact gcgaggtatt ctcctgttgg    1260
taggtcattt tattctccca acttaggag acgtcagcaa cttggtgagg gtttggaaag    1320
ttggcgcggt ttttaccaaa gcataaggcc gacacagatg ggcctttcac tgaatattga    1380
tatgtcctct actgcattta tcgagcctct ccctgtgatt gattttgttg ctcagcttct    1440
taatagagat atttcagtta ggccattgtc tgattctgat cgcgtgaaga tcaaaaaagc    1500
cttaagaggt gtgaaggttg aggtcactca caggggaaac atgcgcagaa agtatcgcat    1560
ttctggcctc acctcacaag caacaagaga gctatcattc cctgttgatg atcgtggtac    1620
tgtgaagact gtggtccaat acttcatgga gacttatggt tttagcatcc agcacaccac    1680
tttaccgtgc ttgcaagtgg gcaatcaaca agaccaaat tatctgccta tggaggtttg    1740
caagatagtt gaaggacagc gttactcaaa gcgactcaat gagaaacana tcactgcttt    1800
actgaaagtg acctgccagc gccctcaaga gcgtgagctg gacatttttac agactgtgca    1860 tcacaatgcg tactatgaag acccgtatgc acaggaattt ggtataagaa ttgatgaacg    1920
ccttgctgca gttgaagctc gtgttctgcc accaccaagg cttaaatacc atgatagtgg    1980
ccgagagaag gatgttttgc ccagagttgg ccaatggaac atgatgaata agaaaatggt    2040
aaatggtggc agagtcagca actgggcatg tattaacttc tctcggaatg tgcaagatag    2100
tgccgctagg ggtttctgtc atgaactggc aatcatgtgc caaatatcag gaatggattt    2160
ttcccttgag cctgtgctgc ctccagtgac tgcaaggcca gaacatgttg aaagagcgtt    2220
gaaggcacgt tatcaagatg caatgaacat actgaggcca caggggaggg aacttgatct    2280
gctgattgta atactgcctg acattaatgg ttccttatat ggggatctca aaaggatctg    2340
tgagactgat ctcggattgg tctcccagtg ttgtctgact aaacatgttt ttaagatgag    2400
caagcagtat cttgcaaatg ttgcactcaa aataaatgtt aaggttggtg gaaggaatac    2460
tgtacttgta gatgctttga caaggagaat ccccccttgtc agtgacagac cgaccataat    2520
atttggtgct gatgttaccc atccacatcc tggagaagat tccagtcctt ccattgcagc    2580
tgtggttgct tcgcaagact ggcctgaggt caccaaatat gctggactag tgagtgccca    2640
agcccatcgc caggagctga tacaggatct tttcaaagta tggcaagatc cacagagaag    2700
gacagtaact ggtggcatga taaaggaact tctcatttct ttcaagagag caactggaca    2760
gaagccccag aggatcatat tctacaggga tggtgtcagt gagggacagt tctatcaagt    2820
attgttgtat gaacttgatg ccatcagaaa ggcatgtgca tccttggagc ccaactacca    2880
gcctccagtt acttttgtcg tggtgcagaa acgacatcac actaggctgt ttgctaataa    2940
ccacaacgat cagcgtacag ttgatagaag cggaaacata ctgcctggca ccgtggttga    3000
ttcgaagatt tgccatccta ctgaatttga tttctacctg tgtagccatg ctggcattca    3060
gggaacaagc cgccctgctc attaccatgt cctgtgggac gagaacaagt tcacagctga    3120
tgagctgcag actctgacaa caacctatg ctacacgtac gctaggtgca cccgctccgt    3180
gtcaattgtg cccccggcat actatgctca tctggcagcc ttccgagctc gcttctacat    3240
```

```
ggagccagat acctctgaca gtggctcaat ggccagtggt gcccgtggcc ctccaccagg    3300
tgcggcacgc agcatgagag gagcggggag tgttgcggtc aggcccctac ctgctctcaa    3360
ggaaaacgtg aagcgtgtca tgttttactg ctgagatgct gagctacctt caccaagaaa    3420
atatcctgac ttgttccatg tacccgcact gtttcggtga tactatctga caccgaattt    3480
atgcattaag tcttccagtg gtctggagat tttaagtaac gcctgttttt attcgtgagt    3540
tgtaacgctg cagttcgagg agcttcagtg ctgtatgatg tgtaaactat ttgttgtaag    3600
ttgtaaccaa ttgttgtaag ttgtaaccag ccactatgtt ataatcctgt ttgtttcagc    3660
taaaaaaaaa aaaaaaaaaa aaaaaaaaaa aaaaaaaaaa aaaa                     3714

<210> SEQ ID NO 14
<211> LENGTH: 1073
<212> TYPE: PRT
<213> ORGANISM: Zea mays
<220> FEATURE:
<221> NAME/KEY: UNSURE
<222> LOCATION: (539)
<223> OTHER INFORMATION: Xaa = ANY AMINO ACID

<400> SEQUENCE: 14

Met Val Arg Lys Lys Arg Thr Gly Pro Gly Gly Ser Gly Glu Thr Ser
 1               5                  10                  15

Gly Glu Ser Ser Gly Ala Ser Gly Gln Gly Ser Ser Gln Arg Pro Glu
             20                  25                  30

Arg Thr Gln Gln Pro Gly Ala Gly Arg Gly Trp Val Pro Gln Gln Gly
         35                  40                  45

Gly Arg Gly Gly Gly Gln His Gln Gly Arg Gly Gly His Tyr Gln Gly
     50                  55                  60

Arg Gly Gly Pro Gly Pro His Pro Gly Gly Leu Pro Glu Tyr His
 65                  70                  75                  80

Gln Arg Glu Tyr Gln Gly Arg Gly Gly Glu Tyr Gln Gly Gln Tyr Gln
                 85                  90                  95

Gly Arg Gly Gly Ala Arg Ser Arg Gly Ile Ser Gln Pro Tyr Tyr
            100                 105                 110

Gly Gly His Arg Gly Gly Ser Val Gly Arg Asn Val Pro Gly Pro
        115                 120                 125

Ser Arg Thr Val Pro Glu Leu His Gln Ala Pro Tyr Val Gln Tyr Gln
    130                 135                 140

Ala Pro Val Ile Ser Pro Ser Pro Ser Gly Pro Gly Ser Ser Ser Gln
145                 150                 155                 160

Pro Met Ala Glu Val Ser Ser Gly Gln Val Gln Gln Phe Glu Gln
                165                 170                 175

Leu Ala Ile His Gly Gln Ser Ser Met Ser Gln Glu Val Gln Val Ala
            180                 185                 190

Pro Ala Ser Ser Lys Ser Val Arg Phe Pro Leu Arg Pro Gly Lys Gly
        195                 200                 205

Thr Tyr Gly Asp Arg Cys Ile Val Lys Ala Asn His Phe Phe Ala Glu
    210                 215                 220

Leu Pro Asp Lys Asp Leu His Gln Tyr Asp Val Thr Ile Thr Pro Glu
225                 230                 235                 240

Val Thr Ser Arg Gly Val Asn Arg Ala Val Met Gly Glu Leu Val Thr
                245                 250                 255

Leu Tyr Arg Gln Ser His Leu Gly Gly Arg Leu Pro Ala Tyr Asp Gly
            260                 265                 270
```

```
Arg Lys Ser Leu Tyr Thr Ala Gly Pro Leu Pro Phe Thr Ser Met Thr
            275                 280                 285

Phe Glu Ile Thr Leu Gln Asp Glu Glu Asp Ser Val Gly Gly Gly Gln
        290                 295                 300

Gly Gly Gln Arg Arg Glu Arg Val Phe Arg Val Val Ile Lys Phe Ala
305                 310                 315                 320

Ala Arg Ala Asp Leu His His Leu Ala Met Phe Leu Ala Gly Arg Gln
                325                 330                 335

Ala Asp Ala Pro Gln Glu Ala Leu Gln Val Leu Asp Ile Val Leu Arg
            340                 345                 350

Glu Leu Pro Thr Ala Arg Tyr Ser Pro Val Gly Arg Ser Phe Tyr Ser
        355                 360                 365

Pro Asn Leu Gly Arg Arg Gln Gln Leu Gly Glu Gly Leu Glu Ser Trp
    370                 375                 380

Arg Gly Phe Tyr Gln Ser Ile Arg Pro Thr Gln Met Gly Leu Ser Leu
385                 390                 395                 400

Asn Ile Asp Met Ser Ser Thr Ala Phe Ile Glu Pro Leu Pro Val Ile
                405                 410                 415

Asp Phe Val Ala Gln Leu Leu Asn Arg Asp Ile Ser Val Arg Pro Leu
            420                 425                 430

Ser Asp Ser Asp Arg Val Lys Ile Lys Lys Ala Leu Arg Gly Val Lys
        435                 440                 445

Val Glu Val Thr His Arg Gly Asn Met Arg Arg Lys Tyr Arg Ile Ser
    450                 455                 460

Gly Leu Thr Ser Gln Ala Thr Arg Glu Leu Ser Phe Pro Val Asp Asp
465                 470                 475                 480

Arg Gly Thr Val Lys Thr Val Val Gln Tyr Phe Met Glu Thr Tyr Gly
                485                 490                 495

Phe Ser Ile Gln His Thr Thr Leu Pro Cys Leu Gln Val Gly Asn Gln
            500                 505                 510

Gln Arg Pro Asn Tyr Leu Pro Met Glu Val Cys Lys Ile Val Glu Gly
        515                 520                 525

Gln Arg Tyr Ser Lys Arg Leu Asn Glu Lys Xaa Ile Thr Ala Leu Leu
    530                 535                 540

Lys Val Thr Cys Gln Arg Pro Gln Glu Arg Glu Leu Asp Ile Leu Gln
545                 550                 555                 560

Thr Val His His Asn Ala Tyr Tyr Glu Asp Pro Tyr Ala Gln Glu Phe
                565                 570                 575

Gly Ile Arg Ile Asp Glu Arg Leu Ala Ala Val Glu Ala Arg Val Leu
            580                 585                 590

Pro Pro Pro Arg Leu Lys Tyr His Asp Ser Gly Arg Glu Lys Asp Val
        595                 600                 605

Leu Pro Arg Val Gly Gln Trp Asn Met Met Asn Lys Lys Met Val Asn
    610                 615                 620

Gly Gly Arg Val Ser Asn Trp Ala Cys Ile Asn Phe Ser Arg Asn Val
625                 630                 635                 640

Gln Asp Ser Ala Ala Arg Gly Phe Cys His Glu Leu Ala Ile Met Cys
                645                 650                 655

Gln Ile Ser Gly Met Asp Phe Ser Leu Glu Pro Val Leu Pro Pro Val
            660                 665                 670

Thr Ala Arg Pro Glu His Val Glu Arg Ala Leu Lys Ala Arg Tyr Gln
        675                 680                 685
```

Asp Ala Met Asn Ile Leu Arg Pro Gln Gly Arg Glu Leu Asp Leu Leu
        690                 695                 700

Ile Val Ile Leu Pro Asp Ile Asn Gly Ser Leu Tyr Gly Asp Leu Lys
705                 710                 715                 720

Arg Ile Cys Glu Thr Asp Leu Gly Leu Val Ser Gln Cys Cys Leu Thr
                725                 730                 735

Lys His Val Phe Lys Met Ser Lys Gln Tyr Leu Ala Asn Val Ala Leu
            740                 745                 750

Lys Ile Asn Val Lys Val Gly Arg Asn Thr Val Leu Val Asp Ala
        755                 760                 765

Leu Thr Arg Arg Ile Pro Leu Val Ser Asp Arg Pro Thr Ile Ile Phe
770                 775                 780

Gly Ala Asp Val Thr His Pro His Pro Gly Glu Asp Ser Ser Pro Ser
785                 790                 795                 800

Ile Ala Ala Val Val Ala Ser Gln Asp Trp Pro Glu Val Thr Lys Tyr
                805                 810                 815

Ala Gly Leu Val Ser Ala Gln Ala His Arg Gln Glu Leu Ile Gln Asp
            820                 825                 830

Leu Phe Lys Val Trp Gln Asp Pro Gln Arg Arg Thr Val Thr Gly Gly
        835                 840                 845

Met Ile Lys Glu Leu Leu Ile Ser Phe Lys Arg Ala Thr Gly Gln Lys
850                 855                 860

Pro Gln Arg Ile Ile Phe Tyr Arg Asp Gly Val Ser Glu Gly Gln Phe
865                 870                 875                 880

Tyr Gln Val Leu Leu Tyr Glu Leu Asp Ala Ile Arg Lys Ala Cys Ala
                885                 890                 895

Ser Leu Glu Pro Asn Tyr Gln Pro Pro Val Thr Phe Val Val Val Gln
            900                 905                 910

Lys Arg His His Thr Arg Leu Phe Ala Asn Asn His Asn Asp Gln Arg
        915                 920                 925

Thr Val Asp Arg Ser Gly Asn Ile Leu Pro Gly Thr Val Val Asp Ser
930                 935                 940

Lys Ile Cys His Pro Thr Glu Phe Asp Phe Tyr Leu Cys Ser His Ala
945                 950                 955                 960

Gly Ile Gln Gly Thr Ser Arg Pro Ala His Tyr His Val Leu Trp Asp
                965                 970                 975

Glu Asn Lys Phe Thr Ala Asp Glu Leu Gln Thr Leu Thr Asn Asn Leu
            980                 985                 990

Cys Tyr Thr Tyr Ala Arg Cys Thr Arg Ser Val Ser Ile Val Pro Pro
        995                 1000                1005

Ala Tyr Tyr Ala His Leu Ala Ala Phe Arg Ala Arg Phe Tyr Met Glu
    1010                1015                1020

Pro Asp Thr Ser Asp Ser Gly Ser Met Ala Ser Gly Ala Arg Gly Pro
1025                1030                1035                1040

Pro Pro Gly Ala Ala Arg Ser Arg Gly Ala Gly Ser Val Ala Val
                1045                1050                1055

Arg Pro Leu Pro Ala Leu Lys Glu Asn Val Lys Arg Val Met Phe Tyr
            1060                1065                1070

Cys

<210> SEQ ID NO 15
<211> LENGTH: 3072
<212> TYPE: DNA
<213> ORGANISM: Zea mays

```
<220> FEATURE:
<221> NAME/KEY: unsure
<222> LOCATION: (411)
<223> OTHER INFORMATION: n = A, C, G or T

<400> SEQUENCE: 15
ctccaaatac gtaacaaact tctacgtgag cgccagggca gttgcgccca tgggaaggca      60
tccgcctgtc gatgaggcga tggacttcaa cggcaacgga cgggacgagg caaacccgag     120
cggctctgag gcggggaacc acaacgagca ccgcggcgac gacccctcgc gcgttggcca     180
gagcctgccc gccgatatcc gccaaaatgg gcagccaacc ctcggggagg agatcaccgc     240
gccgctgtgg gaggagttcg aggcgctcgg catccacgtc cgccgctccg agcccgtgtt     300
cccgccgcgc ccagggtacg gcgccgcggg gacgccgtac gtcgtcaggg ccaacctctt     360
cctcggtcgc ctcgtcgacg aggccctgca tcagtacaac gtaaccattt ngcccgagcc     420
gacgcccaag gccgcgtaca gagagatcat gacgaagctg ttgtccgaga accagcacac     480
ggatttcgac ggccgcttct ccgtgtacga tgatggtgac tcgctcttca cagccggtgc     540
gctgccgttc gacaccaagg agttcgaggt ccccctctct gcaggcggcg acgaaaagat     600
ggacaggaag tacaaggtga tgatcaacca tgccgcaacg attagtctgc tacagctgag     660
gatgctgtta gcgggctatc ccacggacat ccccgcgcag gcgctcgtgg tcctcgacac     720
cgtgctgcgt gacgtcttca acgaacgcaa tgacatggaa tgcgtcgtga ttgacaaaaa     780
ggatcgcaca ctgggtgttg acgcatggaa ggggctctat ctgagcatca ggccaacaca     840
aaactgcttg tctctgattg cagacgtgtc ctcatctgta ttcgttcaac ccctgctatt     900
gattgaattc gttcagaaga tcctaaagat agatgccgtg ataggaact tgactaaacc       960 tgagtatgac aagctcttga aggccctcag gggtgtgagg attcaagtca cacacagaga    1020
taatagacgc cgagtatggt caaagaaaaa agataataga cgccaactct ctacgtacag    1080
agttgctggc ttgtcagtga atcctactaa tgatttgagt tttgaatcaa aggttggagt    1140
cacaacgact gtgattgatt acttcagaga aatatacggc ctggaactga atacaaata    1200 tctcccatgc gtcaatgctg gcagcgagca ggatccaatc tattttccta tagaggtttg    1260
caagatagct cccaagcagt gttaccagaa gaagctggaa ggtagtcagt tttctactcc    1320
aaggaagtca gcctggatcc atcctgaagc cgagcaatcc tgtcctcaga ttgttgagca    1380
gaggcagtac aaacaaacca aacgtgcaaa tgaatttgac ttagaatttg atggcaatct    1440
tacaacagtt gctgctagag ttctgctgcc tccaaatctt aagtatgatg attctgtatc    1500
acagaaaaca tggtttccac tggatgggta ctggaatatg aaagacaaga agtaataaa    1560 tggtgccaag atcagaaact gggcatgtct taatttttgt gaagatttat ccaaggaaga    1620
tattaagaag ttttgcttta agctggctga aatgtctcgt attactggac tggactttgc    1680
cgatttgaag ctcccaatat tcactgcacg tccagatcga gttgaagatg gtattcgtag    1740
gtgctatcag gaagcgaaga acaagctaag ggatcagaag attgatttac tgcttgctat    1800
actaccagat aaaaaagaca gtttatatgg aaatattaaa aggatctgtg agacagatat    1860
tggtcttgtg tcacagtgtt gtcgaaggtc aagagtctta gtgaataata atcagatatt    1920
ggcaaatatt gctattaaga tcaatgccaa ggttggagga agaatctcag tattcgatga    1980
cgtacagaag agtttaccgg ttgtttcaaa taagccaaca attatatttg gtgctcatgt    2040
ttctcaccct tctgttgtag atggttctac tggcccttct attgcttctg tcgttgcatc    2100
ccaagactgg catgaggtgt ctaagtataa tggtgttgtt cgtgcacaag gtcacactga    2160
```

```
agagatcggt ggccttgaag acattgtcaa ggagctcctt catgcatttg caaacgagtc    2220
caaggagaag ctccagcagc tgatattcta cagggatggc ataagtgagg gtcaattcaa    2280
tcgaattttg gagaaagaaa tcccagcgat agaaaaggct tggaacgcac tgtatgacaa    2340
tgagaagcca caaatcacct tcgttgttgt gcagaagagg cataaactga ggctgttccc    2400
cgtggacgac aactataaga tccgttctgc taagaagaaa attgttgagc ctggcacagt    2460
ggttgatagt gagatctgtc acccagcaga atttgatttc ttcctttgca gccaatctgg    2520
tggtatcaaa ggcccaaggc gtcctgtgag gtaccttgta ctgcgagatg ataacaactt    2580
cacggcagat gaactgcagg ctctcacaaa taacctgtgc tacacttatt caggcggcaa    2640
tcgttcgttg tcggtcgctc ctcccgcata ctacgcccaa aagctcgcac atcgggcccg    2700
cgtctacctc gccaaaggct cggacaataa tgcagcagct gctaatggtg gtcggaagca    2760
aattccagag ataaagaatg agctgaaggg gtccatgttc tactgctagt cctttgcctg    2820
ctgaacggac gatgcattgt tctatagtga aagacttgag tgtgctctga gtctctgact    2880
gacatctgga gaaggatggc atctgcaata gtcgccgtgt tcttttttagt acactagaat    2940 aaatggatgt tttttgtgga cgcccatgtt gaactagttt tcttttccag taagtacttc    3000
agaatgagtg agataaatat atcattcagc gtctggtggt ctggcattgg aaaaaaaaaa    3060
aaaaaaaaaa ag                                                        3072
```

<210> SEQ ID NO 16
<211> LENGTH: 919
<212> TYPE: PRT
<213> ORGANISM: Zea mays
<220> FEATURE:
<221> NAME/KEY: UNSURE
<222> LOCATION: (121)
<223> OTHER INFORMATION: Xaa = ANY AMINO ACID

<400> SEQUENCE: 16

```
Met Gly Arg His Pro Val Asp Glu Ala Met Asp Phe Asn Gly Asn
  1               5                  10                  15

Gly Arg Asp Glu Ala Asn Pro Ser Gly Ser Glu Ala Gly Asn His Asn
                 20                  25                  30

Glu His Arg Gly Asp Asp Pro Ser Arg Val Gly Gln Ser Leu Pro Ala
         35                  40                  45

Asp Ile Arg Gln Asn Gly Gln Pro Thr Leu Gly Glu Glu Ile Thr Ala
     50                  55                  60

Pro Leu Trp Glu Glu Phe Glu Ala Leu Gly Ile His Val Arg Arg Ser
 65                  70                  75                  80

Glu Pro Val Phe Pro Pro Arg Pro Gly Tyr Gly Ala Ala Gly Thr Pro
                 85                  90                  95

Tyr Val Val Arg Ala Asn Leu Phe Leu Gly Arg Leu Val Asp Glu Ala
            100                 105                 110

Leu His Gln Tyr Asn Val Thr Ile Xaa Pro Glu Pro Thr Pro Lys Ala
        115                 120                 125

Ala Tyr Arg Glu Ile Met Thr Lys Leu Leu Ser Glu Asn Gln His Thr
    130                 135                 140

Asp Phe Asp Gly Arg Phe Ser Val Tyr Asp Asp Gly Asp Ser Leu Phe
145                 150                 155                 160

Thr Ala Gly Ala Leu Pro Phe Asp Thr Lys Glu Phe Glu Val Pro Leu
                165                 170                 175

Ser Ala Gly Gly Asp Glu Lys Met Asp Arg Lys Tyr Lys Val Met Ile
            180                 185                 190
```

```
Asn His Ala Ala Thr Ile Ser Leu Leu Gln Leu Arg Met Leu Leu Ala
            195                 200                 205

Gly Tyr Pro Thr Asp Ile Pro Ala Gln Ala Leu Val Val Leu Asp Thr
            210                 215                 220

Val Leu Arg Asp Val Phe Asn Glu Arg Asn Asp Met Glu Cys Val Val
225                 230                 235                 240

Ile Asp Lys Lys Asp Arg Thr Leu Gly Val Asp Ala Trp Lys Gly Leu
            245                 250                 255

Tyr Leu Ser Ile Arg Pro Thr Gln Asn Cys Leu Ser Leu Ile Ala Asp
            260                 265                 270

Val Ser Ser Ser Val Phe Val Gln Pro Leu Leu Leu Ile Glu Phe Val
            275                 280                 285

Gln Lys Ile Leu Lys Ile Asp Ala Val Asp Arg Asn Leu Thr Lys Pro
            290                 295                 300

Glu Tyr Asp Lys Leu Leu Lys Ala Leu Arg Gly Val Arg Ile Gln Val
305                 310                 315                 320

Thr His Arg Asp Asn Arg Arg Val Trp Ser Lys Lys Lys Asp Asn
            325                 330                 335

Arg Arg Gln Leu Ser Thr Tyr Arg Val Ala Gly Leu Ser Val Asn Pro
            340                 345                 350

Thr Asn Asp Leu Ser Phe Glu Ser Lys Val Gly Val Thr Thr Thr Val
            355                 360                 365

Ile Asp Tyr Phe Arg Glu Ile Tyr Gly Leu Glu Leu Lys Tyr Lys Tyr
            370                 375                 380

Leu Pro Cys Val Asn Ala Gly Ser Glu Gln Asp Pro Ile Tyr Phe Pro
385                 390                 395                 400

Ile Glu Val Cys Lys Ile Ala Pro Lys Gln Cys Tyr Gln Lys Lys Leu
            405                 410                 415

Glu Gly Ser Gln Phe Ser Thr Pro Arg Lys Ser Ala Trp Ile His Pro
            420                 425                 430

Glu Ala Glu Gln Ser Cys Pro Gln Ile Val Glu Gln Arg Gln Tyr Lys
            435                 440                 445

Gln Thr Lys Arg Ala Asn Glu Phe Asp Leu Glu Phe Asp Gly Asn Leu
            450                 455                 460

Thr Thr Val Ala Ala Arg Val Leu Leu Pro Pro Asn Leu Lys Tyr Asp
465                 470                 475                 480

Asp Ser Val Ser Gln Lys Thr Trp Phe Pro Leu Asp Gly Tyr Trp Asn
            485                 490                 495

Met Lys Asp Lys Lys Val Ile Asn Gly Ala Lys Ile Arg Asn Trp Ala
            500                 505                 510

Cys Leu Asn Phe Cys Glu Asp Leu Ser Lys Glu Asp Ile Lys Lys Phe
            515                 520                 525

Cys Phe Lys Leu Ala Glu Met Ser Arg Ile Thr Gly Leu Asp Phe Ala
            530                 535                 540

Asp Leu Lys Leu Pro Ile Phe Thr Ala Arg Pro Asp Arg Val Glu Asp
545                 550                 555                 560

Gly Ile Arg Arg Cys Tyr Gln Glu Ala Lys Asn Lys Leu Arg Asp Gln
            565                 570                 575

Lys Ile Asp Leu Leu Leu Ala Ile Leu Pro Asp Lys Lys Asp Ser Leu
            580                 585                 590

Tyr Gly Asn Ile Lys Arg Ile Cys Glu Thr Asp Ile Gly Leu Val Ser
            595                 600                 605
```

Gln Cys Cys Arg Arg Ser Arg Val Leu Val Asn Asn Gln Ile Leu
                        610                 615                 620

Ala Asn Ile Ala Ile Lys Ile Asn Ala Lys Val Gly Gly Arg Ile Ser
                    625                 630                 635                 640

Val Phe Asp Asp Val Gln Lys Ser Leu Pro Val Ser Asn Lys Pro
                                    645                 650                 655

Thr Ile Ile Phe Gly Ala His Val His Pro Ser Val Val Asp Gly
                                660                 665                 670

Ser Thr Gly Pro Ser Ile Ala Ser Val Val Ala Ser Gln Asp Trp His
                            675                 680                 685

Glu Val Ser Lys Tyr Asn Gly Val Val Arg Ala Gln Gly His Thr Glu
                    690                 695                 700

Glu Ile Gly Gly Leu Glu Asp Ile Val Lys Glu Leu Leu His Ala Phe
                    705                 710                 715                 720

Ala Asn Glu Ser Lys Glu Lys Leu Gln Gln Leu Ile Phe Tyr Arg Asp
                                    725                 730                 735

Gly Ile Ser Glu Gly Gln Phe Asn Arg Ile Leu Glu Lys Glu Ile Pro
                                740                 745                 750

Ala Ile Glu Lys Ala Trp Asn Ala Leu Tyr Asp Asn Glu Lys Pro Gln
                            755                 760                 765

Ile Thr Phe Val Val Val Gln Lys Arg His Lys Leu Arg Leu Phe Pro
                    770                 775                 780

Val Asp Asp Asn Tyr Lys Ile Arg Ser Ala Lys Lys Ile Val Glu
                    785                 790                 795                 800

Pro Gly Thr Val Val Asp Ser Glu Ile Cys His Pro Ala Glu Phe Asp
                                    805                 810                 815

Phe Phe Leu Cys Ser Gln Ser Gly Gly Ile Lys Gly Pro Arg Arg Pro
                                820                 825                 830

Val Arg Tyr Leu Val Leu Arg Asp Asp Asn Asn Phe Thr Ala Asp Glu
                            835                 840                 845

Leu Gln Ala Leu Thr Asn Asn Leu Cys Tyr Thr Tyr Ser Gly Gly Asn
                    850                 855                 860

Arg Ser Leu Ser Val Ala Pro Pro Ala Tyr Tyr Ala Gln Lys Leu Ala
                    865                 870                 875                 880

His Arg Ala Arg Val Tyr Leu Ala Lys Gly Ser Asp Asn Asn Ala Ala
                                    885                 890                 895

Ala Ala Asn Gly Gly Arg Lys Gln Ile Pro Glu Ile Lys Asn Glu Leu
                                900                 905                 910

Lys Gly Ser Met Phe Tyr Cys
                            915

<210> SEQ ID NO 17
<211> LENGTH: 400
<212> TYPE: DNA
<213> ORGANISM: Zea mays
<220> FEATURE:
<221> NAME/KEY: unsure
<222> LOCATION: (286)
<223> OTHER INFORMATION: n = A, C, G or T
<220> FEATURE:
<221> NAME/KEY: unsure
<222> LOCATION: (320)..(321)
<223> OTHER INFORMATION: n = A, C, G or T
<220> FEATURE:
<221> NAME/KEY: unsure
<222> LOCATION: (323)
<223> OTHER INFORMATION: n = A, C, G or T
<220> FEATURE:
<221> NAME/KEY: unsure

```
<222> LOCATION: (371)
<223> OTHER INFORMATION: n = A, C, G or T
<220> FEATURE:
<221> NAME/KEY: unsure
<222> LOCATION: (383)
<223> OTHER INFORMATION: n = A, C, G or T

<400> SEQUENCE: 17
caagaaggca caagggtgtc agttgtgcat tactttaaac aacgatataa ctactactta      60
caatacactc actggccatg ccttcaagct ggccgtgttg acaagcagat ctatttacct     120
atagaggttt gcagcatagt tcagggacaa cgctactcca gtaagctgaa tgagaatcaa     180
gtcaggaaca tcctgcagtt tacctgcgag cgaccagcag ataggcaaac tagaactttt     240
gaggtattca agaattacaa atctgatgga tcaacttatg caaanaatt tggccttacg      300
tttgatggat caacttacgn ntnggatgct cgagttgctc ccagtccaag gcttaaatac     360
catgatccga naaaaaagt ttnggcaacc tccatcggaa                            400

<210> SEQ ID NO 18
<211> LENGTH: 126
<212> TYPE: PRT
<213> ORGANISM: Zea mays
<220> FEATURE:
<221> NAME/KEY: UNSURE
<222> LOCATION: (96)
<223> OTHER INFORMATION: Xaa = ANY AMINO ACID
<220> FEATURE:
<221> NAME/KEY: UNSURE
<222> LOCATION: (107)..(108)
<223> OTHER INFORMATION: Xaa = ANY AMINO ACID
<220> FEATURE:
<221> NAME/KEY: UNSURE
<222> LOCATION: (124)
<223> OTHER INFORMATION: Xaa = ANY AMINO ACID

<400> SEQUENCE: 18

Gln Glu Gly Thr Arg Val Ser Val Val His Tyr Phe Lys Gln Arg Tyr
 1               5                  10                  15

Asn Tyr Tyr Leu Gln Tyr Thr His Trp Pro Cys Leu Gln Ala Gly Arg
            20                  25                  30

Val Asp Lys Gln Ile Tyr Leu Pro Ile Glu Val Cys Ser Ile Val Gln
        35                  40                  45

Gly Gln Arg Tyr Ser Ser Lys Leu Asn Glu Asn Gln Val Arg Asn Ile
    50                  55                  60

Leu Gln Phe Thr Cys Glu Arg Pro Ala Asp Arg Gln Thr Arg Thr Phe
65                  70                  75                  80

Glu Val Phe Lys Asn Tyr Lys Ser Asp Gly Ser Thr Tyr Ala Lys Xaa
                85                  90                  95

Phe Gly Leu Thr Phe Asp Gly Ser Thr Tyr Xaa Xaa Asp Ala Arg Val
            100                 105                 110

Ala Pro Ser Pro Arg Leu Lys Tyr His Asp Pro Xaa Lys Lys
        115                 120                 125

<210> SEQ ID NO 19
<211> LENGTH: 550
<212> TYPE: DNA
<213> ORGANISM: Zea mays
<220> FEATURE:
<221> NAME/KEY: unsure
<222> LOCATION: (479)
<223> OTHER INFORMATION: n = A, C, G or T
<220> FEATURE:
<221> NAME/KEY: unsure
<222> LOCATION: (481)
```

```
<223> OTHER INFORMATION: n = A, C, G or T
<220> FEATURE:
<221> NAME/KEY: unsure
<222> LOCATION: (492)
<223> OTHER INFORMATION: n = A, C, G or T
<220> FEATURE:
<221> NAME/KEY: unsure
<222> LOCATION: (494)
<223> OTHER INFORMATION: n = A, C, G or T
<220> FEATURE:
<221> NAME/KEY: unsure
<222> LOCATION: (512)
<223> OTHER INFORMATION: n = A, C, G or T
<220> FEATURE:
<221> NAME/KEY: unsure
<222> LOCATION: (544)
<223> OTHER INFORMATION: n = A, C, G or T

<400> SEQUENCE: 19
cggacgcgtg ggcaagattg tagaagggca gagatactct aagaagctta atgacagaca      60
agtgacgaac atacttagag caacttgtaa acgtccccag gagagagaga agagcatacg     120
tgatatggtt ctgcataaca agtatgcaga tgataagttt gctcaggagt ttggcatcga     180
agttagcagt gatctagtga ctgttccagc ccgtgtgctg cctccacccc tgttgaaata     240
tcatgactct ggtagggaga aaacttgtgc accaagtgtt ggacaatgga acatgatcaa     300
taagaaaatg atcaatggtg gaactattga taactggact tgtttgaact tttcacgcat     360 gcgcccctgat gaagtacaaa ggttctgtat ggatctgact catatgtgca atgccactgg     420
aatggttgtc aatccacgcc catttattga aatccggtct gctgctccta accatatana     480
naatgctttg ananatgttc acaagaaaac cncccaaata cttgcccaca acatgggaa      540 atcnactcca                                                            550

<210> SEQ ID NO 20
<211> LENGTH: 163
<212> TYPE: PRT
<213> ORGANISM: Zea mays
<220> FEATURE:
<221> NAME/KEY: UNSURE
<222> LOCATION: (160)
<223> OTHER INFORMATION: Xaa = ANY AMINO ACID

<400> SEQUENCE: 20

Gly Arg Val Gly Lys Ile Val Glu Gly Gln Arg Tyr Ser Lys Lys Leu
 1               5                  10                  15

Asn Asp Arg Gln Val Thr Asn Ile Leu Arg Ala Thr Cys Lys Arg Pro
            20                  25                  30

Gln Glu Arg Glu Lys Ser Ile Arg Asp Met Val Leu His Asn Lys Tyr
        35                  40                  45

Ala Asp Asp Lys Phe Ala Gln Glu Phe Gly Ile Glu Val Ser Ser Asp
    50                  55                  60

Leu Val Thr Val Pro Ala Arg Val Leu Pro Pro Leu Leu Lys Tyr
 65                  70                  75                  80

His Asp Ser Gly Arg Glu Lys Thr Cys Ala Pro Ser Val Gly Gln Trp
                85                  90                  95

Asn Met Ile Asn Lys Lys Met Ile Asn Gly Gly Thr Ile Asp Asn Trp
            100                 105                 110

Thr Cys Leu Asn Phe Ser Arg Met Arg Pro Asp Glu Val Gln Arg Phe
        115                 120                 125

Cys Met Asp Leu Thr His Met Cys Asn Ala Thr Gly Met Val Val Asn
    130                 135                 140
```

Pro Arg Pro Phe Ile Glu Ile Arg Ser Ala Ala Pro Asn His Ile Xaa
145                 150                 155                 160

Asn Ala Leu

<210> SEQ ID NO 21
<211> LENGTH: 3009
<212> TYPE: DNA
<213> ORGANISM: Zea mays

<400> SEQUENCE: 21

| | | | | | |
|---|---|---|---|---|---|
| ctcgcctcgt | ccgtcctcct | gcctacttcc | ttgcttttgg | taggtgctgc | ttgttttatc | 60 |
| ttgaaatggg | ctctcatgat | ggcgaggatg | aagagttgcc | accccccct | ccggtgccac | 120 |
| cagatgtgat | tcccattaaa | gctgaagatg | ctgtgggtga | atcaccagca | aaccatatat | 180 |
| taaagccaaa | gagattactg | atggacaggc | ctggtatagg | aagaaaaggg | cagccgaccc | 240 |
| agctctattc | aaatcacttt | aaagtcgctg | tgaagagtac | agaagacgtc | ttctttcact | 300 |
| actatgtaaa | cctgaagtat | gaggatgatc | gacccgttga | tggtaaaggg | atcggcagaa | 360 |
| aggtgattga | taaactgcag | cagacatatc | gtgcagagct | ttctaacaag | gactttgcat | 420 |
| atgatgagaa | aaagagcctg | tttacagttg | gtggtcttcc | acaaaaaaag | aatgagttca | 480 |
| ccgttgtctt | ggaggacgta | tctactggaa | agactgctgc | caatgggagc | cctggaggta | 540 |
| atgacagtcc | tggaggtggt | gataggaaga | gagtgaggag | gccataccag | acgaaaactt | 600 |
| tcaaagtgga | gataaatttt | gcagcagagg | ttcctatgag | tgctattggt | caagtcatta | 660 |
| gaggcgaaga | atctgagaac | tccctggagg | cgcttcgtgt | tcttgatatc | atactgaggc | 720 |
| agcattccgc | agaacaaggc | tgccttttgg | ttaagcaatc | attttctac | aacaacccctt | 780 |
| catgctttgt | tgacttgggt | ggtggtgtga | tgggttgtcg | tggatttcat | tcaagcttcc | 840 |
| gtggcacaca | gagtggactt | tccctcaatg | ttgatgtctc | aacaacaatg | atcgtgaaac | 900 |
| ctggccctgt | tattgatttt | cttctttcta | accagaatgt | taatgatcct | agcagaattg | 960 |
| attggcaaaa | ggccaagcgt | gctctcaagg | gcttgaggat | tagaaccact | cctgcaaatt | 1020 |
| cagaattcaa | gattttggt | ctcagcgaga | ggatctgcaa | agaacaaacg | tttccgctga | 1080 |
| ggcagagaaa | tggtagcaac | ggagattgtg | ataccattga | aataactgtc | tatgactact | 1140 |
| atgcaaagaa | aggaatcgat | ctaaagtatt | ctggtgattt | cccctgtata | aatacaggga | 1200 |
| aggcaaagcg | cccaacatat | tttccaatcg | agctatgctc | gcttgttccg | cttcaaagat | 1260 |
| acaccaaagc | tttgtctacg | ctacaaaggt | catcccttgt | ggagaagtct | agacagaagc | 1320 |
| ctgaagaaag | gatgaccgtt | ctaaatgatg | cactgcaacg | cagtaactac | gattctgacc | 1380 |
| ccatgttgag | ggcatgtggt | gtttcagttg | ctccaaaatt | tacccaagtt | gaaggaagga | 1440 |
| tccttcaagc | cccaaagctg | aaagccggca | atggtgatga | tatcttttca | cgaaatggac | 1500 |
| ggtggaattt | cactaatagg | aagttttatg | aaacctgctc | tgtgaataag | tgggcggtcg | 1560 |
| ttaatttctc | tgcacgttgt | gatgttcgga | atcttatccg | tgacctgatg | aggaatgcat | 1620 |
| ctgcaaaggg | aattcaaatg | gaggaaccctt | ttgatgtgtt | tgaagagagt | ccctctatga | 1680 |
| ggcgtgcacc | tgtgtcaaga | agggtggatg | atatgtttgg | gcagataaaa | tcaaaacttc | 1740 |
| ctggagctcc | taggttcctc | ttgtgccttc | tccctgagag | gaaaaattgt | gaaatctatg | 1800 |
| gtccttggaa | gagaaagtgc | ctggccgagt | ttggtattgt | cacacagtgt | ctagctccat | 1860 |
| taagagtcaa | tgatccgtac | ctgcttaatt | tgctgatgaa | gatcaatgca | aagcttggtg | 1920 |
| gtctgaactc | gttgctgcaa | gttgaagcat | cttcgtcaat | accacatgtg | tcgcaagtac | 1980 |

-continued

```
ccaccatcat cttaggtatg gatgtttcac atggtcatcc aggacaagat agaccttcgg    2040
ttgcagcggt ggttagttct cgtcaatggc ctcttatctc tagatataga gcatcagtgc    2100
acacccaatc tgccagacta gaaatgatgt cctcgttgtt taagccgcgg ggtactgatg    2160
atgatggcct catccgggaa tcactgatcg acttccacac tagctctgga aagcgaaaac    2220
cagaacacat aattattttc agggatggag tcagtgaaag tcagtttacc caggtcatca    2280
acattgagct ggatcagatc atcgaggcat gtaagtttct ggatgagaag tggtcaccca    2340
agttcactgt gattgttgct caaaagaacc accacaccaa gttctttcag acggcatcac    2400 cagacaaatgt tcttcctgga actgtggtgg atagtaaagt ttgccatcct aagaacttcg    2460
acttctacat gtgtgcacat gctgggatga ttggaacaac aaggccgacc cactatcatg    2520
ttctgcacga cgagataggt ttcagtgccg acgagatgca ggagtttgtt cattcgctct    2580
cttacgtgta ccagaggagc acgacagcca tctcagttgt tgctccagtg tgctacgccc    2640
acctcgctgc agcccaggtg agcacgttcc tgagattgga ggagatgtca gacgcgtcct    2700
ccagccaggg aggagggcat acctcggctg gcagtgctcc tgtgccggag ctgcctcgcc    2760
tgcatgacaa agtcaggagc tccatgttct tctgctagct gatgtgcgtg cgcatcagga    2820
tcgagctcca tgttttgtgt tagtaaggcc tagttagtaa ggctgtagaa agaatgttta    2880
atgtttgcat gctaaagtcc aaacaatcaa aaccactact atatctacca gagcactgat    2940
cgatcaaaca acaagagtca gcatcaatca atcaaaaaaa aaaaaaaaaa aaaaaaaaa    3000 aaaaaaaaa                                                             3009
```

<210> SEQ ID NO 22
<211> LENGTH: 910
<212> TYPE: PRT
<213> ORGANISM: Zea mays

<400> SEQUENCE: 22

```
Met Gly Ser His Asp Gly Glu Asp Glu Leu Pro Pro Pro Pro
  1               5                  10                  15

Val Pro Pro Asp Val Ile Pro Ile Lys Ala Glu Asp Ala Val Gly Glu
                 20                  25                  30

Ser Pro Ala Asn His Ile Leu Lys Pro Lys Arg Leu Leu Met Asp Arg
             35                  40                  45

Pro Gly Ile Gly Arg Lys Gly Gln Pro Thr Gln Leu Tyr Ser Asn His
         50                  55                  60

Phe Lys Val Ala Val Lys Ser Thr Glu Asp Val Phe Phe His Tyr Tyr
 65                  70                  75                  80

Val Asn Leu Lys Tyr Glu Asp Asp Arg Pro Val Asp Gly Lys Gly Ile
                 85                  90                  95

Gly Arg Lys Val Ile Asp Lys Leu Gln Gln Thr Tyr Arg Ala Glu Leu
            100                 105                 110

Ser Asn Lys Asp Phe Ala Tyr Asp Gly Glu Lys Ser Leu Phe Thr Val
            115                 120                 125

Gly Gly Leu Pro Gln Lys Lys Asn Glu Phe Thr Val Val Leu Glu Asp
        130                 135                 140

Val Ser Thr Gly Lys Thr Ala Ala Asn Gly Ser Pro Gly Gly Asn Asp
145                 150                 155                 160

Ser Pro Gly Gly Gly Asp Arg Lys Arg Val Arg Pro Tyr Gln Thr
                165                 170                 175

Lys Thr Phe Lys Val Glu Ile Asn Phe Ala Ala Glu Val Pro Met Ser
            180                 185                 190
```

```
Ala Ile Gly Gln Val Ile Arg Gly Glu Glu Ser Glu Asn Ser Leu Glu
            195                 200                 205
Ala Leu Arg Val Leu Asp Ile Ile Leu Arg Gln His Ser Ala Glu Gln
        210                 215                 220
Gly Cys Leu Leu Val Lys Gln Ser Phe Phe Tyr Asn Asn Pro Ser Cys
225                 230                 235                 240
Phe Val Asp Leu Gly Gly Val Met Gly Cys Arg Gly Phe His Ser
                245                 250                 255
Ser Phe Arg Gly Thr Gln Ser Gly Leu Ser Leu Asn Val Asp Val Ser
            260                 265                 270
Thr Thr Met Ile Val Lys Pro Gly Pro Val Ile Asp Phe Leu Leu Ser
        275                 280                 285
Asn Gln Asn Val Asn Asp Pro Ser Arg Ile Asp Trp Gln Lys Ala Lys
        290                 295                 300
Arg Ala Leu Lys Gly Leu Arg Ile Arg Thr Thr Pro Ala Asn Ser Glu
305                 310                 315                 320
Phe Lys Ile Phe Gly Leu Ser Glu Arg Ile Cys Lys Glu Gln Thr Phe
                325                 330                 335
Pro Leu Arg Gln Arg Asn Gly Ser Asn Gly Asp Cys Asp Thr Ile Glu
            340                 345                 350
Ile Thr Val Tyr Asp Tyr Tyr Ala Lys Lys Gly Ile Asp Leu Lys Tyr
        355                 360                 365
Ser Gly Asp Phe Pro Cys Ile Asn Thr Gly Lys Ala Lys Arg Pro Thr
        370                 375                 380
Tyr Phe Pro Ile Glu Leu Cys Ser Leu Val Pro Leu Gln Arg Tyr Thr
385                 390                 395                 400
Lys Ala Leu Ser Thr Leu Gln Arg Ser Ser Leu Val Glu Lys Ser Arg
                405                 410                 415
Gln Lys Pro Glu Glu Arg Met Thr Val Leu Asn Asp Ala Leu Gln Arg
            420                 425                 430
Ser Asn Tyr Asp Ser Asp Pro Met Leu Arg Ala Cys Gly Val Ser Val
        435                 440                 445
Ala Pro Lys Phe Thr Gln Val Glu Gly Arg Ile Leu Gln Ala Pro Lys
        450                 455                 460
Leu Lys Ala Gly Asn Gly Asp Asp Ile Phe Ser Arg Asn Gly Arg Trp
465                 470                 475                 480
Asn Phe Thr Asn Arg Lys Phe Tyr Glu Thr Cys Ser Val Asn Lys Trp
                485                 490                 495
Ala Val Val Asn Phe Ser Ala Arg Cys Asp Val Arg Asn Leu Ile Arg
            500                 505                 510
Asp Leu Met Arg Asn Ala Ser Ala Lys Gly Ile Gln Met Glu Glu Pro
        515                 520                 525
Phe Asp Val Phe Glu Glu Ser Pro Ser Met Arg Arg Ala Pro Val Ser
        530                 535                 540
Arg Arg Val Asp Asp Met Phe Gly Gln Ile Lys Ser Lys Leu Pro Gly
545                 550                 555                 560
Ala Pro Arg Phe Leu Leu Cys Leu Leu Pro Glu Arg Lys Asn Cys Glu
                565                 570                 575
Ile Tyr Gly Pro Trp Lys Arg Lys Cys Leu Ala Glu Phe Gly Ile Val
            580                 585                 590
Thr Gln Cys Leu Ala Pro Leu Arg Val Asn Asp Pro Tyr Leu Leu Asn
        595                 600                 605
```

```
Leu Leu Met Lys Ile Asn Ala Lys Leu Gly Gly Leu Asn Ser Leu Leu
610                 615                 620
Gln Val Glu Ala Ser Ser Ile Pro His Val Ser Gln Val Pro Thr
625                 630                 635                 640
Ile Ile Leu Gly Met Asp Val Ser His Gly His Pro Gly Gln Asp Arg
                645                 650                 655
Pro Ser Val Ala Ala Val Val Ser Ser Arg Gln Trp Pro Leu Ile Ser
            660                 665                 670
Arg Tyr Arg Ala Ser Val His Thr Gln Ser Ala Arg Leu Glu Met Met
        675                 680                 685
Ser Ser Leu Phe Lys Pro Arg Gly Thr Asp Asp Gly Leu Ile Arg
690                 695                 700
Glu Ser Leu Ile Asp Phe His Thr Ser Ser Gly Lys Arg Lys Pro Glu
705                 710                 715                 720
His Ile Ile Ile Phe Arg Asp Gly Val Ser Glu Ser Gln Phe Thr Gln
                725                 730                 735
Val Ile Asn Ile Glu Leu Asp Gln Ile Ile Glu Ala Cys Lys Phe Leu
            740                 745                 750
Asp Glu Lys Trp Ser Pro Lys Phe Thr Val Ile Val Ala Gln Lys Asn
        755                 760                 765
His His Thr Lys Phe Phe Gln Thr Ala Ser Pro Asp Asn Val Leu Pro
    770                 775                 780
Gly Thr Val Val Asp Ser Lys Val Cys His Pro Lys Asn Phe Asp Phe
785                 790                 795                 800
Tyr Met Cys Ala His Ala Gly Met Ile Gly Thr Thr Arg Pro Thr His
                805                 810                 815
Tyr His Val Leu His Asp Glu Ile Gly Phe Ser Ala Asp Glu Met Gln
            820                 825                 830
Glu Phe Val His Ser Leu Ser Tyr Val Tyr Gln Arg Ser Thr Thr Ala
        835                 840                 845
Ile Ser Val Val Ala Pro Val Cys Tyr Ala His Leu Ala Ala Ala Gln
    850                 855                 860
Val Ser Thr Phe Leu Arg Leu Glu Glu Met Ser Asp Ala Ser Ser Ser
865                 870                 875                 880
Gln Gly Gly Gly His Thr Ser Ala Gly Ser Ala Pro Val Pro Glu Leu
                885                 890                 895
Pro Arg Leu His Asp Lys Val Arg Ser Ser Met Phe Phe Cys
            900                 905                 910

<210> SEQ ID NO 23
<211> LENGTH: 2429
<212> TYPE: DNA
<213> ORGANISM: Oryza sativa

<400> SEQUENCE: 23
aaaccattca agttcttgat gttgtcctta gggagtcacc atcttggaat tatgtcacag      60
tgtccagatc cttcttctct acccagtttg gtcaccgggg tgacattggt gagggacttg     120
agtgttggag aggttactat cagagcctgc gcccaacaca gatgggcctt tcgctgaata     180
tagatatatc tgcaacgtcc ttttttaagc ctgtgacagt gatccaattt gtggaggagt     240
tcctgaacat acgtgacacc tcaagacctt tgtcagaccg ggatcgtgtg aagataaaga     300
aagcattacg tggggttcgc attgaaacaa accaccaaga ggaccaaatc agaagataca     360
agataacagg gattaccccc attcctatga gccagctgat atttcctgtt gatgataatg     420
```

| | |
|---|---|
| ggacaaggaa gactgttgtt cagtacttct gggataggta caattacaga ctgaagtacg | 480 |
| cttcttggcc ctgcctacag tctggcagtg attctcgccc tgtatactta cctatggagg | 540 |
| tgtgcaagat tgtagaaggg cagaggtact ccaagaagct taatgacaaa caagtgacca | 600 |
| acatccttag agcaacctgt caacgccccc agcagaggga acagagcatt catgagatgg | 660 |
| ttctccacaa caagtataca gaggataggt ttgctcagga gttcggtatc aaggtctgca | 720 |
| atgacctagt ctctgttcca gcccgtgtgc tgcctccacc catgttgaag tatcatgatt | 780 |
| ctggaaggga gaaaacttgt gcacccagtg ttggacagtg aacatgatt aacaagaaaa | 840 |
| tgatcaatgg aggaactgtg gataactgga catgtctgag tttttcacga atgcgtcctg | 900 |
| aggaggtaca aggttctgt ggtgacctga ttcagatgtg caatgccact ggaatgtctt | 960 |
| tcaatccaag accagtcgtg gatgtccggt caacaaatcc taacaatata gagaatgctc | 1020 |
| tgagggatgt tcacaggaga acatcagaac tgctagccag agagggaaag ggaggcctgc | 1080 |
| agcttttaat tgtaattctg cctgaagtta gtggttctta tgggaaaatt aaaagggtct | 1140 |
| gtgagactga ccttggcatt gtatctcaat gttgtttgcc aaggcatgcc agcaggccga | 1200 |
| acaagcaata tttggaaaat gttgcactca aaatcaatgt caaggtcgga gggcgcaaca | 1260 |
| ctgttcttga gcgagccttt atccgcaatg gcataccatt tgtgtcagaa gtcccaacaa | 1320 |
| tcatctttgg cgctgatgtc acacaccctc cacctggaga ggactctgca tcatctattg | 1380 |
| ctgcggttgt ggcatctatg gattggcctg aaatcaccaa ataccgaggt ctggtctctg | 1440 |
| ctcaaccaca tagacaggag ataatagaag atctctttag tgttggtaaa gatccagtga | 1500 |
| aggttgtaaa tggtgggatg atcagggagt tgcttatcgc attccgcaag aagactggca | 1560 |
| gaaggcctga gaggataatc ttctatagag atggtgtaag tgaaggtcag ttcagccatg | 1620 |
| tgcttcttca tgaaatggat gccatcagaa aggcttgtgc atctttggag gagggatatc | 1680 |
| taccacctgt cacatttgta gtagttcaga aaaggcatca cacaaggctt ttcccagagg | 1740 |
| ttcatgggag gcgagacatg actgacaaga gcggaaacat ccttcctgga actgtcgtgg | 1800 |
| accgtcagat ttgccatcct acagagttcg atttctacct gtgtagccat gctggcatac | 1860 |
| agggtactag caggccaact cattaccatg tcctttacga tgagaaccat tttacagccg | 1920 |
| atgcacttca gtccctgacc aacaatcttt gctataccta tgcgcgatgc acccgggcag | 1980 |
| tgtctgtggt cccaccggcc tactatgctc atcttgctgc attccgcgct cgctactacg | 2040 |
| tggaaggaga gagttcggat ggtggctcga cccctggcag cagcgggcag gctgtggcgc | 2100 |
| gagagggccc tgtggaggtg cgccagcttc ccaagatcaa ggagaacgtc aaggacgtca | 2160 |
| tgttctactg ctgaggagat tgttggcaag gagagcccaa tattctggta gttttttggt | 2220 |
| tggtagactt gtttgtgtcc ttggtttgga gctggttgct tgtagttcca tttgctgttt | 2280 |
| ccgagtagcc ggattgtgac tgagcttttg tggtctttaa ggccttaact ctgcttgaga | 2340 |
| caatgcaagt cttttaaatt tccctgtggc taaaaagaa gaaaaacaag aaaaaaaaaa | 2400 |
| aaaaaaaaaa aaaaaaaaaa aaaaaaaaa | 2429 |

<210> SEQ ID NO 24
<211> LENGTH: 723
<212> TYPE: PRT
<213> ORGANISM: Oryza sativa
<400> SEQUENCE: 24

```
Thr Ile Gln Val Leu Asp Val Val Leu Arg Glu Ser Pro Ser Trp Asn
 1               5                  10                  15
```

```
Tyr Val Thr Val Ser Arg Ser Phe Phe Ser Thr Gln Phe Gly His Arg
             20                  25                  30

Gly Asp Ile Gly Glu Gly Leu Glu Cys Trp Arg Gly Tyr Tyr Gln Ser
         35                  40                  45

Leu Arg Pro Thr Gln Met Gly Leu Ser Leu Asn Ile Asp Ile Ser Ala
     50                  55                  60

Thr Ser Phe Phe Lys Pro Val Thr Val Ile Gln Phe Val Glu Glu Phe
 65                  70                  75                  80

Leu Asn Ile Arg Asp Thr Ser Arg Pro Leu Ser Asp Arg Asp Arg Val
                 85                  90                  95

Lys Ile Lys Lys Ala Leu Arg Gly Val Arg Ile Glu Thr Asn His Gln
            100                 105                 110

Glu Asp Gln Ile Arg Arg Tyr Lys Ile Thr Gly Ile Thr Pro Ile Pro
            115                 120                 125

Met Ser Gln Leu Ile Phe Pro Val Asp Asp Asn Gly Thr Arg Lys Thr
            130                 135                 140

Val Val Gln Tyr Phe Trp Asp Arg Tyr Asn Tyr Arg Leu Lys Tyr Ala
145                 150                 155                 160

Ser Trp Pro Cys Leu Gln Ser Gly Ser Asp Ser Arg Pro Val Tyr Leu
                165                 170                 175

Pro Met Glu Val Cys Lys Ile Val Glu Gly Gln Arg Tyr Ser Lys Lys
            180                 185                 190

Leu Asn Asp Lys Gln Val Thr Asn Ile Leu Arg Ala Thr Cys Gln Arg
            195                 200                 205

Pro Gln Gln Arg Glu Gln Ser Ile His Glu Met Val Leu His Asn Lys
210                 215                 220

Tyr Thr Glu Asp Arg Phe Ala Gln Glu Phe Gly Ile Lys Val Cys Asn
225                 230                 235                 240

Asp Leu Val Ser Val Pro Ala Arg Val Leu Pro Pro Met Leu Lys
                245                 250                 255

Tyr His Asp Ser Gly Arg Glu Lys Thr Cys Ala Pro Ser Val Gly Gln
                260                 265                 270

Trp Asn Met Ile Asn Lys Lys Met Ile Asn Gly Gly Thr Val Asp Asn
            275                 280                 285

Trp Thr Cys Leu Ser Phe Ser Arg Met Arg Pro Glu Glu Val Gln Arg
            290                 295                 300

Phe Cys Gly Asp Leu Ile Gln Met Cys Asn Ala Thr Gly Met Ser Phe
305                 310                 315                 320

Asn Pro Arg Pro Val Val Asp Val Arg Ser Thr Asn Pro Asn Asn Ile
                325                 330                 335

Glu Asn Ala Leu Arg Asp Val His Arg Arg Thr Ser Glu Leu Leu Ala
                340                 345                 350

Arg Glu Gly Lys Gly Gly Leu Gln Leu Leu Ile Val Ile Leu Pro Glu
            355                 360                 365

Val Ser Gly Ser Tyr Gly Lys Ile Lys Arg Val Cys Glu Thr Asp Leu
            370                 375                 380

Gly Ile Val Ser Gln Cys Cys Leu Pro Arg His Ala Ser Arg Pro Asn
385                 390                 395                 400

Lys Gln Tyr Leu Glu Asn Val Ala Leu Lys Ile Asn Val Lys Val Gly
                405                 410                 415

Gly Arg Asn Thr Val Leu Glu Arg Ala Phe Ile Arg Asn Gly Ile Pro
            420                 425                 430

Phe Val Ser Glu Val Pro Thr Ile Ile Phe Gly Ala Asp Val Thr His
```

```
                435                 440                 445
Pro Pro Pro Gly Glu Asp Ser Ala Ser Ser Ile Ala Ala Val Val Ala
    450                 455                 460

Ser Met Asp Trp Pro Glu Ile Thr Lys Tyr Arg Gly Leu Val Ser Ala
465                 470                 475                 480

Gln Pro His Arg Gln Glu Ile Ile Glu Asp Leu Phe Ser Val Gly Lys
                485                 490                 495

Asp Pro Val Lys Val Val Asn Gly Gly Met Ile Arg Glu Leu Leu Ile
            500                 505                 510

Ala Phe Arg Lys Lys Thr Gly Arg Arg Pro Glu Arg Ile Ile Phe Tyr
        515                 520                 525

Arg Asp Gly Val Ser Glu Gly Gln Phe Ser His Val Leu Leu His Glu
    530                 535                 540

Met Asp Ala Ile Arg Lys Ala Cys Ala Ser Leu Glu Glu Gly Tyr Leu
545                 550                 555                 560

Pro Pro Val Thr Phe Val Val Gln Lys Arg His His Thr Arg Leu
                565                 570                 575

Phe Pro Glu Val His Gly Arg Arg Asp Met Thr Asp Lys Ser Gly Asn
            580                 585                 590

Ile Leu Pro Gly Thr Val Val Asp Arg Gln Ile Cys His Pro Thr Glu
        595                 600                 605

Phe Asp Phe Tyr Leu Cys Ser His Ala Gly Ile Gln Gly Thr Ser Arg
    610                 615                 620

Pro Thr His Tyr His Val Leu Tyr Asp Glu Asn His Phe Thr Ala Asp
625                 630                 635                 640

Ala Leu Gln Ser Leu Thr Asn Asn Leu Cys Tyr Thr Tyr Ala Arg Cys
                645                 650                 655

Thr Arg Ala Val Ser Val Val Pro Pro Ala Tyr Tyr Ala His Leu Ala
            660                 665                 670

Ala Phe Arg Ala Arg Tyr Tyr Val Glu Gly Glu Ser Ser Asp Gly Gly
        675                 680                 685

Ser Thr Pro Gly Ser Ser Gly Gln Ala Val Ala Arg Glu Gly Pro Val
    690                 695                 700

Glu Val Arg Gln Leu Pro Lys Ile Lys Glu Asn Val Lys Asp Val Met
705                 710                 715                 720

Phe Tyr Cys

<210> SEQ ID NO 25
<211> LENGTH: 1619
<212> TYPE: DNA
<213> ORGANISM: Oryza sativa

<400> SEQUENCE: 25
cttacattct ggaagggtga gagtatgcac gccagaggat ggggcgtgga acatgaaaga      60
caagaaagta gttaacggtg ctacaattaa aagctgggca tgtgtcaact tgtgcgaggg     120
tttggataat cgtgttgttg aagcattctg ccttcaattg gtcagaacgt ccaaaataac     180
tggactggac tttgcgaatg tgagccttcc aatattgaaa gctgatcctc ataatgttaa     240
aactgatctt cctatgcgct atcaggaagc atgcagctgg tcgagggata acaagattga     300
cctcctactt gttgtaatga cagatgataa aaataatgcc agcttatatg gtgacgttaa     360
aagaatctgt gaaacagaaa tcggtgtatt gtcacagtgt tgtcgagcga agcaagtcta     420
caaggagagg aatgttcagt actgcgcaaa tgttgctctt aagatcaatg ccaaggctgg     480
```

```
aggaaggaac tcggtatttc ttaatgtaga agcaagttta ccggttgttt caaagagccc      540
aactattata tttggtgctg atgttaccca tcctgggtcc tttgatgaaa gtaccccttc      600
cattgcttcg gttgttgctt ccgcagactg gcctgaggtg accaagtata attctgttgt      660
tcgtatgcaa gcttctcgta aggagattat acaagatctt gatagcattg ttagggaact      720
tctcaatgca ttcaaaaggg actccaagat ggagccgaag cagctcattt tctacaggga      780
cggcgtaagc gagggtcagt tccagcaagt tgtagagagc gaaataccgg agatagaaaa      840
ggcttggaag tctctgtatg ctggcaagcc acgaattacc ttcatagtgg tgcagaagag      900
gcatcataca aggctgttcc ccaacaatta caatgatcca cgcggcatgg atgggactgg      960
aaatgttcgt ccaggcacag tagttgatac agtgatctgt caccctcgag agtttgattt     1020
cttcctgtgc agccaagccg ggatcaaagg acaagccgt cctagccatt accatgtgct     1080
gcgcgacgac aacaacttca ccgcagatca gcttcagtct gtcacaaaca acctgtgcta     1140
cttatataca agctgcactc gctcggtgtc tattccacct cctgtttact acgctcataa     1200
gctcgcattc cgcgctcgtt tctacctcac ccaagttccc gtcgccggtg agatccagg      1260 tgctgctaag ttccagtggg tacttccaga gattaaggaa gaggtgaaaa agtccatgtt     1320
cttttgctag tcgtccttgt gcccccctga aactgaagcc tggagccagc cggcaagctc     1380
tggaaatgct ctgaataatc aaacttggaa gaataagcac ctgcccaggt tgccattcgt     1440
ttccatgtgg catggaggat ggcatcctga aaggatatt gtcatgtttg tgtggttttt      1500
aaacgacatt gaagtttatc tccggtgtta ctatctcagc actttggatg ttttatttg      1560 ttatgtctga agatatagac acaaaacttc attttgtttt caaaaaaaaa aaaaaaaaa      1619
```

<210> SEQ ID NO 26
<211> LENGTH: 442
<212> TYPE: PRT
<213> ORGANISM: Oryza sativa

<400> SEQUENCE: 26

```
Leu His Ser Gly Arg Val Arg Val Cys Thr Pro Glu Asp Gly Ala Trp
 1               5                  10                  15

Asn Met Lys Asp Lys Val Val Asn Gly Ala Thr Ile Lys Ser Trp
            20                  25                  30

Ala Cys Val Asn Leu Cys Glu Gly Leu Asp Asn Arg Val Val Glu Ala
        35                  40                  45

Phe Cys Leu Gln Leu Val Arg Thr Ser Lys Ile Thr Gly Leu Asp Phe
    50                  55                  60

Ala Asn Val Ser Leu Pro Ile Leu Lys Ala Asp Pro His Asn Val Lys
65                  70                  75                  80

Thr Asp Leu Pro Met Arg Tyr Gln Glu Ala Cys Ser Trp Ser Arg Asp
                85                  90                  95

Asn Lys Ile Asp Leu Leu Leu Val Met Thr Asp Asp Lys Asn Asn
            100                 105                 110

Ala Ser Leu Tyr Gly Asp Val Lys Arg Ile Cys Glu Thr Glu Ile Gly
        115                 120                 125

Val Leu Ser Gln Cys Cys Arg Ala Lys Gln Val Tyr Lys Glu Arg Asn
    130                 135                 140

Val Gln Tyr Cys Ala Asn Val Ala Leu Lys Ile Asn Ala Lys Ala Gly
145                 150                 155                 160

Gly Arg Asn Ser Val Phe Leu Asn Val Glu Ala Ser Leu Pro Val Val
                165                 170                 175
```

```
Ser Lys Ser Pro Thr Ile Ile Phe Gly Ala Asp Val Thr His Pro Gly
            180                 185                 190

Ser Phe Asp Glu Ser Thr Pro Ser Ile Ala Ser Val Val Ala Ser Ala
        195                 200                 205

Asp Trp Pro Glu Val Thr Lys Tyr Asn Ser Val Arg Met Gln Ala
    210                 215                 220

Ser Arg Lys Glu Ile Ile Gln Asp Leu Asp Ser Ile Val Arg Glu Leu
225                 230                 235                 240

Leu Asn Ala Phe Lys Arg Asp Ser Lys Met Glu Pro Lys Gln Leu Ile
                245                 250                 255

Phe Tyr Arg Asp Gly Val Ser Glu Gly Gln Phe Gln Gln Val Val Glu
            260                 265                 270

Ser Glu Ile Pro Glu Ile Glu Lys Ala Trp Lys Ser Leu Tyr Ala Gly
            275                 280                 285

Lys Pro Arg Ile Thr Phe Ile Val Gln Lys Arg His His Thr Arg
    290                 295                 300

Leu Phe Pro Asn Asn Tyr Asn Asp Pro Arg Gly Met Asp Gly Thr Gly
305                 310                 315                 320

Asn Val Arg Pro Gly Thr Val Val Asp Thr Val Ile Cys His Pro Arg
                325                 330                 335

Glu Phe Asp Phe Phe Leu Cys Ser Gln Ala Gly Ile Lys Gly Thr Ser
            340                 345                 350

Arg Pro Ser His Tyr His Val Leu Arg Asp Asp Asn Asn Phe Thr Ala
            355                 360                 365

Asp Gln Leu Gln Ser Val Thr Asn Asn Leu Cys Tyr Leu Tyr Thr Ser
    370                 375                 380

Cys Thr Arg Ser Val Ser Ile Pro Pro Val Tyr Tyr Ala His Lys
385                 390                 395                 400

Leu Ala Phe Arg Ala Arg Phe Tyr Leu Thr Gln Val Pro Val Ala Gly
                405                 410                 415

Gly Asp Pro Gly Ala Ala Lys Phe Gln Trp Val Leu Pro Glu Ile Lys
            420                 425                 430

Glu Glu Val Lys Lys Ser Met Phe Phe Cys
            435                 440
```

<210> SEQ ID NO 27
<211> LENGTH: 3549
<212> TYPE: DNA
<213> ORGANISM: Oryza sativa

<400> SEQUENCE: 27

```
gttggacaac gggtactact cccatcaagc tttagccatg atgagaaaga aaaaaactga      60
accccgtaat gctggggaaa gttctggaac tcaacaagcc actggagctc ctggacgggg     120
tccttcacag cgacctgaga gagctcaaca gcatggaggt ggtggttggc agcctgccaa     180
tcctcaatat gctcaacaag ctggtcgtgg tggtggacaa caccagggac gtggtggacg     240
ttaccagggt cgtggagggc aacatcaca tcaaccaggt ggtggtccgg ttgaatatca      300
agcacatgag tactatggcc gtggtgtcca acggcaagga ggaatgccac aacacaggag     360
tggcagtggt ggacatggag ttcctgccag tccatcaaga cagttcccg agctgcacca      420
agcctcacaa gaccagtacc aagctacggt ggttgcacca tcaccatcaa gaactggccc     480
atcttcgctg cctgttgagg ccagcagcga agaagtccaa catcagtttc aggaacttgc     540
catccagggt caaagcccca ctagccaggc cattcaacca gcaccaccat cgagcaaatc     600
```

```
agtgagattt ccaatgcgcc ctggcaaggg tacatttggt gataggtgca tcgtgaaagc    660
caaccatttc tttgctgaat tgcctgacaa agaccttcac cagtatgatg tgtctataac    720
tcctgaggtt ccttcacgtg gtgtcaatcg tgctgtcatt ggagaaattg taacacaata    780
taggcagtct catttgggtg gccgtcttcc agtctatgat ggaaggaaga gcttatacac    840
agctggtcca ttaccattta cttctaggac ctttgacgtt attctgcagg atgaggaaga    900
gagccttgct gttgggcaag gtgcacagag gcgtgagaga ccatttaagg tcgtgatcaa    960
atttgctgca cgcgctgatc tccaccattt agccatgttt ttagctggaa ggcaagcgga   1020
tgctcctcaa gaagctcttc aagttcttga cattgttcta cgtgaattgc ctactgcaag   1080
gtactctcca gttgcaaggt catttttattc gcctaactta ggaaggcgcc aacaacttgg   1140
cgagggcctg gaaagttggc gtggttttta ccaaagcata cgacccacgc agatgggact   1200
ttctctgaat attgatatgt catcgacagc attcattgag cctctacctg tgattgactt   1260
tgttgcacag cttttgaaca gagacatctc agttagacca ttatctgatg ctgatcgtgt   1320
gaagatcaag aaggccctaa ggggtgtaaa ggttgaggtc acacatagag gcaatatgcg   1380
caggaagtat cgcatttctg gccttacctc gcaagcaaca cgagagttgt cttttcccat   1440
tgataatcat ggtactgtga agacggtggt gcaatacttc caggagacat atggatttaa   1500
cattaagcac acaactttgc cttgcttgca agtgggcaat caacaaaggc caaattatct   1560
accaatggag gtctgtaaga ttgtggaggg acagcgttac tcaaaaagac taaatgagaa   1620
gcagataact gctcttctta aagtgacctg ccagcgccct caagagcgtg agctggacat   1680
tttgcagact gtgcatcaca atgcatacca tcaggatcca tatgcacagg agtttggcat   1740
aaggatcgat gagcgacttg catctgttga agctcgtgtt ctaccacccc cctggcttaa   1800
gtaccacgat agtggcagag agaaggatgt cttgccaaga attggccaat ggaatatgat   1860
gaataagaaa atggtcaatg gtggtagagt taacaactgg acatgcatca ttttttctcg   1920
tcatgtccaa gataatgctg ctaggagttt ctgtcgcgag cttgctatta tgtgccaaat   1980
atctgggatg gacttctcaa ttgatcctgt ggttcctcta gtgactgcaa gacctgaaca   2040
tgtggaaaga gcgctcaagg cacgctatca agaggccatg aatatactga aaccacaggg   2100
cggggagctt gacctgctga ttgcaatatt gcctgacaat aatggttctc tttatggcga   2160
tctcaaaagg atatgtgaga ctgatcttgg attggtctcg caatgctgtc ttacgaagca   2220
tgtttttaag atgagcaaac agtatttagc aaacgttgcc cttaaaatca atgttaaggt   2280
gggaggaaga aatacagtac ttgttgatgc tttgacaagg aggattcccc ttgtcagtga   2340
cagaccaact atcatatttg gtgcggatgt tactcatcct catcctggag aagattccag   2400
tccttccatt gcagctgtgg ttgcttctca agactggcct gaagtcacta agtatgctgg   2460
attggtgagt gcccaagccc atcgtcaaga attgatacaa gatcttttca agtatggca   2520
agacccgcat agaggaactg ttactggtgg catgatcaag gagcttctca tttctttcaa   2580
gagggctact ggacagaaac ctcagaggat aatattttac agggatggtg tcagcgaggg   2640
gcagttttat caagttttgt tgtatgagct tgatgccatt agaaaggctt gtgcatccct   2700
ggaacccaac tatcagcctc cagttacctt tgtggtggtc cagaagcggc atcacacaag   2760
gttgtttgct aataatcaca acgaccagcg tactgttgat agaagtggaa acattctgcc   2820
tggaactgtt gttgactcaa agatttgcca tccaaccgag tttgatttct acctgtgtag   2880
ccatgctggc atacagggaa caagccgtcc tgctcattat catgttctgt gggatgagaa   2940
caaatttact gcagacgagt tgcaaacccct cacgaacaac ttgtgctaca cgtatgcaag   3000
```

-continued

```
gtgcactcgc tctgtatcaa ttgtgcctcc tgcgtactat gctcatctgg cagccttccg    3060
agctcgcttt tacatggagc cagagacatc tgacagtgga tcaatggcga gtggagctgc    3120
aacgagccgt ggccttccac caggtgtgcg cagcgccagg gttgctggaa atgtagccgt    3180
caggcctcta cctgctctca aggaaaacgt gaagcgtgtc atgttttact gctaagagct    3240
tgggctgtac cccgtatgcg ccaaggaatg tagtactatg ttatgttatt ttagcacttg    3300
cactctgtcg ttgatcccgt taaaacgggt atgctaccat aagctgttgg actattctgg    3360
gtattgtagt actacttgtt ttgtatttgt gtttgtgacg ctgcagagcg tgaacaacgc    3420
aagtctggta cttgtatcgt tgtgtttgtg ggaacctaaa tcttgttgga cctttgttgt    3480
gcttgaagaa ccaagttaaa taatcctgtc agtataggga tttaattgca aaaaaaaaa    3540 aaaaaaaa                                                             3549
```

<210> SEQ ID NO 28
<211> LENGTH: 1065
<212> TYPE: PRT
<213> ORGANISM: Oryza sativa

<400> SEQUENCE: 28

```
Met Met Arg Lys Lys Thr Glu Pro Arg Asn Ala Gly Glu Ser Ser
 1               5                  10                  15

Gly Thr Gln Gln Ala Thr Gly Ala Pro Gly Arg Gly Pro Ser Gln Arg
                20                  25                  30

Pro Glu Arg Ala Gln Gln His Gly Gly Gly Trp Gln Pro Ala Asn
            35                  40                  45

Pro Gln Tyr Ala Gln Gln Ala Gly Arg Gly Gly Gln His Gln Gly
        50                  55                  60

Arg Gly Gly Arg Tyr Gln Gly Arg Gly Pro Thr Ser His Gln Pro
 65                  70                  75                  80

Gly Gly Gly Pro Val Glu Tyr Gln Ala His Glu Tyr Tyr Gly Arg Gly
                85                  90                  95

Val Gln Arg Gln Gly Gly Met Pro Gln His Arg Ser Gly Ser Gly Gly
                100                 105                 110

His Gly Val Pro Ala Ser Pro Ser Arg Thr Val Pro Glu Leu His Gln
            115                 120                 125

Ala Ser Gln Asp Gln Tyr Gln Ala Thr Val Val Ala Pro Ser Pro Ser
        130                 135                 140

Arg Thr Gly Pro Ser Ser Leu Pro Val Glu Ala Ser Ser Glu Val
145                 150                 155                 160

Gln His Gln Phe Gln Glu Leu Ala Ile Gln Gly Gln Ser Pro Thr Ser
                165                 170                 175

Gln Ala Ile Gln Pro Ala Pro Ser Ser Lys Ser Val Arg Phe Pro
            180                 185                 190

Met Arg Pro Gly Lys Gly Thr Phe Gly Asp Arg Cys Ile Val Lys Ala
        195                 200                 205

Asn His Phe Phe Ala Glu Leu Pro Asp Lys Asp Leu His Gln Tyr Asp
        210                 215                 220

Val Ser Ile Thr Pro Glu Val Pro Ser Arg Gly Val Asn Arg Ala Val
225                 230                 235                 240

Ile Gly Glu Ile Val Thr Gln Tyr Arg Gln Ser His Leu Gly Arg
                245                 250                 255

Leu Pro Val Tyr Asp Gly Arg Lys Ser Leu Tyr Thr Ala Gly Pro Leu
                260                 265                 270
```

```
Pro Phe Thr Ser Arg Thr Phe Asp Val Ile Leu Gln Asp Glu Glu Glu
        275                 280                 285

Ser Leu Ala Val Gly Gln Gly Ala Gln Arg Arg Glu Arg Pro Phe Lys
    290                 295                 300

Val Val Ile Lys Phe Ala Ala Arg Ala Asp Leu His His Leu Ala Met
305                 310                 315                 320

Phe Leu Ala Gly Arg Gln Ala Asp Ala Pro Gln Glu Ala Leu Gln Val
                325                 330                 335

Leu Asp Ile Val Leu Arg Glu Leu Pro Thr Ala Arg Tyr Ser Pro Val
            340                 345                 350

Ala Arg Ser Phe Tyr Ser Pro Asn Leu Gly Arg Gln Gln Leu Gly
        355                 360                 365

Glu Gly Leu Glu Ser Trp Arg Gly Phe Tyr Gln Ser Ile Arg Pro Thr
    370                 375                 380

Gln Met Gly Leu Ser Leu Asn Ile Asp Met Ser Ser Thr Ala Phe Ile
385                 390                 395                 400

Glu Pro Leu Pro Val Ile Asp Phe Val Ala Gln Leu Leu Asn Arg Asp
                405                 410                 415

Ile Ser Val Arg Pro Leu Ser Asp Ala Asp Arg Val Lys Ile Lys Lys
            420                 425                 430

Ala Leu Arg Gly Val Lys Val Glu Val Thr His Arg Gly Asn Met Arg
        435                 440                 445

Arg Lys Tyr Arg Ile Ser Gly Leu Thr Ser Gln Ala Thr Arg Glu Leu
    450                 455                 460

Ser Phe Pro Ile Asp Asn His Gly Thr Val Lys Thr Val Val Gln Tyr
465                 470                 475                 480

Phe Gln Glu Thr Tyr Gly Phe Asn Ile Lys His Thr Thr Leu Pro Cys
                485                 490                 495

Leu Gln Val Gly Asn Gln Gln Arg Pro Asn Tyr Leu Pro Met Glu Val
            500                 505                 510

Cys Lys Ile Val Glu Gly Gln Arg Tyr Ser Lys Arg Leu Asn Glu Lys
        515                 520                 525

Gln Ile Thr Ala Leu Leu Lys Val Thr Cys Gln Arg Pro Gln Glu Arg
    530                 535                 540

Glu Leu Asp Ile Leu Gln Thr Val His His Asn Ala Tyr His Gln Asp
545                 550                 555                 560

Pro Tyr Ala Gln Glu Phe Gly Ile Arg Ile Asp Glu Arg Leu Ala Ser
                565                 570                 575

Val Glu Ala Arg Val Leu Pro Pro Trp Leu Lys Tyr His Asp Ser
            580                 585                 590

Gly Arg Glu Lys Asp Val Leu Pro Arg Ile Gly Gln Trp Asn Met Met
        595                 600                 605

Asn Lys Lys Met Val Asn Gly Gly Arg Val Asn Asn Trp Thr Cys Ile
    610                 615                 620

Asn Phe Ser Arg His Val Gln Asp Asn Ala Ala Arg Ser Phe Cys Arg
625                 630                 635                 640

Glu Leu Ala Ile Met Cys Gln Ile Ser Gly Met Asp Phe Ser Ile Asp
                645                 650                 655

Pro Val Val Pro Leu Val Thr Ala Arg Pro Glu His Val Glu Arg Ala
            660                 665                 670

Leu Lys Ala Arg Tyr Gln Glu Ala Met Asn Ile Leu Lys Pro Gln Gly
        675                 680                 685
```

Gly Glu Leu Asp Leu Leu Ile Ala Ile Leu Pro Asp Asn Asn Gly Ser
690                 695                 700

Leu Tyr Gly Asp Leu Lys Arg Ile Cys Glu Thr Asp Leu Gly Leu Val
705                 710                 715                 720

Ser Gln Cys Cys Leu Thr Lys His Val Phe Lys Met Ser Lys Gln Tyr
            725                 730                 735

Leu Ala Asn Val Ala Leu Lys Ile Asn Val Lys Val Gly Gly Arg Asn
            740                 745                 750

Thr Val Leu Val Asp Ala Leu Thr Arg Arg Ile Pro Leu Val Ser Asp
        755                 760                 765

Arg Pro Thr Ile Ile Phe Gly Ala Asp Val Thr His Pro His Pro Gly
770                 775                 780

Glu Asp Ser Ser Pro Ser Ile Ala Ala Val Val Ala Ser Gln Asp Trp
785                 790                 795                 800

Pro Glu Val Thr Lys Tyr Ala Gly Leu Val Ser Ala Gln Ala His Arg
                805                 810                 815

Gln Glu Leu Ile Gln Asp Leu Phe Lys Val Trp Gln Asp Pro His Arg
            820                 825                 830

Gly Thr Val Thr Gly Gly Met Ile Lys Glu Leu Leu Ile Ser Phe Lys
        835                 840                 845

Arg Ala Thr Gly Gln Lys Pro Gln Arg Ile Ile Phe Tyr Arg Asp Gly
850                 855                 860

Val Ser Glu Gly Gln Phe Tyr Gln Val Leu Leu Tyr Glu Leu Asp Ala
865                 870                 875                 880

Ile Arg Lys Ala Cys Ala Ser Leu Glu Pro Asn Tyr Gln Pro Pro Val
                885                 890                 895

Thr Phe Val Val Val Gln Lys Arg His His Thr Arg Leu Phe Ala Asn
            900                 905                 910

Asn His Asn Asp Gln Arg Thr Val Asp Arg Ser Gly Asn Ile Leu Pro
        915                 920                 925

Gly Thr Val Val Asp Ser Lys Ile Cys His Pro Thr Glu Phe Asp Phe
930                 935                 940

Tyr Leu Cys Ser His Ala Gly Ile Gln Gly Thr Ser Arg Pro Ala His
945                 950                 955                 960

Tyr His Val Leu Trp Asp Glu Asn Lys Phe Thr Ala Asp Glu Leu Gln
                965                 970                 975

Thr Leu Thr Asn Asn Leu Cys Tyr Thr Tyr Ala Arg Cys Thr Arg Ser
            980                 985                 990

Val Ser Ile Val Pro Pro Ala Tyr Tyr Ala His Leu Ala Ala Phe Arg
        995                 1000                1005

Ala Arg Phe Tyr Met Glu Pro Glu Thr Ser Asp Ser Gly Ser Met Ala
1010                1015                1020

Ser Gly Ala Ala Thr Ser Arg Gly Leu Pro Pro Gly Val Arg Ser Ala
1025                1030                1035                1040

Arg Val Ala Gly Asn Val Ala Val Arg Pro Leu Pro Ala Leu Lys Glu
                1045                1050                1055

Asn Val Lys Arg Val Met Phe Tyr Cys
            1060                1065

<210> SEQ ID NO 29
<211> LENGTH: 772
<212> TYPE: DNA
<213> ORGANISM: Oryza sativa

<400> SEQUENCE: 29

```
gttctaaccg ccggccgccg ccctccccgc acgacgccga cgccgccctc ctcgcccaac    60
gccggctcag cccttctcc tcccgcccg acgccgcccc ttctcctccc cgtcccacgc    120
cgaccccgcc cgacgccggc gccactctgc ttgtccccgg ccggcgccga gcctgctcct    180
ccccgcccga cgccggcgcc gccgacgctg ctctgctcct ccccgaccgg cgccgacctg    240
ctcctcccag cccggagccc gacgccggca catctcatcc agatgtccga taacatggct    300
gccaaaattg gtgaaattgt ccaagtacat aatgataatc ctgtaaagag agtacctatt    360
gcacgaccta gctttggccg tgaaggaaag caaatcaagc tgctctcaaa ccacttcact    420
gtgaagctta gtggaattga tgcggttttc taccaataca gtgtttccat caaatctgag    480
gatgataagg tgattgatgg aaagggtatt ggccgaaagg tcatggataa agtgctgcaa    540
acatacagct ctgagcttgc tgggaaggaa tttgcgtatg atggtgaaaa atgtctattt    600
actgtggggc ctcttccaca gaacaacttt gagttcactg ttatcttgga ggaaacatct    660
tcaagagctg ctggtgggag tctagggcat ggaagcccta atcaaggtga catcaaaaaa    720
aaaaaaaaaa aaaaaaaaaa aaaaaaaaaa gaaaaaaaaa aaaaaaaaaa aa           772
```

<210> SEQ ID NO 30
<211> LENGTH: 238
<212> TYPE: PRT
<213> ORGANISM: Oryza sativa

<400> SEQUENCE: 30

```
Val Leu Thr Ala Gly Arg Arg Pro Pro Arg Thr Thr Pro Thr Pro Pro
 1               5                  10                  15

Ser Ser Pro Asn Ala Gly Ser Ala Pro Ser Pro Pro Arg Pro Thr Pro
            20                  25                  30

Pro Leu Leu Leu Pro Val Pro Arg Arg Pro Arg Pro Thr Pro Ala Pro
        35                  40                  45

Leu Cys Leu Ser Pro Ala Gly Ala Glu Pro Ala Pro Pro Arg Pro Thr
    50                  55                  60

Pro Ala Pro Pro Thr Leu Leu Cys Ser Ser Pro Thr Gly Ala Asp Leu
65                  70                  75                  80

Leu Leu Pro Ala Arg Ser Pro Thr Pro Ala His Leu Ile Gln Met Ser
                85                  90                  95

Asp Asn Met Ala Ala Lys Ile Gly Glu Ile Val Gln Val His Asn Asp
            100                 105                 110

Asn Pro Val Lys Arg Val Pro Ile Ala Arg Pro Ser Phe Gly Arg Glu
        115                 120                 125

Gly Lys Gln Ile Lys Leu Leu Ser Asn His Phe Thr Val Lys Leu Ser
    130                 135                 140

Gly Ile Asp Ala Val Phe Tyr Gln Tyr Ser Val Ser Ile Lys Ser Glu
145                 150                 155                 160

Asp Asp Lys Val Ile Asp Gly Lys Gly Ile Gly Arg Lys Val Met Asp
                165                 170                 175

Lys Val Leu Gln Thr Tyr Ser Ser Glu Leu Ala Gly Lys Glu Phe Ala
            180                 185                 190

Tyr Asp Gly Glu Lys Cys Leu Phe Thr Val Gly Pro Leu Pro Gln Asn
        195                 200                 205

Asn Phe Glu Phe Thr Val Ile Leu Glu Glu Thr Ser Ser Arg Ala Ala
    210                 215                 220

Gly Gly Ser Leu Gly His Gly Ser Pro Asn Gln Gly Asp Ile
225                 230                 235
```

<210> SEQ ID NO 31
<211> LENGTH: 1238
<212> TYPE: DNA
<213> ORGANISM: Oryza sativa

<400> SEQUENCE: 31

```
tcacaatgct gttgcacgaa gcaggtgttc aaaatgaaca acaaattct tgcaaatctt        60
gctctgaaga taaatgtcaa ggttgggggc aggaacactg tgctggtgga tgctgtgtca      120
aggcgtattc ctctggtaac cgacagacct acaattatat ttggtgctga tgttacccat      180
cctcatcctg gagaggacag cagtccctca attgctgctg ttgtagcctc ccaagattgg      240
cctgaggtga caaagtatgc tgggttggtt tctgctcaag cccaccgaca gagctgata      300
gaagatctat ataaaatctg gcaggatcca cagagaggaa cagttagtgg tggcatgatc      360
cgtgagctgc ttatatcctt caaaagatca actggtgaga agccccagcg aataatattt      420
tacagggatg gcgttagtga aggccaattt taccaagttc tactttatga attgaatgca      480
atccgaaaag catgtgcctc cctggagaca aattaccaac caaggtgac tttcattgtg       540
gttcagaaac gtcaccacac aagattattt gcacataatc acaacgatca gaactcagtt      600
gacaggagcg ggaacatact ccctggtacg gttgtagatt caaagatctg tcatccaact      660
gagtttgact tctacctgtg tagccatgct ggcattaagg gtactagtcg tccagctcat      720
tatcatgtct tgtgggatga aaacaacttc acagctgatg cattgcagat tcttaccaac      780
aaccttttgct acaccatgc aaggtgcact cgctctgtat caattgttcc acctgcttat      840
tatgctcatc tggctgcctt ccgtgctcgt ttctatatgg aaccagatac atctgacagc      900
agctctgtcg ttagtgggcc tggtgtacgt gggccacttt ctggctcatc aacatcacgt      960
actcgggccc ctggtggtgc agctgttaag ccacttcctg ctctgaagga tagtgtgaag     1020
agggtcatgt tctactgctg aagctagggc ctacatagct aaagctcttc gtttcttggc     1080
aacctgccta tgatggttgt aattatgtgt caaaaaatcc cataataatc tgccagctgc     1140
tatcttctcc attgtactat gctggtcatg tttgccaaag ttaccctata tgtatgtata     1200
ttatgctatt gttttttttaa aaaaaaaaa aaaaaaaa                               1238
```

<210> SEQ ID NO 32
<211> LENGTH: 346
<212> TYPE: PRT
<213> ORGANISM: Oryza sativa

<400> SEQUENCE: 32

Ser Gln Cys Cys Cys Thr Lys Gln Val Phe Lys Met Asn Lys Gln Ile
1               5                   10                  15

Leu Ala Asn Leu Ala Leu Lys Ile Asn Val Lys Val Gly Gly Arg Asn
            20                  25                  30

Thr Val Leu Val Asp Ala Val Ser Arg Arg Ile Pro Leu Val Thr Asp
        35                  40                  45

Arg Pro Thr Ile Ile Phe Gly Ala Asp Val Thr His Pro His Pro Gly
    50                  55                  60

Glu Asp Ser Ser Pro Ser Ile Ala Ala Val Val Ala Ser Gln Asp Trp
65                  70                  75                  80

Pro Glu Val Thr Lys Tyr Ala Gly Leu Val Ser Ala Gln Ala His Arg
                85                  90                  95

Gln Glu Leu Ile Glu Asp Leu Tyr Lys Ile Trp Gln Asp Pro Gln Arg
            100                 105                 110

Gly Thr Val Ser Gly Gly Met Ile Arg Glu Leu Leu Ile Ser Phe Lys
        115                 120                 125

Arg Ser Thr Gly Glu Lys Pro Gln Arg Ile Ile Phe Tyr Arg Asp Gly
        130                 135                 140

Val Ser Glu Gly Gln Phe Tyr Gln Val Leu Leu Tyr Glu Leu Asn Ala
145                 150                 155                 160

Ile Arg Lys Ala Cys Ala Ser Leu Glu Thr Asn Tyr Gln Pro Lys Val
                165                 170                 175

Thr Phe Ile Val Val Gln Lys Arg His His Thr Arg Leu Phe Ala His
            180                 185                 190

Asn His Asn Asp Gln Asn Ser Val Asp Arg Ser Gly Asn Ile Leu Pro
        195                 200                 205

Gly Thr Val Val Asp Ser Lys Ile Cys His Pro Thr Glu Phe Asp Phe
    210                 215                 220

Tyr Leu Cys Ser His Ala Gly Ile Lys Gly Thr Ser Arg Pro Ala His
225                 230                 235                 240

Tyr His Val Leu Trp Asp Glu Asn Asn Phe Thr Ala Asp Ala Leu Gln
                245                 250                 255

Ile Leu Thr Asn Asn Leu Cys Tyr Thr Tyr Ala Arg Cys Thr Arg Ser
            260                 265                 270

Val Ser Ile Val Pro Pro Ala Tyr Tyr Ala His Leu Ala Ala Phe Arg
        275                 280                 285

Ala Arg Phe Tyr Met Glu Pro Asp Thr Ser Asp Ser Ser Ser Val Val
    290                 295                 300

Ser Gly Pro Gly Val Arg Gly Pro Leu Ser Gly Ser Ser Thr Ser Arg
305                 310                 315                 320

Thr Arg Ala Pro Gly Gly Ala Ala Val Lys Pro Leu Pro Ala Leu Lys
                325                 330                 335

Asp Ser Val Lys Arg Val Met Phe Tyr Cys
            340                 345

<210> SEQ ID NO 33
<211> LENGTH: 551
<212> TYPE: DNA
<213> ORGANISM: Oryza sativa
<220> FEATURE:
<221> NAME/KEY: unsure
<222> LOCATION: (23)
<223> OTHER INFORMATION: n = A, C, G or T
<220> FEATURE:
<221> NAME/KEY: unsure
<222> LOCATION: (504)
<223> OTHER INFORMATION: n = A, C, G or T
<220> FEATURE:
<221> NAME/KEY: unsure
<222> LOCATION: (546)
<223> OTHER INFORMATION: n = A, C, G or T

<400> SEQUENCE: 33
ttgccatggc ctaccatacg acnaaccaga ttacgctcat atggccatgg aggccagtgc     60
aagaattggc caatggaata tgatgaataa gaaaatggtc aatggtggta gagttaacaa    120
ctggacatgc atcaattttt ctcgtcatgt ccaagataat gctgctagga gtttctgtcg    180
cgagcttgct attatgtgcc aaatatctgg gatggacttc tcaattgatc ctgtggttcc    240
tctagtgact gcaagacctg aacatgtgga agagcgctc aaggcacgct atcaagaggc     300
catgaatata ctgaaaccac agggcgggga gcttgacctg ctgattgcaa tattgcctga    360
caataatggt tctctttatg gcgatctcaa aaggatatgt gagactgatc ttggattggt    420

```
ctcgcaatgc tgtcttacga agcatgtttt taagatgagc aaacagtatt taacaaacgt    480
tgcccttaaa atcaatgtta aggngggaag gaaaaaatac aagtactttg ttggatgcct    540
ttgacnaagg g                                                         551
```

```
<210> SEQ ID NO 34
<211> LENGTH: 169
<212> TYPE: PRT
<213> ORGANISM: Oryza sativa
<220> FEATURE:
<221> NAME/KEY: UNSURE
<222> LOCATION: (8)
<223> OTHER INFORMATION: Xaa = ANY AMINO ACID
<220> FEATURE:
<221> NAME/KEY: UNSURE
<222> LOCATION: (168)
<223> OTHER INFORMATION: Xaa = ANY AMINO ACID

<400> SEQUENCE: 34
```

Cys His Gly Leu Pro Tyr Asp Xaa Pro Asp Tyr Ala His Met Ala Met
1               5                   10                  15

Glu Ala Ser Ala Arg Ile Gly Gln Trp Asn Met Met Asn Lys Lys Met
                20                  25                  30

Val Asn Gly Gly Arg Val Asn Asn Trp Thr Cys Ile Asn Phe Ser Arg
            35                  40                  45

His Val Gln Asp Asn Ala Ala Arg Ser Phe Cys Arg Glu Leu Ala Ile
        50                  55                  60

Met Cys Gln Ile Ser Gly Met Asp Phe Ser Ile Asp Pro Val Val Pro
65                  70                  75                  80

Leu Val Thr Ala Arg Pro Glu His Val Glu Arg Ala Leu Lys Ala Arg
                85                  90                  95

Tyr Gln Glu Ala Met Asn Ile Leu Lys Pro Gln Gly Gly Glu Leu Asp
                100                 105                 110

Leu Leu Ile Ala Ile Leu Pro Asp Asn Asn Gly Ser Leu Tyr Gly Asp
            115                 120                 125

Leu Lys Arg Ile Cys Glu Thr Asp Leu Gly Leu Val Ser Gln Cys Cys
        130                 135                 140

Leu Thr Lys His Val Phe Lys Met Ser Lys Gln Tyr Leu Thr Asn Val
145                 150                 155                 160

Ala Leu Lys Ile Asn Val Lys Xaa Gly
                165

```
<210> SEQ ID NO 35
<211> LENGTH: 966
<212> TYPE: DNA
<213> ORGANISM: Glycine max

<400> SEQUENCE: 35
cttcggaagt tgagggatta cctcagtgga agcgtgcttt cgatccctag ggatgttttg     60
cacggcttgg atttggtggt gaaggaaaat ccttcgaagc agtgtgtttc cttgggcgg    120 tgcttcttcc ccatgaaccc tcctttgagg aagaaagatc ttaaccatgg cataattgcg    180
attggagggt ttcagcagag tcttaagtct acttctcagg gattgtcctt gtgcctggac    240
tattcggttt tgtcctttcg gaagaagctg ttggtgttgg attttctgca cgagcatatt    300
agggacttca atttaaggga gtttgggcgg ttcaggagac aagttgagca tgtacttatt    360
gggttgaagg ttaatgttaa acaccggaag acaaagcaga agtacactat tactaggttg    420
acacccaagg ttacgagaca tatcacattc cctattttgg atcccgaggg ccggaatccc    480
```

-continued

```
ccaaaggaag ctactctggt tggttacttt ctagagaagt atggtgtgaa cattgaatac    540
aaggacattc ctgccttgga ttttggaggc aacaagacga ttttgtgcc tatggagttt     600 tgtgagttgg ttgaggggca gagatatccc aaagagaatt tggacaaata tgctgccaag    660
gacttaaaag acatgtcagt ggctcctcca agggtgaggc aaagtacaat acaagcaatg    720
gtaaactcag aggacggacc gtgcggaggt ggtgttatta aaaattttgg aatgagtgtc    780
aacacttcca tgacaaatgt gacaggacgt gtaattcagc ctccacaatt gaagctaggt    840
aatccaaatg ccagactgt tagtatgaca cttgaagtag agaaatgtca gtggaatcta    900
gtgggacgat caatggtgga aggcaagcca gttgagtgtt gggcattct tgattttacc    960 tcgtgc                                                               966
```

<210> SEQ ID NO 36
<211> LENGTH: 322
<212> TYPE: PRT
<213> ORGANISM: Glycine max
<400> SEQUENCE: 36

```
Leu Arg Lys Leu Arg Asp Tyr Leu Ser Gly Ser Val Leu Ser Ile Pro
 1               5                  10                  15

Arg Asp Val Leu His Gly Leu Asp Leu Val Lys Glu Asn Pro Ser
            20                  25                  30

Lys Gln Cys Val Ser Leu Gly Arg Cys Phe Phe Pro Met Asn Pro Pro
        35                  40                  45

Leu Arg Lys Lys Asp Leu Asn His Gly Ile Ile Ala Ile Gly Gly Phe
    50                  55                  60

Gln Gln Ser Leu Lys Ser Thr Ser Gln Gly Leu Ser Leu Cys Leu Asp
65                  70                  75                  80

Tyr Ser Val Leu Ser Phe Arg Lys Leu Leu Val Leu Asp Phe Leu
                85                  90                  95

His Glu His Ile Arg Asp Phe Asn Leu Arg Glu Phe Gly Arg Phe Arg
            100                 105                 110

Arg Gln Val Glu His Val Leu Ile Gly Leu Lys Val Asn Val Lys His
        115                 120                 125

Arg Lys Thr Lys Gln Lys Tyr Thr Ile Thr Arg Leu Thr Pro Lys Val
    130                 135                 140

Thr Arg His Ile Thr Phe Pro Ile Leu Asp Pro Glu Gly Arg Asn Pro
145                 150                 155                 160

Pro Lys Glu Ala Thr Leu Val Gly Tyr Phe Leu Glu Lys Tyr Gly Val
                165                 170                 175

Asn Ile Glu Tyr Lys Asp Ile Pro Ala Leu Asp Phe Gly Gly Asn Lys
            180                 185                 190

Thr Asn Phe Val Pro Met Glu Phe Cys Glu Leu Val Glu Gly Gln Arg
        195                 200                 205

Tyr Pro Lys Glu Asn Leu Asp Lys Tyr Ala Ala Lys Asp Leu Lys Asp
    210                 215                 220

Met Ser Val Ala Pro Pro Arg Val Arg Gln Ser Thr Ile Gln Ala Met
225                 230                 235                 240

Val Asn Ser Glu Asp Gly Pro Cys Gly Gly Val Ile Lys Asn Phe
                245                 250                 255

Gly Met Ser Val Asn Thr Ser Met Thr Asn Val Thr Gly Arg Val Ile
            260                 265                 270

Gln Pro Pro Gln Leu Lys Leu Gly Asn Pro Asn Gly Gln Thr Val Ser
```

```
                275                 280                 285
Met Thr Leu Glu Val Glu Lys Cys Gln Trp Asn Leu Val Gly Arg Ser
        290                 295                 300

Met Val Glu Gly Lys Pro Val Glu Cys Trp Gly Ile Leu Asp Phe Thr
305                 310                 315                 320

Ser Cys

<210> SEQ ID NO 37
<211> LENGTH: 3613
<212> TYPE: DNA
<213> ORGANISM: Glycine max

<400> SEQUENCE: 37
ttcttgcaag catctcattt ctctctttct ctctttctct ctctttggga gaaaacccac      60
tcttcttttc tctctcttgc acacatatac acactcctct tttttattcc cttcttcact     120
ccactgccca gcttcgccct gtccatcgct caccgtttgc agtagcttct ctacttttca     180
ctttctccct gagatcatgg tcagaaagag aagaactgaa ctaccagtg ggggtgaaag      240
ctctgaggct caacgccctg ctgaaggag tgcaccaccc caacaacagg ctgctgctgc      300
tgccccagga ggggctggac cccaaggag cagaggttgg ggtccccaag gaggacgagg      360
aggctatggt gggggccgca gtcgtgggat gccccaacag caatatggtg cccctcctga     420
atatcaaggt aggggaaggg gagggccttc tcagcaagga ggccgtggag ggtatggcgg     480
tggccgaagt ggtggtggta tgggcagtgg ccgtggcgta ggtccttcat atggtggccc     540
atccaggcca ccgcacccg agctgcacca agcaacctca gttcaattct atcaaactgg      600
ggtgagttct cagcctgcat tatctgaggc cagttcatca ctgccgccgc cggaacctgt     660
tgatttggaa cagtcaatgg cgcagatggt gcttcattct gaagctgctc cttctccgcc     720
tcctgcaagt aaatcatcaa tgaggttccc tcttcgacca ggaaagggta gctatggcac     780
caaatgtgtt gtcaaggcta atcatttctt tgccgagttg cccaacaaag atctgcatca     840
atatgatgta acaattactc ctgaagtgac atcaagagga gtgaaccgtg ctgttatgga     900
gcagttggtg aggctgtatc gggaatctca cttgggtaag agacttcctg cttacgatgg     960
gcgcaagagc ctctatactg ctggaccact tccttttatg tcaaaggagt tcagaattgt    1020
tcttgctgat gatgatgaag gagctggagg ccagaggagg acagggaat tcaaggttgt    1080
gataaaattg gctgcacggg cagatcttca ccatttagga ctcttttac agggaaggca    1140
aactgatgct cctcaagagg ctttgcaggt ccttgacatt gttctgcgtg aactccctac    1200
tacaaggtat tgtcctgtag aagatcatt ttattcacct gatttgggta gaagacagcc    1260
tttaggtgag ggattggaaa gctggcgtgg tttctaccag agtattcggc tacacagat     1320
ggggctatcc ctgaacattg atatgtcttc cactgcattt attgagccat tgccggtaat    1380
tgacttcgta aatcaactgc tgaacagaga tgtatctgcc cggccattat ctgatgctga    1440
tcgtgttaag atcaagaaag ctcttcgagg tatcaaagtt gaagtaacac atcgtggaaa    1500
catgagaagg aaatatcgta tctctggtct gacttcacag gcaaccagag aattgacatt    1560
cccagtagat gaaaggggaa ccatgaaatc tgttgtggag tacttctatg agacatatgg    1620
gtttgtcatt caacatactc agtggccttg tctgcaagtt ggcaatacac agagacctaa    1680
ctatttgcca atggaggttt gcaagatagt ggaaggtcaa aggtactcaa aaaggcttaa    1740
tgagaggcaa atcaccgctt tgctgaaagt tacatgccag cgtcctgttg agagggagcg    1800
tgatatcatg cagacagtac accacaatgc ataccatgaa gatccttatg ccaaagaatt    1860
```

```
tgggatcaag atcagtgaga agcttgctca agttgaagct cgcatccttc ctgctccatg   1920
gctcaaatat cacgatacgg gcagagaaaa ggattgtctt cctcaagttg ggcaatggaa   1980
tatgatgaat aagaaaatgg ttaatggggg aacagttaac aactggttct gcataaactt   2040
ttcgaggaat gttcaagata gtgttgcccg cggttttgc tatgaacttg ctcagatgtg    2100
ttatatatct ggaatggcat ttacacctga gccagtagtt cccccagtca gtgctcgccc   2160
tgatcaagtg gaaaaggttc ttaaaactcg gtatcacgat gccaagaata aactgcaagg   2220
aaaagagctt gatttactca ttgttatctt gccggataat aatggatcac tatatggtga   2280
cctcaaacgt atttgtgaga cagatctagg acttgtttca caatgttgct taactaagca   2340
tgtcttcaaa atgagcaagc agtaccttgc aaatgttgct ttgaaaatta atgtcaaagt   2400
tggagggaga aacactgtac tggttgatgc gctctcacga cgcattccct tggtcagtga   2460
cagacctaca attatttttg gagctgatgt gactcatcca catcctggag aggattcaag   2520
tccatcaatt gcagcagttg tggcttcgca agactatcct gaaattacaa gtatgctgg   2580
tttagtttgt gcccaagctc ataggcagga actcatccag gatcttttca acaatggca   2640
agatccagtc agaggaacag tgactggtgg aatgatcaag gaacttctta tatcttttag   2700
gagagctaca ggacaaaagc cacaacgcat catattttat agggatggtg ttagtgaggg   2760
tcaattttat caggttctac tgtttgagct tgatgctatt cgaaaggcat gtgcatccct   2820
ggaacccaac tatcagcctc ctgtgacttt tgtggtggtt caaaagcgtc accacacaag   2880
gctcttttgcc agcaaccatc acgataagag ttcttttgac aggagtggca acatattgcc   2940
tggtactgtt gttgactcca aaatctgcca tcccaccgaa tttgactttt atctctgcag   3000
ccatgctgga atacagggta caagccgtcc tgctcactac catgtgttgt gggatgaaaa   3060
caattttact gctgatgcct tgcaaacact caccaataat ctttgctaca catatgctcg   3120
gtgcacccga tctgtttcaa ttgtgcctcc tgcatactat gctcaccttg ctgcattccg   3180
tgcaaggttt tacatggaac ccgagacttc ggatagtggc tctatgacaa gtggtgctgt   3240
tgcaggccgt gggatgggtg gcggcggtgg tggtggtgta gggcgtagca cccgggcacc   3300
tggtgctaat gctgctgtga gaccattgcc tgcactcaaa gagaacgtta agagagttat   3360
gttttattgt aagaagata tgatatgcat gccaaagatt acttttagca accttgtttt    3420
gtggaggagt gcttttccc ttgctgcttt caaactatct ccagtggtgt ggtctgtgtc   3480
attagtattg agttttttga aactatttaa ggtgtgtggt gtgttgaata aggttgtcca   3540
gtgtggagtg gagtgttta tctttgctat gagggtctga tatttgatgc aaaaaaaaa    3600
aaaaaaaaa aaa                                                      3613
```

<210> SEQ ID NO 38
<211> LENGTH: 1058
<212> TYPE: PRT
<213> ORGANISM: Glycine max

<400> SEQUENCE: 38

Met Val Arg Lys Arg Arg Thr Glu Leu Pro Ser Gly Gly Glu Ser Ser
1               5                   10                  15

Glu Ala Gln Arg Pro Ala Glu Arg Ser Ala Pro Gln Gln Gln Ala
            20                  25                  30

Ala Ala Ala Ala Pro Gly Gly Ala Gly Pro Gln Gly Gly Arg Gly Trp
        35                  40                  45

Gly Pro Gln Gly Gly Arg Gly Gly Tyr Gly Gly Gly Arg Ser Arg Gly

```
                50                  55                  60
        Met Pro Gln Gln Tyr Gly Ala Pro Pro Glu Tyr Gln Gly Arg Gly
         65                  70                  75                  80
        Arg Gly Gly Pro Ser Gln Gln Gly Arg Gly Gly Tyr Gly Gly
                             85                  90                  95
        Arg Ser Gly Gly Gly Met Gly Ser Gly Arg Gly Val Gly Pro Ser Tyr
                            100                 105                 110
        Gly Gly Pro Ser Arg Pro Pro Ala Pro Glu Leu His Gln Ala Thr Ser
                            115                 120                 125
        Val Gln Phe Tyr Gln Thr Gly Val Ser Ser Gln Pro Ala Leu Ser Glu
                            130                 135                 140
        Ala Ser Ser Ser Leu Pro Pro Glu Pro Val Asp Leu Glu Gln Ser
        145                 150                 155                 160
        Met Ala Gln Met Val Leu His Ser Glu Ala Ala Pro Ser Pro Pro Pro
                            165                 170                 175
        Ala Ser Lys Ser Ser Met Arg Phe Pro Leu Arg Pro Gly Lys Gly Ser
                            180                 185                 190
        Tyr Gly Thr Lys Cys Val Val Lys Ala Asn His Phe Ala Glu Leu
                            195                 200                 205
        Pro Asn Lys Asp Leu His Gln Tyr Asp Val Thr Ile Thr Pro Glu Val
        210                 215                 220
        Thr Ser Arg Gly Val Asn Arg Ala Val Met Glu Gln Leu Val Arg Leu
        225                 230                 235                 240
        Tyr Arg Glu Ser His Leu Gly Lys Arg Leu Pro Ala Tyr Asp Gly Arg
                            245                 250                 255
        Lys Ser Leu Tyr Thr Ala Gly Pro Leu Pro Phe Met Ser Lys Glu Phe
                            260                 265                 270
        Arg Ile Val Leu Ala Asp Asp Glu Gly Ala Gly Gly Gln Arg Arg
                            275                 280                 285
        Asp Arg Glu Phe Lys Val Val Ile Lys Leu Ala Ala Arg Ala Asp Leu
                            290                 295                 300
        His His Leu Gly Leu Phe Leu Gln Gly Arg Gln Thr Asp Ala Pro Gln
        305                 310                 315                 320
        Glu Ala Leu Gln Val Leu Asp Ile Val Leu Arg Glu Leu Pro Thr Thr
                            325                 330                 335
        Arg Tyr Cys Pro Val Gly Arg Ser Phe Tyr Ser Pro Asp Leu Gly Arg
                            340                 345                 350
        Arg Gln Pro Leu Gly Glu Gly Leu Glu Ser Trp Arg Gly Phe Tyr Gln
                            355                 360                 365
        Ser Ile Arg Pro Thr Gln Met Gly Leu Ser Leu Asn Ile Asp Met Ser
                            370                 375                 380
        Ser Thr Ala Phe Ile Glu Pro Leu Pro Val Ile Asp Phe Val Asn Gln
        385                 390                 395                 400
        Leu Leu Asn Arg Asp Val Ser Ala Arg Pro Leu Ser Asp Ala Asp Arg
                            405                 410                 415
        Val Lys Ile Lys Lys Ala Leu Arg Gly Ile Lys Val Glu Val Thr His
                            420                 425                 430
        Arg Gly Asn Met Arg Arg Lys Tyr Arg Ile Ser Gly Leu Thr Ser Gln
                            435                 440                 445
        Ala Thr Arg Glu Leu Thr Phe Pro Val Asp Glu Arg Gly Thr Met Lys
                            450                 455                 460
        Ser Val Val Glu Tyr Phe Tyr Glu Thr Tyr Gly Phe Val Ile Gln His
        465                 470                 475                 480
```

```
Thr Gln Trp Pro Cys Leu Gln Val Gly Asn Thr Gln Arg Pro Asn Tyr
            485                 490                 495
Leu Pro Met Glu Val Cys Lys Ile Val Glu Gly Gln Arg Tyr Ser Lys
            500                 505                 510
Arg Leu Asn Glu Arg Gln Ile Thr Ala Leu Leu Lys Val Thr Cys Gln
            515                 520                 525
Arg Pro Val Glu Arg Glu Arg Asp Ile Met Gln Thr Val His His Asn
            530                 535                 540
Ala Tyr His Glu Asp Pro Tyr Ala Lys Glu Phe Gly Ile Lys Ile Ser
545                 550                 555                 560
Glu Lys Leu Ala Gln Val Glu Ala Arg Ile Leu Pro Ala Pro Trp Leu
                565                 570                 575
Lys Tyr His Asp Thr Gly Arg Glu Lys Asp Cys Leu Pro Gln Val Gly
                580                 585                 590
Gln Trp Asn Met Met Asn Lys Lys Met Val Asn Gly Gly Thr Val Asn
                595                 600                 605
Asn Trp Phe Cys Ile Asn Phe Ser Arg Asn Val Gln Asp Ser Val Ala
            610                 615                 620
Arg Gly Phe Cys Tyr Glu Leu Ala Gln Met Cys Tyr Ile Ser Gly Met
625                 630                 635                 640
Ala Phe Thr Pro Glu Pro Val Val Pro Pro Val Ser Ala Arg Pro Asp
                645                 650                 655
Gln Val Glu Lys Val Leu Lys Thr Arg Tyr His Asp Ala Lys Asn Lys
                660                 665                 670
Leu Gln Gly Lys Glu Leu Asp Leu Leu Ile Val Ile Leu Pro Asp Asn
                675                 680                 685
Asn Gly Ser Leu Tyr Gly Asp Leu Lys Arg Ile Cys Glu Thr Asp Leu
690                 695                 700
Gly Leu Val Ser Gln Cys Cys Leu Thr Lys His Val Phe Lys Met Ser
705                 710                 715                 720
Lys Gln Tyr Leu Ala Asn Val Ala Leu Lys Ile Asn Val Lys Val Gly
                725                 730                 735
Gly Arg Asn Thr Val Leu Val Asp Ala Leu Ser Arg Arg Ile Pro Leu
                740                 745                 750
Val Ser Asp Arg Pro Thr Ile Ile Phe Gly Ala Asp Val Thr His Pro
                755                 760                 765
His Pro Gly Glu Asp Ser Ser Pro Ser Ile Ala Ala Val Val Ala Ser
            770                 775                 780
Gln Asp Tyr Pro Glu Ile Thr Lys Tyr Ala Gly Leu Val Cys Ala Gln
785                 790                 795                 800
Ala His Arg Gln Glu Leu Ile Gln Asp Leu Phe Lys Gln Trp Gln Asp
                805                 810                 815
Pro Val Arg Gly Thr Val Thr Gly Met Ile Lys Glu Leu Leu Ile
                820                 825                 830
Ser Phe Arg Arg Ala Thr Gly Gln Lys Pro Gln Arg Ile Ile Phe Tyr
            835                 840                 845
Arg Asp Gly Val Ser Glu Gly Gln Phe Tyr Gln Val Leu Leu Phe Glu
850                 855                 860
Leu Asp Ala Ile Arg Lys Ala Cys Ala Ser Leu Glu Pro Asn Tyr Gln
865                 870                 875                 880
Pro Pro Val Thr Phe Val Val Gln Lys Arg His His Thr Arg Leu
                885                 890                 895
```

-continued

```
Phe Ala Ser Asn His His Asp Lys Ser Ser Phe Asp Arg Ser Gly Asn
              900                 905                 910
Ile Leu Pro Gly Thr Val Val Asp Ser Lys Ile Cys His Pro Thr Glu
          915                 920                 925
Phe Asp Phe Tyr Leu Cys Ser His Ala Gly Ile Gln Gly Thr Ser Arg
      930                 935                 940
Pro Ala His Tyr His Val Leu Trp Asp Glu Asn Asn Phe Thr Ala Asp
945                 950                 955                 960
Ala Leu Gln Thr Leu Thr Asn Asn Leu Cys Tyr Thr Tyr Ala Arg Cys
              965                 970                 975
Thr Arg Ser Val Ser Ile Val Pro Pro Ala Tyr Tyr Ala His Leu Ala
          980                 985                 990
Ala Phe Arg Ala Arg Phe Tyr Met Glu Pro Glu Thr Ser Asp Ser Gly
      995                 1000                1005
Ser Met Thr Ser Gly Ala Val Ala Gly Arg Gly Met Gly Gly Gly Gly
    1010                1015                1020
Gly Gly Gly Val Gly Arg Ser Thr Arg Ala Pro Gly Ala Asn Ala Ala
1025                1030                1035                1040
Val Arg Pro Leu Pro Ala Leu Lys Glu Asn Val Lys Arg Val Met Phe
              1045                1050                1055
Tyr Cys

<210> SEQ ID NO 39
<211> LENGTH: 3239
<212> TYPE: DNA
<213> ORGANISM: Glycine max

<400> SEQUENCE: 39
ttctaaactc actctctcac tttctcactc cctcactccc tccgttgacg ttttttgtttt     60
cttttctct gtgttctgaa gaagttttag ggtttcgttt tgtttctctc ttcggccact      120
tcaggctatg gattcatttg agccagatgg aaatgggaag gagtcactgc caccaccacc     180
tcctgttgtt ccctctgata ttgtacctct caaagcagag gaggtgctct gtaccccctac    240
cgagcataat aagaaaaagg cttcccgact tccaatagcc agatctggtc tgggatcaaa     300
aggaaataaa atacaattac taaccaatca cttcaaagtt aatgttgcta aaaatgatgg     360
gcatttcttc cattatagtg tggcttttac ttatgaagat ggacgccctg tagaaggtaa     420
gggtgtaggg agaaagataa tagatagggt gcaggagaca tatcattctg acttaaatgg     480
taaggacttt gcatatgatg gggagaaaag tctgtttact gttggctctc ttcctcaaaa     540
caagcttgag tttgaagttg ttcttgagga tgtcacctct aacaggaata atggcaattg     600
cagccctgat ggtctagggg acaatgagag tgacagaaag aggatgcgac gtccttatcg     660
ttcgaagtca ttcaaagtag agataagctt tgctgcaaaa attccaatgc aggccattgc     720
cagtgcctta cgcgggcaag agactgagaa ttttcaagaa gccatcagag ttcttgatat     780
cattttgagg cagcatgctg ctaagcaagg ctgcttactt gtacgccaat ccttttttcca    840
caataatcca ataattttg ctgatgtagg aggtggtgtc ctaggctgta gaggattcca     900
ctcaagcttt agaactacac agagtggcct gtctcttaac atagatgtgt caactacaat    960
gataatttct cctgggcctg tggtggattt cttaatttcc aatcaaaatg tgagagatcc    1020
ttttcaactt gactgggcta aggccaaaag gaccctaaaa atctgagga ttaaaactag    1080
cccatccaat caagaattca aaatttctgg gctcagtgaa ctcccatgca gagagcagac    1140
ttttactttg aaaggtaaag gtgggggga tggtgaagat ggtaatgagg aaatcactgt    1200
```

```
atatgattat tttgttaagg ttcgtaagat agatctccga tactctgctg accttccatg    1260
tatcaatgtt ggcaagccta aacgaccaac attttttcccc attgaggttt gtgaattggt    1320
atcattgcaa cgatatacaa aagctctgtc cacgcttcaa agggcttcat tagtggagaa    1380
gtcgaggcag aagccacaag agaggatgaa aattttgtct gatgcactga gaacaagcaa    1440
ctatggtgct gaacctatgc tccggaattg tggaatttct ataagcactg gcttcactga    1500
agtggagggc cgggtgttgc ctgcaccaag gttgaagttt ggcaatggtg aggatctcaa    1560
tcctaggaat gggagatgga atgtcagcag agtgaaattt gtggaaccat caaagataga    1620
aagatgggct gttgctaact tttctgcacg ctgtgatgta cgaggacttg tacgggacct    1680
cattagaatt ggagatatga aaggaattac tatagaacaa ccatttgacg tgtttgatga    1740
gaatccacag tttaggcgtg cccccccctat ggttagagtg gagaaaatgt tcgagcatat    1800
ccaatctaaa cttcctgggg ctcctcagtt ccttctctgt ttgcttcctg atcggaaaaa    1860
ttgtgatatt tatggtccat ggaaaaagaa gaatcttgct gattttggaa tcataaatca    1920
gtgtatgtgt cctttaaggg tcaatgacca gtacctgact aatgttatgt tgaagatcaa    1980
tgccaagctt ggtgggttga attcattgtt aggcgttgaa cattctcctt ctcttcctgt    2040
tgtttccaaa gctcccaccc tcattctggg aatggacgtg tcacatggct cacctgggca    2100
gactgacatt ccttcaattg ctgcggtggt cagctctaga cactggcctc tgatatcaaa    2160
gtatagggca tgtgttcgta cgcaatctgc aaagatggaa atgattgata atttgttcaa    2220
gctagtatct gaaaggaag atgaaggcat cataagggaa cttttgcttg atttctatac    2280
aacttctggg aggagaaaac cggaaaatat aatcatattc agggatgggg ttagtgagtc    2340
acaattcaat caagttttga atattgaact cgatcgaatc attgaggctt gcaaatttct    2400
cgatgaaaat tgggagccaa aatttgtggt aattgttgct cagaagaacc accacactag    2460 attttttccag cctggctctc ccgacaatgt cccacctgga actgttatcg acaataaaat    2520
ttgtcatccc agaaattatg atttctacct atgtgcacat gctggaatga taggaactag    2580
taggcctacc cattatcatg tgctgcttga tcaggttggt ttctctccgg atcagctgca    2640
ggagcttgtc cattcattat catatgtgta tcagaggagc actactgcca tttctgttgt    2700
tgctccaata tgctatgcgc acttggctgc tactcagttg gggcagttca tgaaatttga    2760
ggacaaatct gaaacatctt caagccatgg tggattgagc ggtgcaagtg ctgttcccgt    2820
ccctcagttg cctcccttgc aagagaatgt ccgcaacaca atgttctttt gttgaagcct    2880
taatgctctg ccctgtctcc tcaagtggtg aaaatgctgt acataaaact atgtttctaa    2940
tcttgcaagt tatgcggacg aagtttatat tgtggtagac ttggtcttct tagccatatt    3000
tagtctttct agcacaagcc ttttcaaatg ttcggggacc ttaccttact tttttgtagca    3060 agactctctt tagcgcaacg tcttttttgta gcaaggcttg atcttcagca cgtctttttgt    3120 taggcccccc cttttttaag gtttaattgc acttttttacc tcgaatgctg taatttatag    3180
tgaattttac ttatctccaa aaaaaaaaaa aaaaaaaaa aaaaaaaaa aaaaaaaa      3239
```

<210> SEQ ID NO 40
<211> LENGTH: 915
<212> TYPE: PRT
<213> ORGANISM: Glycine max

<400> SEQUENCE: 40

Met Asp Ser Phe Glu Pro Asp Gly Asn Gly Lys Glu Ser Leu Pro Pro
1               5                   10                  15

```
Pro Pro Pro Val Val Pro Ser Asp Ile Val Pro Leu Lys Ala Glu Glu
            20                  25                  30

Val Leu Cys Thr Pro Thr Glu His Asn Lys Lys Ala Ser Arg Leu
        35                  40                  45

Pro Ile Ala Arg Ser Gly Leu Gly Ser Lys Gly Asn Lys Ile Gln Leu
    50                  55                  60

Leu Thr Asn His Phe Lys Val Asn Val Ala Lys Asn Asp Gly His Phe
65                  70                  75                  80

Phe His Tyr Ser Val Ala Phe Thr Tyr Glu Asp Gly Arg Pro Val Glu
                85                  90                  95

Gly Lys Gly Val Gly Arg Lys Ile Ile Asp Arg Val Gln Glu Thr Tyr
            100                 105                 110

His Ser Asp Leu Asn Gly Lys Asp Phe Ala Tyr Asp Gly Glu Lys Ser
        115                 120                 125

Leu Phe Thr Val Gly Ser Leu Pro Gln Asn Lys Leu Glu Phe Glu Val
    130                 135                 140

Val Leu Glu Asp Val Thr Ser Asn Arg Asn Asn Gly Asn Cys Ser Pro
145                 150                 155                 160

Asp Gly Leu Gly Asp Asn Glu Ser Asp Arg Lys Arg Met Arg Arg Pro
                165                 170                 175

Tyr Arg Ser Lys Ser Phe Lys Val Glu Ile Ser Phe Ala Ala Lys Ile
            180                 185                 190

Pro Met Gln Ala Ile Ala Ser Ala Leu Arg Gly Gln Glu Thr Glu Asn
        195                 200                 205

Phe Gln Glu Ala Ile Arg Val Leu Asp Ile Ile Leu Arg Gln His Ala
    210                 215                 220

Ala Lys Gln Gly Cys Leu Leu Val Arg Gln Ser Phe Phe His Asn Asn
225                 230                 235                 240

Pro Asn Asn Phe Ala Asp Val Gly Gly Gly Val Leu Gly Cys Arg Gly
                245                 250                 255

Phe His Ser Ser Phe Arg Thr Thr Gln Ser Gly Leu Ser Leu Asn Ile
            260                 265                 270

Asp Val Ser Thr Thr Met Ile Ile Ser Pro Gly Pro Val Val Asp Phe
        275                 280                 285

Leu Ile Ser Asn Gln Asn Val Arg Asp Pro Phe Gln Leu Asp Trp Ala
    290                 295                 300

Lys Ala Lys Arg Thr Leu Lys Asn Leu Arg Ile Lys Thr Ser Pro Ser
305                 310                 315                 320

Asn Gln Glu Phe Lys Ile Ser Gly Leu Ser Glu Leu Pro Cys Arg Glu
                325                 330                 335

Gln Thr Phe Thr Leu Lys Gly Lys Gly Gly Gly Asp Gly Glu Asp Gly
            340                 345                 350

Asn Glu Glu Ile Thr Val Tyr Asp Tyr Phe Val Lys Val Arg Lys Ile
        355                 360                 365

Asp Leu Arg Tyr Ser Ala Asp Leu Pro Cys Ile Asn Val Gly Lys Pro
    370                 375                 380

Lys Arg Pro Thr Phe Phe Pro Ile Glu Val Cys Glu Leu Val Ser Leu
385                 390                 395                 400

Gln Arg Tyr Thr Lys Ala Leu Ser Thr Leu Gln Arg Ala Ser Leu Val
                405                 410                 415

Glu Lys Ser Arg Gln Lys Pro Gln Glu Arg Met Lys Ile Leu Ser Asp
            420                 425                 430
```

-continued

Ala Leu Arg Thr Ser Asn Tyr Gly Ala Glu Pro Met Leu Arg Asn Cys
            435                 440                 445

Gly Ile Ser Ile Ser Thr Gly Phe Thr Glu Val Glu Gly Arg Val Leu
        450                 455                 460

Pro Ala Pro Arg Leu Lys Phe Gly Asn Gly Glu Asp Leu Asn Pro Arg
465                 470                 475                 480

Asn Gly Arg Trp Asn Val Ser Arg Val Lys Phe Val Glu Pro Ser Lys
                485                 490                 495

Ile Glu Arg Trp Ala Val Ala Asn Phe Ser Ala Arg Cys Asp Val Arg
                500                 505                 510

Gly Leu Val Arg Asp Leu Ile Arg Ile Gly Asp Met Lys Gly Ile Thr
            515                 520                 525

Ile Glu Gln Pro Phe Asp Val Phe Asp Glu Asn Pro Gln Phe Arg Arg
        530                 535                 540

Ala Pro Pro Met Val Arg Val Glu Lys Met Phe Glu His Ile Gln Ser
545                 550                 555                 560

Lys Leu Pro Gly Ala Pro Gln Phe Leu Leu Cys Leu Leu Pro Asp Arg
                565                 570                 575

Lys Asn Cys Asp Ile Tyr Gly Pro Trp Lys Lys Asn Leu Ala Asp
                580                 585                 590

Phe Gly Ile Ile Asn Gln Cys Met Cys Pro Leu Arg Val Asn Asp Gln
            595                 600                 605

Tyr Leu Thr Asn Val Met Leu Lys Ile Asn Ala Lys Leu Gly Gly Leu
        610                 615                 620

Asn Ser Leu Leu Gly Val Glu His Ser Pro Ser Leu Pro Val Val Ser
625                 630                 635                 640

Lys Ala Pro Thr Leu Ile Leu Gly Met Asp Val Ser His Gly Ser Pro
                645                 650                 655

Gly Gln Thr Asp Ile Pro Ser Ile Ala Ala Val Val Ser Ser Arg His
            660                 665                 670

Trp Pro Leu Ile Ser Lys Tyr Arg Ala Cys Val Arg Thr Gln Ser Ala
        675                 680                 685

Lys Met Glu Met Ile Asp Asn Leu Phe Lys Leu Val Ser Glu Lys Glu
690                 695                 700

Asp Glu Gly Ile Ile Arg Glu Leu Leu Leu Asp Phe Tyr Thr Thr Ser
705                 710                 715                 720

Gly Arg Arg Lys Pro Glu Asn Ile Ile Ile Phe Arg Asp Gly Val Ser
                725                 730                 735

Glu Ser Gln Phe Asn Gln Val Leu Asn Ile Glu Leu Asp Arg Ile Ile
            740                 745                 750

Glu Ala Cys Lys Phe Leu Asp Glu Asn Trp Glu Pro Lys Phe Val Val
        755                 760                 765

Ile Val Ala Gln Lys Asn His His Thr Arg Phe Phe Gln Pro Gly Ser
770                 775                 780

Pro Asp Asn Val Pro Pro Gly Thr Val Ile Asp Asn Lys Ile Cys His
785                 790                 795                 800

Pro Arg Asn Tyr Asp Phe Tyr Leu Cys Ala His Ala Gly Met Ile Gly
                805                 810                 815

Thr Ser Arg Pro Thr His Tyr His Val Leu Leu Asp Glu Val Gly Phe
            820                 825                 830

Ser Pro Asp Gln Leu Gln Glu Leu Val His Ser Leu Ser Tyr Val Tyr
        835                 840                 845

Gln Arg Ser Thr Thr Ala Ile Ser Val Val Ala Pro Ile Cys Tyr Ala

```
                850               855               860
His Leu Ala Ala Thr Gln Leu Gly Gln Phe Met Lys Phe Glu Asp Lys
865                 870                 875                 880

Ser Glu Thr Ser Ser His Gly Gly Leu Ser Gly Ala Ser Ala Val
                885                 890                 895

Pro Val Pro Gln Leu Pro Pro Leu Gln Glu Asn Val Arg Asn Thr Met
                900                 905                 910

Phe Phe Cys
        915

<210> SEQ ID NO 41
<211> LENGTH: 3151
<212> TYPE: DNA
<213> ORGANISM: Triticum aestivum

<400> SEQUENCE: 41
gttgttcgag agaggggag ggggagagac gagaagggga acggaaaaga aagccaagcc    60
ctctctcgcg gaggccaacg gcgaggcttc tcccttgcg ccctcgcaga tcagttcagc   120
ggttcggctc ctcgggacca ttgttggttc gctgaaatgg agtcacacgg agaggacctg   180
ccaccaccac caccactccc gccaaatgca gagccgataa agctgagtc ggctgatgac   240
ttgccaccac caccaccct gctgcctatc aaacctgaag agcaaagaa gatctcaaag   300
cctaagaggg ccctgatcgc tcgtcctggt tttggcaaga ggggaaatcc tatacagctt   360
gtgacaaatc atttcaaagt ctcgttgaag acgacagacg agttcttcca tcattactat   420
gtaaatctga agtatgaaga tgacaggcct gttgatggaa aggtgttgg tagaaaagtc   480
attgataagc ttgctcagac ttatccatcg gaactagccc ataaagactt tgcctatgat   540
ggtgaaaaga gtctttttac cattggtgcc ctcccacaaa ttaacaatga gtttgttgtg   600
gttcttgaag atgtttccag tggaaagact cctgcaaatg cagccctgg aaacgacagt   660
ccagacaaga agagagtgaa aaggccatat caaactaaaa ccttcaaggt ggagttgagc   720
tttgctgcta gaatccccat gagtgctatt gcaatggcac tcaaaggcca ggaatcagag   780
cacacgcaag aagccattcg ggttattgat atcatattaa gacagcactc tgccaaacag   840
ggctgcctgt tagtccgcca gtcatttttt cacaacaatc cttcaaactt tgtggacttg   900
ggtggggtg tgatgggctg ccgaggtttc cactcaagct ttcgagccac acagagcggg   960
ctttctctta atattgatgt ttctacaaca atgattgtga aacctggccc tgttgtcgat  1020
tttctgctgg ccaaccagaa ggttgaccac cctaataaa ttgattgggc taaggccaag  1080
cgtgcactta agaatttaag gataaaaaca agcccagcaa atacagaata caagattgtt  1140
ggtttgagtg agaggaattg ttatgaacaa atgttttccc tcaagcaaag gaatggtggg  1200
aatggtgacc ctgaagcaat agaaatatct gtttatgatt actttgtgaa gaaccgtggc  1260
attgagctga ggtactctgg tgatttccct tgtataaatg ttgggaaacc taggcggcca  1320
acatattttc ccattgagct ctgccagctg gtcccttac aaaggtatac caaatctttg  1380
agtaccctac aaagatcatc tcttgttgag aagtccaggc agaagcctca agagaggatg  1440
tcagttttgt ctgatgtact gaaacgcagc agctatgata cagaacccat gttgaaggca  1500
tgtggaattt cgatagctca gggctttaca caggtggctg gtagggtact gcaggccccc  1560
aagctcaaag ctggaaatgg tgaagatatt ttcacaagga atggacgttg gaatttcaac  1620
aacaagaggc ttgctagagc ttgtgtggtg gacagatggg cagttgtaaa cttttcggct  1680
aggtgtaaca ccatgaacct tgtcaatgac ctcatcaagt gtgggggcat gaagggcatt  1740
```

```
acagtagaaa aacctcatat tgtaattgaa gagaatggtt caatgagacg tgcacctgct    1800
ccaaaaaggg ttgaggatat gtttgagcaa gtgaagtcta agcttcctgg ggctccgaag    1860
tttctcttgt gtattcttgc tgagaggaag aactcagatg tttatggtcc atggaagcga    1920
aaatgccttg ctgactttgg gattgtcact caatgtgtgg ccccaacaag ggtcaatgac    1980
caatatctga caaatgttct gctgaagatc aatgcaaaac ttggtggaat gaactcacta    2040
ctacaaattg aaatgtcccc aagtatacct cttgtatcaa aggtcccaac tctcatcttg    2100
ggaatggatg tgtcccatgg atccctgga cagtctgata taccgtccat gcagcagtt     2160 gttggttctc gggaatggcc tcttgtctcg aaatataggg cttcagtgcg ctcgcagtca    2220
ccaaagctcg aaatgataga ttcattgttc aagccacaag aactgatga tgatggcctt     2280 gttcgggagt gtctcattga cttctacacc agttctggaa aaaggaaacc agatcagatc    2340
atcatcttca gggatggtgt tagtgagagc cagtttaatc aggtgctgaa cattgaattg    2400
gatcaaataa ttgaggcctg caagttcttg gatgaaaatt ggaaccccaa gttcacgctg    2460
attgttgccc agaaaaatca ccacaccaaa ttcttcatac ctggatctcc tgacaatgtc    2520
cctccaggca ctgttgtaga taatgcagtc tgccatccaa ggaattatga cttctacatg    2580
tgcgctcatg ctggaatgat tgggactaca aggccaacac actaccatat cctgcatgat    2640
gagatacact ttgctgcgga tgacctgcag gatcttgtgc actcgctctc atatgtgtac    2700
caaaggagca cgacagccat atcagttgtt tctccaatct gctatgcaca tcttgcggct    2760
gctcaggtgg cgcagttcat aaagtttgat gagatgtctg agacgtcgtc gagccagggc    2820
ggtggccaca cctctgccgg cagcgctcca gtgcaggagc tgcctcgcct ccatgagaaa    2880
gtccgcagca gcatgttctt ctgctgagcc agccagccag ccgcacttgc gcgttccaac    2940
ttttggtgat gcgcttggtt atctagtact agtagtatgt agtagtggcc tgtgatggcc    3000
tgttggactc ctgggatgtt gtgttcctaa gctggttgct gcacttggtg cctcagaacc    3060
tttgaatcct gtcagggtgc tgcagttgaa cctttactat cgaaccatct aatttgttgc    3120
tttcaaaaaa aaaaaaaaaa aaaaaaaaaa a                                   3151
```

<210> SEQ ID NO 42
<211> LENGTH: 916
<212> TYPE: PRT
<213> ORGANISM: Triticum aestivum

<400> SEQUENCE: 42

```
Met Glu Ser His Gly Glu Asp Leu Pro Pro Pro Pro Leu Pro Pro
  1               5                  10                  15

Asn Ala Glu Pro Ile Lys Ala Glu Ser Ala Asp Asp Leu Pro Pro
                 20                  25                  30

Pro Pro Leu Leu Pro Ile Lys Pro Glu Glu Ala Lys Lys Ile Ser Lys
             35                  40                  45

Pro Lys Arg Ala Leu Ile Ala Arg Pro Gly Phe Gly Lys Arg Gly Asn
         50                  55                  60

Pro Ile Gln Leu Val Thr Asn His Phe Lys Val Ser Leu Lys Thr Thr
 65                  70                  75                  80

Asp Glu Phe Phe His His Tyr Tyr Val Asn Leu Lys Tyr Glu Asp Asp
                 85                  90                  95

Arg Pro Val Asp Gly Lys Gly Val Gly Arg Lys Val Ile Asp Lys Leu
                100                 105                 110

Ala Gln Thr Tyr Pro Ser Glu Leu Ala His Lys Asp Phe Ala Tyr Asp
```

-continued

```
            115                 120                 125
Gly Glu Lys Ser Leu Phe Thr Ile Gly Ala Leu Pro Gln Ile Asn Asn
        130                 135                 140
Glu Phe Val Val Val Leu Glu Asp Val Ser Ser Gly Lys Thr Pro Ala
145                 150                 155                 160
Asn Gly Ser Pro Gly Asn Asp Ser Pro Asp Lys Lys Arg Val Lys Arg
                165                 170                 175
Pro Tyr Gln Thr Lys Thr Phe Lys Val Glu Leu Ser Phe Ala Ala Arg
            180                 185                 190
Ile Pro Met Ser Ala Ile Ala Met Ala Leu Lys Gly Gln Glu Ser Glu
        195                 200                 205
His Thr Gln Glu Ala Ile Arg Val Ile Asp Ile Ile Leu Arg Gln His
    210                 215                 220
Ser Ala Lys Gln Gly Cys Leu Leu Val Arg Gln Ser Phe Phe His Asn
225                 230                 235                 240
Asn Pro Ser Asn Phe Val Asp Leu Gly Gly Gly Val Met Gly Cys Arg
                245                 250                 255
Gly Phe His Ser Ser Phe Arg Ala Thr Gln Ser Gly Leu Ser Leu Asn
            260                 265                 270
Ile Asp Val Ser Thr Thr Met Ile Val Lys Pro Gly Pro Val Val Asp
        275                 280                 285
Phe Leu Leu Ala Asn Gln Lys Val Asp His Pro Asn Lys Ile Asp Trp
    290                 295                 300
Ala Lys Ala Lys Arg Ala Leu Lys Asn Leu Arg Ile Lys Thr Ser Pro
305                 310                 315                 320
Ala Asn Thr Glu Tyr Lys Ile Val Gly Leu Ser Glu Arg Asn Cys Tyr
                325                 330                 335
Glu Gln Met Phe Ser Leu Lys Gln Arg Asn Gly Gly Asn Gly Asp Pro
            340                 345                 350
Glu Ala Ile Glu Ile Ser Val Tyr Asp Tyr Phe Val Lys Asn Arg Gly
        355                 360                 365
Ile Glu Leu Arg Tyr Ser Gly Asp Phe Pro Cys Ile Asn Val Gly Lys
    370                 375                 380
Pro Arg Arg Pro Thr Tyr Phe Pro Ile Glu Leu Cys Gln Leu Val Pro
385                 390                 395                 400
Leu Gln Arg Tyr Thr Lys Ser Leu Ser Thr Leu Gln Arg Ser Ser Leu
                405                 410                 415
Val Glu Lys Ser Arg Gln Lys Pro Gln Glu Arg Met Ser Val Leu Ser
            420                 425                 430
Asp Val Leu Lys Arg Ser Ser Tyr Asp Thr Glu Pro Met Leu Lys Ala
        435                 440                 445
Cys Gly Ile Ser Ile Ala Gln Gly Phe Thr Gln Val Ala Gly Arg Val
    450                 455                 460
Leu Gln Ala Pro Lys Leu Lys Ala Gly Asn Gly Glu Asp Ile Phe Thr
465                 470                 475                 480
Arg Asn Gly Arg Trp Asn Phe Asn Lys Arg Leu Ala Arg Ala Cys
                485                 490                 495
Val Val Asp Arg Trp Ala Val Asn Phe Ser Ala Arg Cys Asn Thr
            500                 505                 510
Met Asn Leu Val Asn Asp Leu Ile Lys Cys Gly Gly Met Lys Gly Ile
        515                 520                 525
Thr Val Glu Lys Pro His Ile Val Ile Glu Glu Asn Gly Ser Met Arg
    530                 535                 540
```

```
Arg Ala Pro Ala Pro Lys Arg Val Glu Asp Met Phe Glu Gln Val Lys
545                 550                 555                 560

Ser Lys Leu Pro Gly Ala Pro Lys Phe Leu Leu Cys Ile Leu Ala Glu
                565                 570                 575

Arg Lys Asn Ser Asp Val Tyr Gly Pro Trp Lys Arg Lys Cys Leu Ala
            580                 585                 590

Asp Phe Gly Ile Val Thr Gln Cys Val Ala Pro Thr Arg Val Asn Asp
        595                 600                 605

Gln Tyr Leu Thr Asn Val Leu Leu Lys Ile Asn Ala Lys Leu Gly Gly
    610                 615                 620

Met Asn Ser Leu Leu Gln Ile Glu Met Ser Pro Ser Ile Pro Leu Val
625                 630                 635                 640

Ser Lys Val Pro Thr Leu Ile Leu Gly Met Asp Val Ser His Gly Ser
                645                 650                 655

Pro Gly Gln Ser Asp Ile Pro Ser Ile Ala Ala Val Val Gly Ser Arg
            660                 665                 670

Glu Trp Pro Leu Val Ser Lys Tyr Arg Ala Ser Val Arg Ser Gln Ser
        675                 680                 685

Pro Lys Leu Glu Met Ile Asp Ser Leu Phe Lys Pro Gln Gly Thr Asp
    690                 695                 700

Asp Asp Gly Leu Val Arg Glu Cys Leu Ile Asp Phe Tyr Thr Ser Ser
705                 710                 715                 720

Gly Lys Arg Lys Pro Asp Gln Ile Ile Ile Phe Arg Asp Gly Val Ser
                725                 730                 735

Glu Ser Gln Phe Asn Gln Val Leu Asn Ile Glu Leu Asp Gln Ile Ile
            740                 745                 750

Glu Ala Cys Lys Phe Leu Asp Glu Asn Trp Asn Pro Lys Phe Thr Leu
        755                 760                 765

Ile Val Ala Gln Lys Asn His His Thr Lys Phe Phe Ile Pro Gly Ser
    770                 775                 780

Pro Asp Asn Val Pro Pro Gly Thr Val Val Asp Asn Ala Val Cys His
785                 790                 795                 800

Pro Arg Asn Tyr Asp Phe Tyr Met Cys Ala His Ala Gly Met Ile Gly
                805                 810                 815

Thr Thr Arg Pro Thr His Tyr His Ile Leu His Asp Glu Ile His Phe
            820                 825                 830

Ala Ala Asp Asp Leu Gln Asp Leu Val His Ser Leu Ser Tyr Val Tyr
        835                 840                 845

Gln Arg Ser Thr Thr Ala Ile Ser Val Val Ser Pro Ile Cys Tyr Ala
    850                 855                 860

His Leu Ala Ala Ala Gln Val Ala Gln Phe Ile Lys Phe Asp Glu Met
865                 870                 875                 880

Ser Glu Thr Ser Ser Ser Gln Gly Gly Gly His Thr Ser Ala Gly Ser
                885                 890                 895

Ala Pro Val Gln Glu Leu Pro Arg Leu His Glu Lys Val Arg Ser Ser
            900                 905                 910

Met Phe Phe Cys
        915

<210> SEQ ID NO 43
<211> LENGTH: 791
<212> TYPE: DNA
<213> ORGANISM: Triticum aestivum
```

<400> SEQUENCE: 43

```
ctcgtgccga attcggcacg agaacttcct caaatacgca acgcatgccg cctgaaatat    60
cctgcaaccg acaccaaacg agggctcccc aggatcacaa ttgttgtctg tggtaaacgc   120
caccacactc gattctaccc taaaaacagc ggtgacgctg ataaatcatc gaatttgatg   180
gctggaactg ttgtcgatcg tggcgttaca gagactcgaa actgggactt ttacctacaa   240
gcccatgcat gtcttcaggg aacagcccgt gcctgtcatt actatgtgat aatagacgaa   300
attttccggt ccaataaggt taagggtggt cacaaaaatc acgctgatgc ccttgaggaa   360
ttgacaaaca atatgagtca tctgtttgga cgagcaacaa aagccgtcag tctttgtcct   420
cctgcttact atgctgattt actctgcaca agggtacgct gctacttatc tgaagttttc   480
gacccaagtg aggcccagag tgtgatgagt ggcggcacca accaaacgat cgaggacatt   540
gttattccgc cgagtatgag ggattccatg tactacatct aagctcattg catgagaatg   600
agaatcatta aaccataacc ttcggtgtta gttacagaat tagctgtgtc aagtcattat   660
agacgaaata ccatttctgt attgtagact ttgcgttccg aaatatttta tgcacacgca   720
aatgtatagc caaaaaaaaa aaaaaaaaaa aaaaaaaaaa aaaaaaaaaa aaaaaaaaaa   780
aaaaaaaaaa a                                                        791
```

<210> SEQ ID NO 44
<211> LENGTH: 193
<212> TYPE: PRT
<213> ORGANISM: Triticum aestivum

<400> SEQUENCE: 44

```
Leu Val Pro Asn Ser Ala Arg Glu Leu Pro Gln Ile Arg Asn Ala Cys
  1               5                  10                  15
Arg Leu Lys Tyr Pro Ala Thr Asp Thr Lys Arg Gly Leu Pro Arg Ile
             20                  25                  30
Thr Ile Val Val Cys Gly Lys Arg His His Thr Arg Phe Tyr Pro Lys
         35                  40                  45
Asn Ser Gly Asp Ala Asp Lys Ser Ser Asn Leu Met Ala Gly Thr Val
     50                  55                  60
Val Asp Arg Gly Val Thr Glu Thr Arg Asn Trp Asp Phe Tyr Leu Gln
 65                  70                  75                  80
Ala His Ala Cys Leu Gln Gly Thr Ala Arg Ala Cys His Tyr Tyr Val
                 85                  90                  95
Ile Ile Asp Glu Ile Phe Arg Ser Asn Lys Val Lys Gly Gly His Lys
            100                 105                 110
Asn His Ala Asp Ala Leu Glu Glu Leu Thr Asn Asn Met Ser His Leu
        115                 120                 125
Phe Gly Arg Ala Thr Lys Ala Val Ser Leu Cys Pro Pro Ala Tyr Tyr
    130                 135                 140
Ala Asp Leu Leu Cys Thr Arg Val Arg Cys Tyr Leu Ser Glu Val Phe
145                 150                 155                 160
Asp Pro Ser Glu Ala Gln Ser Val Met Ser Gly Gly Thr Asn Gln Thr
                165                 170                 175
Ile Glu Asp Ile Val Ile Pro Pro Ser Met Arg Asp Ser Met Tyr Tyr
            180                 185                 190
Ile
```

<210> SEQ ID NO 45
<211> LENGTH: 327

```
<212> TYPE: DNA
<213> ORGANISM: Triticum aestivum

<400> SEQUENCE: 45
tgcgttctga catccattcg aggcccctct cagacgccga acgtgttaag atcaagaagg      60
cactgagagg agtaaaggtg gaagttactc atcgtggcaa catgcgaagg aagtaccgaa     120
tatctggtct gacaacccag gcaactcgag agctaacttt tcctgttgat gaaggggta      180 cagtaaagtc agtcgtacaa tactttcagg agacatatgg ctttgccatc cagcacacgt     240
acctgccttg cctccaagtt ggcaatcagc agcgtccaaa ttacttgggg gatcctctag     300
aggcgaccgg caggcataca agcttgg                                          327

<210> SEQ ID NO 46
<211> LENGTH: 95
<212> TYPE: PRT
<213> ORGANISM: Triticum aestivum

<400> SEQUENCE: 46

Arg Ser Asp Ile His Ser Arg Pro Leu Ser Asp Ala Glu Arg Val Lys
 1               5                  10                  15

Ile Lys Lys Ala Leu Arg Gly Val Lys Val Glu Val Thr His Arg Gly
            20                  25                  30

Asn Met Arg Arg Lys Tyr Arg Ile Ser Gly Leu Thr Thr Gln Ala Thr
        35                  40                  45

Arg Glu Leu Thr Phe Pro Val Asp Glu Gly Gly Thr Val Lys Ser Val
    50                  55                  60

Val Gln Tyr Phe Gln Glu Thr Tyr Gly Phe Ala Ile Gln His Thr Tyr
65                  70                  75                  80

Leu Pro Cys Leu Gln Val Gly Asn Gln Gln Arg Pro Asn Tyr Leu
                85                  90                  95

<210> SEQ ID NO 47
<211> LENGTH: 571
<212> TYPE: DNA
<213> ORGANISM: Triticum aestivum
<220> FEATURE:
<221> NAME/KEY: unsure
<222> LOCATION: (234)
<223> OTHER INFORMATION: n = A, C, G or T
<220> FEATURE:
<221> NAME/KEY: unsure
<222> LOCATION: (238)
<223> OTHER INFORMATION: n = A, C, G or T
<220> FEATURE:
<221> NAME/KEY: unsure
<222> LOCATION: (249)
<223> OTHER INFORMATION: n = A, C, G or T
<220> FEATURE:
<221> NAME/KEY: unsure
<222> LOCATION: (252)
<223> OTHER INFORMATION: n = A, C, G or T
<220> FEATURE:
<221> NAME/KEY: unsure
<222> LOCATION: (269)
<223> OTHER INFORMATION: n = A, C, G or T
<220> FEATURE:
<221> NAME/KEY: unsure
<222> LOCATION: (274)
<223> OTHER INFORMATION: n = A, C, G or T
<220> FEATURE:
<221> NAME/KEY: unsure
<222> LOCATION: (283)
<223> OTHER INFORMATION: n = A, C, G or T
<220> FEATURE:
<221> NAME/KEY: unsure
<222> LOCATION: (301)
```

```
<223> OTHER INFORMATION: n = A, C, G or T
<220> FEATURE:
<221> NAME/KEY: unsure
<222> LOCATION: (319)
<223> OTHER INFORMATION: n = A, C, G or T
<220> FEATURE:
<221> NAME/KEY: unsure
<222> LOCATION: (353)
<223> OTHER INFORMATION: n = A, C, G or T
<220> FEATURE:
<221> NAME/KEY: unsure
<222> LOCATION: (381)..(382)
<223> OTHER INFORMATION: n = A, C, G or T
<220> FEATURE:
<221> NAME/KEY: unsure
<222> LOCATION: (408)
<223> OTHER INFORMATION: n = A, C, G or T
<220> FEATURE:
<221> NAME/KEY: unsure
<222> LOCATION: (425)..(426)
<223> OTHER INFORMATION: n = A, C, G or T
<220> FEATURE:
<221> NAME/KEY: unsure
<222> LOCATION: (449)
<223> OTHER INFORMATION: n = A, C, G or T
<220> FEATURE:
<221> NAME/KEY: unsure
<222> LOCATION: (453)
<223> OTHER INFORMATION: n = A, C, G or T
<220> FEATURE:
<221> NAME/KEY: unsure
<222> LOCATION: (456)
<223> OTHER INFORMATION: n = A, C, G or T
<220> FEATURE:
<221> NAME/KEY: unsure
<222> LOCATION: (463)
<223> OTHER INFORMATION: n = A, C, G or T
<220> FEATURE:
<221> NAME/KEY: unsure
<222> LOCATION: (467)
<223> OTHER INFORMATION: n = A, C, G or T
<220> FEATURE:
<221> NAME/KEY: unsure
<222> LOCATION: (473)
<223> OTHER INFORMATION: n = A, C, G or T
<220> FEATURE:
<221> NAME/KEY: unsure
<222> LOCATION: (478)
<223> OTHER INFORMATION: n = A, C, G or T
<220> FEATURE:
<221> NAME/KEY: unsure
<222> LOCATION: (512)..(513)
<223> OTHER INFORMATION: n = A, C, G or T
<220> FEATURE:
<221> NAME/KEY: unsure
<222> LOCATION: (515)
<223> OTHER INFORMATION: n = A, C, G or T
<220> FEATURE:
<221> NAME/KEY: unsure
<222> LOCATION: (525)
<223> OTHER INFORMATION: n = A, C, G or T
<220> FEATURE:
<221> NAME/KEY: unsure
<222> LOCATION: (527)
<223> OTHER INFORMATION: n = A, C, G or T
<220> FEATURE:
<221> NAME/KEY: unsure
<222> LOCATION: (532)
<223> OTHER INFORMATION: n = A, C, G or T
<220> FEATURE:
<221> NAME/KEY: unsure
<222> LOCATION: (540)
<223> OTHER INFORMATION: n = A, C, G or T
<220> FEATURE:
<221> NAME/KEY: unsure
<222> LOCATION: (562)..(563)..(564)
<223> OTHER INFORMATION: n = A, C, G or T

<400> SEQUENCE: 47
```

```
attagtgtta ccaaaagtcg gcaagtggga catgtggtgc aagaaaatgg tcaatggagg      60
agtagttaac acctgggcat gcattaactt tgcttgggaa gtcacagatg ctcatgctct     120
gaattttgt  gatgagttgg tgctgatgtg caatgtatcc gggatggact tcaggcctga    180
acctgtgctc cctgtaacag cttatgaccc taaatccgta gcacggtcac tcanaganac    240
accataaang tntcatgaac atacctggnc cacngcgcca aanactcgac ctgctgattc    300
naatattgct gacaagtant ggcacccttt atggtgacat caggagaata ttnggacag     360
atattgggag tggtctctca nngttgtctt gcaaaacatg tttttaancc caaaaaacat    420
atttnncaat gttgcccttda aaataatgnt aangcnggag ganaaancgg tcntttangc   480
ttgaaaggaa cccccctatg ggaaaaaacg cnncnatttg ggcgnantag cntcaaaccn    540
gcaagggttc caccctccat gnnngtgtgg t                                   571
```

<210> SEQ ID NO 48
<211> LENGTH: 77
<212> TYPE: PRT
<213> ORGANISM: Triticum aestivum

<400> SEQUENCE: 48

Leu Val Leu Pro Lys Val Gly Lys Trp Asp Met Trp Cys Lys Lys Met
 1               5                  10                  15
Val Asn Gly Gly Val Val Asn Thr Trp Ala Cys Ile Asn Phe Ala Trp
            20                  25                  30
Glu Val Thr Asp Ala His Ala Leu Asn Phe Cys Asp Glu Leu Val Leu
        35                  40                  45
Met Cys Asn Val Ser Gly Met Asp Phe Arg Pro Glu Pro Val Leu Pro
    50                  55                  60
Val Thr Ala Tyr Asp Pro Lys Ser Val Ala Arg Ser Leu
65                  70                  75

<210> SEQ ID NO 49
<211> LENGTH: 1565
<212> TYPE: DNA
<213> ORGANISM: Triticum aestivum

<400> SEQUENCE: 49

```
actcgaatat gaggaccctc acactgtaat tgaagagagc ccgtcactga gacgagctcc     60
ggtggcacga agagtggagg agatgtttgc ccagataaag gccaagctac ctggagcacc    120
cttgtttctt ttgtgcctcc tccctgagag gaagaactgc gaagtttacg gtccttggaa    180
gaagaagtgt cttgctgatt tcggcatagt cacccaatgt ctagctccgc aaagagtcaa    240
tgaccagtac ttgagtaatc tgctactcaa gataaatgct aagctcggtg gactcaacac    300
actgcttcaa attgaagcag cccgtgcaat acccattgtg gggaaggtgc ctactatcat    360
cctgggcatg gatgtctcgc atggtcaacc tggccaatcc gacaggcctt ccattgctgc    420
ggtggtgagt tctcgtgagt ggcctctcat ctctaaatac agagcaacag tgcacactca    480
gtcacccaaa caggaggtga tggcttccct gtttaagcca cggggagctg aagatgatgg    540
ccttattcgg gaatctctta ttgacttgta cactagctct gggaagcgaa agccagacca    600
agttattatt ttcagggatg gagttagcga aagccagttt actcaggtga taaacattga    660
gcttgagcag atcattgagg catgcaagtg ccttgacgac aagtgggagc ccaagttcac    720
ggtcattgtt gctcagaaaa accatcatac caggttttc cagacaaact cgccagaaaa     780
tgttcctcct ggcactgtgg tggataaaca agtgtgccat cccaagaact tgacttcta     840
```

```
catgtgcgcg catgctggga tgattggcac gtcgaggcca acgcattacc atgttctgca    900
tgatgagatc ggcttcagtg gggatgagct ccaggagttt gtgcactcgc tctcctatgt    960
gtaccagagg agcacgacgg cgatatcagt agctgctccg atagcgtacg cgcatctggc   1020
ggcggcgcag gtgggcacct tcatgaagtt tgaggacatg tcggacacgt cgtcgagcca   1080
gggaggggc cacacgtctg cgggcagcgc cccggtgccg agctgcctc ggctgcacga   1140
gaaagtgagg agctccatgt tcttctgctg atctgatgct gctcttgaac ttgatcgatg   1200
ccgctttctg tcagtggagg ttgaaccgtg cgtctgtata aataaaacct actagtacct   1260
atctatctat gtactatcta gatggcacct ggaactttag ctgttatcca gggtgcccgt   1320
aagtcggtcc gttgtgtcgg gtgccgctgg gaacgttccc atggatgtta ccgtttgtgg   1380
tgttggcgtt gttgaaccaa ccaacctgac cctagcttaa ccttgcttgg attggatgat   1440
gtgctagcta gctagagcta gagctagagt tagaccatgc atggctgatg gtatgtattg   1500
tgggatcata tctatctatc tccatcctga cttggtgata aaaaaaaaaa aaaaaaaaa   1560
aaaaa                                                              1565

<210> SEQ ID NO 50
<211> LENGTH: 389
<212> TYPE: PRT
<213> ORGANISM: Triticum aestivum

<400> SEQUENCE: 50

Leu Glu Tyr Glu Asp Pro His Thr Val Ile Glu Glu Ser Pro Ser Leu
 1               5                  10                  15

Arg Arg Ala Pro Val Ala Arg Val Glu Glu Met Phe Ala Gln Ile
            20                  25                  30

Lys Ala Lys Leu Pro Gly Ala Pro Leu Phe Leu Leu Cys Leu Leu Pro
         35                  40                  45

Glu Arg Lys Asn Cys Glu Val Tyr Gly Pro Trp Lys Lys Lys Cys Leu
     50                  55                  60

Ala Asp Phe Gly Ile Val Thr Gln Cys Leu Ala Pro Gln Arg Val Asn
 65                  70                  75                  80

Asp Gln Tyr Leu Ser Asn Leu Leu Lys Ile Asn Ala Lys Leu Gly
             85                  90                  95

Gly Leu Asn Thr Leu Leu Gln Ile Glu Ala Ala Arg Ala Ile Pro Ile
            100                 105                 110

Val Gly Lys Val Pro Thr Ile Ile Leu Gly Met Asp Val Ser His Gly
        115                 120                 125

Gln Pro Gly Gln Ser Asp Arg Pro Ser Ile Ala Ala Val Val Ser Ser
    130                 135                 140

Arg Glu Trp Pro Leu Ile Ser Lys Tyr Arg Ala Thr Val His Thr Gln
145                 150                 155                 160

Ser Pro Lys Gln Glu Val Met Ala Ser Leu Phe Lys Pro Arg Gly Ala
                165                 170                 175

Glu Asp Asp Gly Leu Ile Arg Glu Ser Leu Ile Asp Leu Tyr Thr Ser
            180                 185                 190

Ser Gly Lys Arg Lys Pro Asp Gln Val Ile Ile Phe Arg Asp Gly Val
        195                 200                 205

Ser Glu Ser Gln Phe Thr Gln Val Ile Asn Ile Glu Leu Glu Gln Ile
    210                 215                 220

Ile Glu Ala Cys Lys Cys Leu Asp Asp Lys Trp Glu Pro Lys Phe Thr
225                 230                 235                 240
```

```
Val Ile Val Ala Gln Lys Asn His His Thr Arg Phe Phe Gln Thr Asn
                245                 250                 255

Ser Pro Glu Asn Val Pro Pro Gly Thr Val Val Asp Lys Gln Val Cys
            260                 265                 270

His Pro Lys Asn Phe Asp Phe Tyr Met Cys Ala His Ala Gly Met Ile
        275                 280                 285

Gly Thr Ser Arg Pro Thr His Tyr His Val Leu His Asp Glu Ile Gly
    290                 295                 300

Phe Ser Gly Asp Glu Leu Gln Glu Phe Val His Ser Leu Ser Tyr Val
305                 310                 315                 320

Tyr Gln Arg Ser Thr Thr Ala Ile Ser Val Ala Ala Pro Ile Ala Tyr
                325                 330                 335

Ala His Leu Ala Ala Ala Gln Val Gly Thr Phe Met Lys Phe Glu Asp
            340                 345                 350

Met Ser Asp Thr Ser Ser Ser Gln Gly Gly Gly His Thr Ser Ala Gly
        355                 360                 365

Ser Ala Pro Val Pro Glu Leu Pro Arg Leu His Glu Lys Val Arg Ser
    370                 375                 380

Ser Met Phe Phe Cys
385

<210> SEQ ID NO 51
<211> LENGTH: 541
<212> TYPE: DNA
<213> ORGANISM: Triticum aestivum
<220> FEATURE:
<221> NAME/KEY: unsure
<222> LOCATION: (33)
<223> OTHER INFORMATION: n = A, C, G or T
<220> FEATURE:
<221> NAME/KEY: unsure
<222> LOCATION: (95)
<223> OTHER INFORMATION: n = A, C, G or T

<400> SEQUENCE: 51
gattccatgt cctttgggat ggaacaattt acngcggatg tttacgatct cagaacaatt      60
tgtgtacact acgcaaggtg cacccgttct gtatngattg tgcctccggc atactatgct     120
cacctcgcgg cttttcgagc tcggttctac atggaaccgg atacctccga tggtggctcg     180
gtcgcgagcg gtgccacgac aagccgtgcc cctcctggtg cacgcggcgg cagtagagct     240
gcagggaatg ttgctgttaa gcctctgcct gagctcaagg aaaacgtgaa gcgtgtcatg     300
ttttactgct gataagttgg ggcaacgcct ccggggtccg ggctatctat tccccgtgat     360
cccaactgaa gtgcctgctg atttaccaat cctttctttg cggcagaaaa tcaatcatca     420
gtcatcacat gagtgtatct atatatgtat cagtgctgcc atgtttcctg tgcaacctga     480
acatctcaat tcctctttc atctacagat tttcaaatgg cattttccct gttaaaaaaa     540
a                                                                     541

<210> SEQ ID NO 52
<211> LENGTH: 103
<212> TYPE: PRT
<213> ORGANISM: Triticum aestivum
<220> FEATURE:
<221> NAME/KEY: UNSURE
<222> LOCATION: (32)
<223> OTHER INFORMATION: Xaa = ANY AMINO ACID

<400> SEQUENCE: 52
```

```
Asp Ser Met Ser Phe Gly Met Glu Gln Phe Thr Ala Asp Val Tyr Asp
 1               5                  10                  15

Leu Arg Thr Ile Cys Val His Tyr Ala Arg Cys Thr Arg Ser Val Xaa
            20                  25                  30

Ile Val Pro Pro Ala Tyr Tyr Ala His Leu Ala Ala Phe Arg Ala Arg
        35                  40                  45

Phe Tyr Met Glu Pro Asp Thr Ser Asp Gly Gly Ser Val Ala Ser Gly
    50                  55                  60

Ala Thr Thr Ser Arg Ala Pro Pro Gly Ala Arg Gly Gly Ser Arg Ala
65                  70                  75                  80

Ala Gly Asn Val Ala Val Lys Pro Leu Pro Glu Leu Lys Glu Asn Val
                85                  90                  95

Lys Arg Val Met Phe Tyr Cys
            100
```

<210> SEQ ID NO 53
<211> LENGTH: 3705
<212> TYPE: DNA
<213> ORGANISM: Oryza sativa
<220> FEATURE:
<221> NAME/KEY: unsure
<222> LOCATION: (3616)
<223> OTHER INFORMATION: n = A, C, G or T

<400> SEQUENCE: 53

| | | | | | |
|---|---|---|---|---|---|
| gagcagcagt | gcggtagtgc | aagcgctagt | ggaggagttg | ggaggaggcc | cctagggtt | 60 |
| tcccgagacc | gcctccccc | cgcctgcgc | cgccgctcgc | cgagcgcgcg | ctccgtgccc | 120 |
| atcatggtga | agaagaaaag | aactgggtct | ggcagcaccg | gtgagagttc | tggagaggct | 180 |
| ccaggagctc | ctggccatgg | ttcttcacag | cgagctgaga | gaggtcctca | acagcatggg | 240 |
| ggaggacgtg | gttgggtgcc | tcaacatggt | ggccgtggtg | gtgggcaata | ccagggccgt | 300 |
| ggtggacatt | atcagggccg | tggagggcaa | ggttcacacc | atccaggtgg | agggcctcct | 360 |
| gagtatcagg | gtcgtggagg | gccaggttca | catcatccag | gtggtgggcc | tcctgactat | 420 |
| cagggccgtg | gaggatcagg | ttcacatcac | ccaggtggtg | ggcctcccga | gtatcaaccg | 480 |
| cgtgactatc | aaggacgtgg | tggtccacgc | cccagaggtg | aatgccaca | gccatactat | 540 |
| ggcggaccta | gggggagtgg | cggacgtagt | gttccttcag | gttcatcaag | aacagttccc | 600 |
| gagctgcacc | aagccccaca | tgtccaatac | caagccccga | tggtttcacc | aaccccatcg | 660 |
| ggagctggct | catcctctca | gcctgcggcg | gaggtgagca | gtggacaagt | ccaacaacag | 720 |
| tttcagcaac | ttgccacccg | tgatcaaagt | tcgaccagcc | aagccattca | aatagcacca | 780 |
| ccgtcaagca | aatcagttag | attcccgttg | cgccctggca | agggtacata | tggggacagg | 840 |
| tgcattgtga | aggcgaacca | tttctttgct | gaacttcctg | ataaagacct | tcaccaatac | 900 |
| gacgtatcta | ttactcctga | ggttacttca | cgtggcgtga | atcgtgctgt | tatgtttgag | 960 |
| ttagtaacgc | tgtatagata | ttcccatttg | gcgggcgtc | tacctgccta | tgatggaagg | 1020 |
| aagagtcttt | acacagctgg | accattgcca | tttgcttcta | ggacatttga | aattactctt | 1080 |
| caagatgagg | aagatagtct | tggtggtggc | caaggcaccc | aaaggcgtga | gagactattt | 1140 |
| agggtggtga | tcaagtttgc | tgcccgtgct | gatcttcacc | atttggctat | gtttctagct | 1200 |
| ggaaggcaag | cagatgctcc | tcaagaagcc | cttcaagtcc | ttgacattgt | gttacgtgaa | 1260 |
| ttgcctacca | caaggtactc | accagttggt | cggtcatttt | attctcccaa | tttagggaga | 1320 |
| cgccagcaac | ttggtgaggg | tttggaaagt | tggcgtggtt | tttaccaaag | cataaggcct | 1380 |

```
acccagatgg gtctctcact gaatattgat atgtcatcaa ctgcatttat tgagcctcta    1440
cctgtgattg actttgttgc tcagcttctg aacagagaca tctcagttag accattatct    1500
gattctgatc gtgtgaagat aaagaaagct ctaagaggtg tgaaggttga ggtgacgcat    1560
agaggaaaca tgcgtagaaa atatcgtata tctggactca cttcacaggc aacaagggag    1620
ttatcattcc ctgtcgatga tcgtggtact gtgaagactg tggtgcaata ttttctggag    1680
acatatggtt ttagtattca gcacaccact ttgccttgcc ttcaagtggg caatcagcaa    1740
aggcccaatt atctgcctat ggaggtttgt aagatcgttg agggacagcg ttactcgaag    1800
cggcttaacg agaaacagat tactgcgcta ttgaaagtga cttgccagcg acctcaagag    1860
cgtgaactgg atattttgcg gactgtatct cacaatgcat accatgaaga tcagtatgcg    1920
caggaatttg gcataaaaat tgatgagcgt cttgcatctg ttgaagctcg tgttctgcct    1980
cccccaaggc ttaaatacca tgatagtggg agagaaaagg atgtattgcc gagagttggc    2040
cagtggaaca tgatgaataa gaaaatggtc aatggtggga gagtcaacaa ctgggcatgt    2100
attaacttct ctagaaatgt gcaagatagt gctgccaggg gcttctgtca tgagctggct    2160
atcatgtgcc aaatatctgg aatggatttt gcactggaac ctgtgctgcc cccacttact    2220
gctagaccta acatgtggaa aagagcactg aaggcacgct atcaagatgc aatgaacatg    2280
ctcagaccgc agggcaggga acttgattta ctgattgtaa tactgcctga caataatggt    2340
tctctttatg gggatctcaa aagaatctgt gagactgatc ttggattggt ctcccaatgt    2400
tgtttgacaa acatgttttt taaaatgagc aagcagtatc ttgcaaatgt tgcccttaaa    2460
ataaacgtta aggtggggggg aaggaatact gtacttgtgg atgctttgac aaggaggatt    2520
ccccttgtca gtgacagacc aactatcata tttggtgcgg atgttactca tcctcatcct    2580
ggagaagatt ccagtccttc cattgcagct gtggttgctt ctcaagactg gcctgaagtc    2640
actaagtatg ctggattggt gagtgcccaa gcccatcgtc aagaattgat acaagatctt    2700
ttcaaagtat ggcaagaccc gcatagagga actgttactg gtggcatgat caaggagctt    2760
ctcatttctt tcaagagggc tactggacag aaacctcaga ggataatatt ttacagggat    2820
ggtgtcagcg aggggcagtt ttatcaagtt ttgttgtatg agcttgatgc cattagaaag    2880
gcttgtgcat ccctggaacc caactatcag cctccagtta cctttgtggt ggtccagaag    2940
cggcatcaca caaggttgtt tgctaataat cacaacgacc agcgtactgt tgatagaagt    3000
ggaaacattc tgcctggaac tgttgttgac tcaaagattt gccatccaac cgagtttgat    3060
ttctacctgt gtagccatgc tggcatacag ggaacaagcc gtcctgctca ttatcatgtt    3120
ctgtgggatg agaacaaatt tactgcagac gagttgcaaa ccctcacgaa caacttgtgc    3180
tacacgtatg caaggtgcac tcgctctgta tcaattgtgc ctcctgcgta ctatgctcat    3240
ctggcagcct tccgagctcg cttttacatg gagccagaga catctgacag tggatcaatg    3300
gcgagtggag ctgcaacgag ccgtggcctt ccaccaggtg tgcgcagcgc cagggttgct    3360
ggaaatgtag ccgtcaggcc tctacctgct ctcaaggaaa acgtgaagcg tgtcatgttt    3420
tactgctaag agcttgggct gtaccccgta tgcgccaagg aatgtagtac tatgttatgt    3480
tattttagca cttgcactct gtcgttgatc ccgttaaaac gggtatgcta ccataagctg    3540
ttggactatt ctgggtattg tagtactact tgttttgtat ttgtgtttgt gacgctgcag    3600
agcgtgaaca acgcanaaaa aaaaaaaaaa aaaaaaaaaa aaaaaaaaaa aaaaaaaaaa    3660
aaaaaaaaaa aaaccaaaaa aaaaaaaaaa aaaaaaaaaa aaaaa                   3705
```

<210> SEQ ID NO 54
<211> LENGTH: 1101
<212> TYPE: PRT
<213> ORGANISM: Oryza sativa

<400> SEQUENCE: 54

| | | | | | | | | | | | | | | |
|---|---|---|---|---|---|---|---|---|---|---|---|---|---|---|
| Met | Val | Lys | Lys | Lys | Arg | Thr | Gly | Ser | Gly | Ser | Thr | Gly | Glu | Ser | Ser |
| 1 | | | | 5 | | | | | 10 | | | | | 15 | |
| Gly | Glu | Ala | Pro | Gly | Ala | Pro | Gly | His | Gly | Ser | Ser | Gln | Arg | Ala | Glu |
| | | | 20 | | | | | 25 | | | | | 30 | | |
| Arg | Gly | Pro | Gln | Gln | His | Gly | Gly | Arg | Gly | Trp | Val | Pro | Gln | His | |
| | | 35 | | | | | 40 | | | | | 45 | | | |
| Gly | Gly | Arg | Gly | Gly | Gln | Tyr | Gln | Gly | Arg | Gly | His | Tyr | Gln | | |
| | 50 | | | | | 55 | | | | | 60 | | | | |
| Gly | Arg | Gly | Gly | Gln | Gly | Ser | His | His | Pro | Gly | Gly | Pro | Glu | | |
| 65 | | | | | 70 | | | | | 75 | | | | 80 | |
| Tyr | Gln | Gly | Arg | Gly | Gly | Pro | Gly | Ser | His | His | Pro | Gly | Gly | Pro | |
| | | | | 85 | | | | | 90 | | | | | 95 | |
| Pro | Asp | Tyr | Gln | Gly | Arg | Gly | Gly | Ser | Gly | Ser | His | His | Pro | Gly | Gly |
| | | | 100 | | | | | 105 | | | | | 110 | | |
| Gly | Pro | Pro | Glu | Tyr | Gln | Pro | Arg | Asp | Tyr | Gln | Gly | Arg | Gly | Gly | Pro |
| | | 115 | | | | | 120 | | | | | 125 | | | |
| Arg | Pro | Arg | Gly | Gly | Met | Pro | Gln | Pro | Tyr | Tyr | Gly | Gly | Pro | Arg | Gly |
| 130 | | | | | 135 | | | | | 140 | | | | | |
| Ser | Gly | Gly | Arg | Ser | Val | Pro | Ser | Gly | Ser | Ser | Arg | Thr | Val | Pro | Glu |
| 145 | | | | | 150 | | | | | 155 | | | | | 160 |
| Leu | His | Gln | Ala | Pro | His | Val | Gln | Tyr | Gln | Ala | Pro | Met | Val | Ser | Pro |
| | | | | 165 | | | | | 170 | | | | | 175 | |
| Thr | Pro | Ser | Gly | Ala | Gly | Ser | Ser | Ser | Gln | Pro | Ala | Ala | Glu | Val | Ser |
| | | | 180 | | | | | 185 | | | | | 190 | | |
| Ser | Gly | Gln | Val | Gln | Gln | Gln | Phe | Gln | Gln | Leu | Ala | Thr | Arg | Asp | Gln |
| | | 195 | | | | | 200 | | | | | 205 | | | |
| Ser | Ser | Thr | Ser | Gln | Ala | Ile | Gln | Ile | Ala | Pro | Pro | Ser | Ser | Lys | Ser |
| | 210 | | | | | 215 | | | | | 220 | | | | |
| Val | Arg | Phe | Pro | Leu | Arg | Pro | Gly | Lys | Gly | Thr | Tyr | Gly | Asp | Arg | Cys |
| 225 | | | | | 230 | | | | | 235 | | | | | 240 |
| Ile | Val | Lys | Ala | Asn | His | Phe | Phe | Ala | Glu | Leu | Pro | Asp | Lys | Asp | Leu |
| | | | | 245 | | | | | 250 | | | | | 255 | |
| His | Gln | Tyr | Asp | Val | Ser | Ile | Thr | Pro | Glu | Val | Thr | Ser | Arg | Gly | Val |
| | | | 260 | | | | | 265 | | | | | 270 | | |
| Asn | Arg | Ala | Val | Met | Phe | Glu | Leu | Val | Thr | Leu | Tyr | Arg | Tyr | Ser | His |
| | | 275 | | | | | 280 | | | | | 285 | | | |
| Leu | Gly | Gly | Arg | Leu | Pro | Ala | Tyr | Asp | Gly | Arg | Lys | Ser | Leu | Tyr | Thr |
| | 290 | | | | | 295 | | | | | 300 | | | | |
| Ala | Gly | Pro | Leu | Pro | Phe | Ala | Ser | Arg | Thr | Phe | Glu | Ile | Thr | Leu | Gln |
| 305 | | | | | 310 | | | | | 315 | | | | | 320 |
| Asp | Glu | Glu | Asp | Ser | Leu | Gly | Gly | Gln | Gly | Thr | Gln | Arg | Arg | Glu | |
| | | | | 325 | | | | | 330 | | | | | 335 | |
| Arg | Leu | Phe | Arg | Val | Val | Ile | Lys | Phe | Ala | Ala | Arg | Ala | Asp | Leu | His |
| | | | 340 | | | | | 345 | | | | | 350 | | |
| His | Leu | Ala | Met | Phe | Leu | Ala | Gly | Arg | Gln | Ala | Asp | Ala | Pro | Gln | Glu |
| | | | 355 | | | | | 360 | | | | | 365 | | |
| Ala | Leu | Gln | Val | Leu | Asp | Ile | Val | Leu | Arg | Glu | Leu | Pro | Thr | Thr | Arg |
| | 370 | | | | | 375 | | | | | 380 | | | | |

```
Tyr Ser Pro Val Gly Arg Ser Phe Tyr Ser Pro Asn Leu Gly Arg Arg
385                 390                 395                 400

Gln Gln Leu Gly Glu Gly Leu Glu Ser Trp Arg Gly Phe Tyr Gln Ser
            405                 410                 415

Ile Arg Pro Thr Gln Met Gly Leu Ser Leu Asn Ile Asp Met Ser Ser
                420                 425                 430

Thr Ala Phe Ile Glu Pro Leu Pro Val Ile Asp Phe Val Ala Gln Leu
            435                 440                 445

Leu Asn Arg Asp Ile Ser Val Arg Pro Leu Ser Asp Ser Asp Arg Val
    450                 455                 460

Lys Ile Lys Lys Ala Leu Arg Gly Val Lys Val Glu Val Thr His Arg
465                 470                 475                 480

Gly Asn Met Arg Arg Lys Tyr Arg Ile Ser Gly Leu Thr Ser Gln Ala
                485                 490                 495

Thr Arg Glu Leu Ser Phe Pro Val Asp Asp Arg Gly Thr Val Lys Thr
            500                 505                 510

Val Val Gln Tyr Phe Leu Glu Thr Tyr Gly Phe Ser Ile Gln His Thr
    515                 520                 525

Thr Leu Pro Cys Leu Gln Val Gly Asn Gln Gln Arg Pro Asn Tyr Leu
    530                 535                 540

Pro Met Glu Val Cys Lys Ile Val Glu Gly Gln Arg Tyr Ser Lys Arg
545                 550                 555                 560

Leu Asn Glu Lys Gln Ile Thr Ala Leu Leu Lys Val Thr Cys Gln Arg
                565                 570                 575

Pro Gln Glu Arg Glu Leu Asp Ile Leu Arg Thr Val Ser His Asn Ala
            580                 585                 590

Tyr His Glu Asp Gln Tyr Ala Gln Glu Phe Gly Ile Lys Ile Asp Glu
    595                 600                 605

Arg Leu Ala Ser Val Glu Ala Arg Val Leu Pro Pro Arg Leu Lys
    610                 615                 620

Tyr His Asp Ser Gly Arg Glu Lys Asp Val Leu Pro Arg Val Gly Gln
625                 630                 635                 640

Trp Asn Met Met Asn Lys Lys Met Val Asn Gly Gly Arg Val Asn Asn
                645                 650                 655

Trp Ala Cys Ile Asn Phe Ser Arg Asn Val Gln Asp Ser Ala Ala Arg
            660                 665                 670

Gly Phe Cys His Glu Leu Ala Ile Met Cys Gln Ile Ser Gly Met Asp
    675                 680                 685

Phe Ala Leu Glu Pro Val Leu Pro Pro Leu Thr Ala Arg Pro Glu His
    690                 695                 700

Val Glu Arg Ala Leu Lys Ala Arg Tyr Gln Asp Ala Met Asn Met Leu
705                 710                 715                 720

Arg Pro Gln Gly Arg Glu Leu Asp Leu Leu Ile Val Ile Leu Pro Asp
                725                 730                 735

Asn Asn Gly Ser Leu Tyr Gly Asp Leu Lys Arg Ile Cys Glu Thr Asp
            740                 745                 750

Leu Gly Leu Val Ser Gln Cys Cys Leu Thr Lys His Val Phe Lys Met
    755                 760                 765

Ser Lys Gln Tyr Leu Ala Asn Val Ala Leu Lys Ile Asn Val Lys Val
    770                 775                 780

Gly Gly Arg Asn Thr Val Leu Val Asp Ala Leu Thr Arg Arg Ile Pro
785                 790                 795                 800

Leu Val Ser Asp Arg Pro Thr Ile Ile Phe Gly Ala Asp Val Thr His
```

```
                    805                 810                 815
Pro His Pro Gly Glu Asp Ser Ser Pro Ser Ile Ala Ala Val Val Ala
            820                 825                 830

Ser Gln Asp Trp Pro Glu Val Thr Lys Tyr Ala Gly Leu Val Ser Ala
            835                 840                 845

Gln Ala His Arg Gln Glu Leu Ile Gln Asp Leu Phe Lys Val Trp Gln
            850                 855                 860

Asp Pro His Arg Gly Thr Val Thr Gly Gly Met Ile Lys Glu Leu Leu
865                 870                 875                 880

Ile Ser Phe Lys Arg Ala Thr Gly Gln Lys Pro Gln Arg Ile Ile Phe
            885                 890                 895

Tyr Arg Asp Gly Val Ser Glu Gly Gln Phe Tyr Gln Val Leu Leu Tyr
            900                 905                 910

Glu Leu Asp Ala Ile Arg Lys Ala Cys Ala Ser Leu Glu Pro Asn Tyr
            915                 920                 925

Gln Pro Pro Val Thr Phe Val Val Gln Lys Arg His His Thr Arg
            930                 935                 940

Leu Phe Ala Asn Asn His Asn Asp Gln Arg Thr Val Asp Arg Ser Gly
945                 950                 955                 960

Asn Ile Leu Pro Gly Thr Val Val Asp Ser Lys Ile Cys His Pro Thr
            965                 970                 975

Glu Phe Asp Phe Tyr Leu Cys Ser His Ala Gly Ile Gln Gly Thr Ser
            980                 985                 990

Arg Pro Ala His Tyr His Val Leu Trp Asp Glu Asn Lys Phe Thr Ala
            995                 1000                1005

Asp Glu Leu Gln Thr Leu Thr Asn Asn Leu Cys Tyr Thr Tyr Ala Arg
1010                1015                1020

Cys Thr Arg Ser Val Ser Ile Val Pro Pro Ala Tyr Tyr Ala His Leu
1025                1030                1035                1040

Ala Ala Phe Arg Ala Arg Phe Tyr Met Glu Pro Glu Thr Ser Asp Ser
            1045                1050                1055

Gly Ser Met Ala Ser Gly Ala Ala Thr Ser Arg Gly Leu Pro Pro Gly
            1060                1065                1070

Val Arg Ser Ala Arg Val Ala Gly Asn Val Ala Val Arg Pro Leu Pro
            1075                1080                1085

Ala Leu Lys Glu Asn Val Lys Arg Val Met Phe Tyr Cys
            1090                1095                1100

<210> SEQ ID NO 55
<211> LENGTH: 904
<212> TYPE: PRT
<213> ORGANISM: Oryza sativa

<400> SEQUENCE: 55

Met Glu Ser Asn Ser Gly Glu Ile Glu Glu Leu Pro Pro Pro Pro
1               5                   10                  15

Leu Pro Pro Asn Ala Glu Pro Ile Lys Thr Asp Asp Thr Lys Lys Leu
            20                  25                  30

Ser Lys Pro Lys Arg Ala Leu Met Ala Arg Ser Gly Cys Gly Lys Lys
        35                  40                  45

Gly Gln Pro Ile Gln Leu Leu Thr Asn His Phe Lys Val Ser Leu Lys
    50                  55                  60

Ala Ala Asp Glu Phe Phe His Tyr Tyr Val Asn Leu Lys Tyr Glu
65              70                  75                  80
```

```
Asp Asp Arg Pro Val Asp Gly Lys Gly Ile Gly Arg Lys Val Leu Asp
             85                  90                  95

Lys Leu Gln Gln Thr Tyr Ala Ser Glu Leu Ala Asn Lys Asp Phe Ala
            100                 105                 110

Tyr Asp Gly Glu Lys Ser Leu Phe Thr Ile Gly Ala Leu Pro Gln Val
            115                 120                 125

Asn Asn Glu Phe Thr Val Val Leu Glu Asp Phe Asn Thr Gly Lys Ser
        130                 135                 140

Ser Ala Asn Gly Gly Ser Pro Gly Asn Asp Ser Pro Gly Asn Asp Arg
145                 150                 155                 160

Lys Arg Val Arg Arg Pro Tyr Gln Thr Lys Thr Phe Lys Val Glu Leu
                165                 170                 175

Asn Phe Ala Ala Lys Ile Pro Met Ser Ala Ile Ala Gln Ala Leu Arg
            180                 185                 190

Gly Gln Glu Ser Glu Asn Thr Gln Glu Ala Ile Arg Val Ile Asp Ile
            195                 200                 205

Ile Leu Arg Gln His Ser Ala Lys Gln Gly Cys Leu Leu Val Arg Gln
        210                 215                 220

Ser Phe Phe His Asn Asn Pro Ser Asn Phe Val Asp Leu Gly Gly Gly
225                 230                 235                 240

Val Met Gly Cys Arg Gly Phe His Ser Ser Phe Arg Ala Thr Gln Ser
                245                 250                 255

Gly Leu Ser Leu Asn Ile Asp Val Ser Thr Thr Met Ile Val Lys Pro
            260                 265                 270

Gly Pro Val Val Asp Phe Leu Leu Ala Asn Gln Lys Val Asp His Pro
            275                 280                 285

Asn Lys Ile Asp Trp Ala Lys Ala Lys Arg Ala Leu Lys Asn Leu Arg
        290                 295                 300

Ile Lys Thr Ser Pro Ala Asn Thr Glu Tyr Lys Ile Val Gly Leu Ser
305                 310                 315                 320

Glu Arg Asn Cys Tyr Glu Gln Met Phe Thr Leu Lys Gln Arg Asn Gly
                325                 330                 335

Asp Gly Glu Pro Glu Gly Val Glu Val Ser Val Tyr Glu Tyr Phe Val
            340                 345                 350

Lys Asn Arg Gly Ile Glu Leu Arg Tyr Ser Gly Asp Phe Pro Cys Ile
        355                 360                 365

Asn Val Gly Lys Pro Lys Arg Pro Thr Tyr Phe Pro Ile Glu Leu Cys
        370                 375                 380

Ser Leu Val Pro Leu Gln Arg Tyr Thr Lys Ala Leu Ser Thr Leu Gln
385                 390                 395                 400

Arg Ser Ser Leu Val Glu Lys Ser Arg Gln Lys Pro Glu Glu Arg Met
                405                 410                 415

Ser Val Leu Ser Asp Val Leu Lys Arg Ser Asn Tyr Asp Ser Glu Pro
            420                 425                 430

Met Leu Asn Ser Cys Gly Ile Ser Ile Ala Arg Gly Phe Thr Gln Val
        435                 440                 445

Ala Gly Arg Val Leu Gln Ala Pro Lys Leu Lys Ala Gly Asn Gly Glu
450                 455                 460

Asp Leu Phe Ala Arg Asn Gly Arg Trp Asn Phe Asn Asn Lys Arg Leu
465                 470                 475                 480

Ile Lys Ala Ser Ser Ile Glu Lys Trp Ala Val Val Asn Phe Ser Ala
                485                 490                 495

Arg Cys Asn Ile Arg Asp Leu Val Arg Asp Ile Ile Lys Cys Gly Gly
```

```
                500                 505                 510
Met Lys Gly Ile Lys Val Glu Asp Pro Phe Asp Val Ile Glu Glu Asp
            515                 520                 525

Pro Ser Met Arg Arg Ala Pro Ala Ala Arg Val Asp Gly Met Ile
530                 535                 540

Asp Lys Met Gln Lys Leu Pro Gly Gln Pro Lys Phe Leu Leu Cys
545                 550                 555                 560

Val Leu Ala Glu Arg Lys Asn Ser Asp Ile Tyr Gly Pro Trp Lys Arg
                565                 570                 575

Lys Cys Leu Ala Glu Phe Gly Ile Ile Thr Gln Cys Val Ala Pro Thr
            580                 585                 590

Arg Val Asn Asp Gln Tyr Ile Thr Asn Val Leu Leu Lys Ile Asn Ala
            595                 600                 605

Lys Leu Gly Gly Leu Asn Ser Leu Leu Gln Ile Glu Thr Ser Pro Ser
            610                 615                 620

Ile Pro Leu Val Ser Lys Val Pro Thr Ile Ile Leu Gly Met Asp Val
625                 630                 635                 640

Ser His Gly Ser Pro Gly Gln Ser Asp Ile Pro Ser Ile Ala Ala Val
                645                 650                 655

Val Ser Ser Arg Glu Trp Pro Leu Val Ser Lys Tyr Arg Ala Ser Val
            660                 665                 670

Arg Ser Gln Ser Pro Lys Leu Glu Met Ile Asp Gly Leu Phe Lys Pro
            675                 680                 685

Gln Gly Ala Gln Glu Asp Asp Gly Leu Ile Arg Glu Leu Leu Val Asp
            690                 695                 700

Phe Tyr Thr Ser Thr Gly Lys Arg Lys Pro Asp Gln Val Ile Ile Phe
705                 710                 715                 720

Arg Asp Gly Val Ser Glu Ser Gln Phe Thr Gln Val Leu Asn Ile Glu
                725                 730                 735

Leu Asp Gln Ile Ile Glu Ala Cys Lys Phe Leu Asp Glu Asn Trp Ser
            740                 745                 750

Pro Lys Phe Thr Leu Ile Val Ala Gln Lys Asn His His Thr Lys Phe
            755                 760                 765

Phe Val Pro Gly Ser Gln Asn Asn Val Pro Pro Gly Thr Val Val Asp
770                 775                 780

Asn Ala Val Cys His Pro Arg Asn Asn Asp Phe Tyr Met Cys Ala His
785                 790                 795                 800

Ala Gly Met Ile Gly Thr Thr Arg Pro Thr His Tyr His Ile Leu His
                805                 810                 815

Asp Glu Ile Gly Phe Ser Ala Asp Asp Leu Gln Glu Leu Val His Ser
            820                 825                 830

Leu Ser Tyr Val Tyr Gln Arg Ser Thr Thr Ala Ile Ser Val Val Ala
            835                 840                 845

Pro Ile Cys Tyr Ala His Leu Ala Ala Ala Gln Val Ser Gln Phe Ile
            850                 855                 860

Lys Phe Asp Glu Met Ser Glu Thr Ser Ser Ser His Gly Gly His Thr
865                 870                 875                 880

Ser Ala Gly Ser Ala Pro Val Pro Glu Leu Pro Arg Leu His Asn Lys
                885                 890                 895

Val Arg Ser Ser Met Phe Phe Cys
                900

<210> SEQ ID NO 56
```

```
<211> LENGTH: 1048
<212> TYPE: PRT
<213> ORGANISM: Arabidopsis thaliana

<400> SEQUENCE: 56
```

| | | | | | | | | | | | | | | | |
|---|---|---|---|---|---|---|---|---|---|---|---|---|---|---|---|
| Met | Val | Arg | Lys | Arg | Thr | Asp | Ala | Pro | Ser | Glu | Gly | Gly | Glu | Gly | |
| 1 | | | | 5 | | | | | 10 | | | | | 15 | |
| Ser | Gly | Ser | Arg | Glu | Ala | Gly | Pro | Val | Ser | Gly | Gly | Arg | Gly | Ser | |
| | | | 20 | | | | | 25 | | | | | 30 | | |
| Gln | Arg | Gly | Gly | Phe | Gln | Gln | Gly | Gly | Gln | His | Gln | Gly | Gly | Arg | |
| | | 35 | | | | | 40 | | | | | 45 | | | |
| Gly | Tyr | Thr | Pro | Gln | Pro | Gln | Gln | Gly | Gly | Arg | Gly | Gly | Arg | Gly | Tyr |
| | 50 | | | | | 55 | | | | | 60 | | | | |
| Gly | Gln | Pro | Pro | Gln | Gln | Gln | Gln | Tyr | Gly | Gly | Pro | Gln | Glu | Tyr | |
| 65 | | | | | 70 | | | | | 75 | | | | | 80 |
| Gln | Gly | Arg | Gly | Arg | Gly | Gly | Pro | His | Gln | Gly | Gly | Arg | Gly | Gly | |
| | | | | 85 | | | | | 90 | | | | | 95 | |
| Tyr | Gly | Gly | Gly | Arg | Gly | Gly | Pro | Ser | Ser | Gly | Pro | Pro | Gln | Arg | |
| | | | 100 | | | | | 105 | | | | | 110 | | |
| Gln | Ser | Val | Pro | Glu | Leu | His | Gln | Ala | Thr | Ser | Pro | Thr | Tyr | Gln | Ala |
| | | 115 | | | | | 120 | | | | | 125 | | | |
| Val | Ser | Ser | Gln | Pro | Thr | Leu | Ser | Glu | Val | Ser | Pro | Thr | Gln | Val | Pro |
| | 130 | | | | | 135 | | | | | 140 | | | | |
| Glu | Pro | Thr | Val | Leu | Ala | Gln | Gln | Phe | Glu | Gln | Leu | Ser | Val | Glu | Gln |
| 145 | | | | | 150 | | | | | 155 | | | | | 160 |
| Gly | Ala | Pro | Ser | Gln | Ala | Ile | Gln | Pro | Ile | Pro | Ser | Ser | Lys | Ala | |
| | | | | 165 | | | | | 170 | | | | | 175 | |
| Phe | Lys | Phe | Pro | Met | Arg | Pro | Gly | Lys | Gly | Gln | Ser | Gly | Lys | Arg | Cys |
| | | | 180 | | | | | 185 | | | | | 190 | | |
| Ile | Val | Lys | Ala | Asn | His | Phe | Phe | Ala | Glu | Leu | Pro | Asp | Lys | Asp | Leu |
| | | 195 | | | | | 200 | | | | | 205 | | | |
| His | His | Tyr | Asp | Val | Thr | Ile | Thr | Pro | Glu | Val | Thr | Ser | Arg | Gly | Val |
| | 210 | | | | | 215 | | | | | 220 | | | | |
| Asn | Arg | Ala | Val | Met | Lys | Gln | Leu | Val | Asp | Asn | Tyr | Arg | Asp | Ser | His |
| 225 | | | | | 230 | | | | | 235 | | | | | 240 |
| Leu | Gly | Ser | Arg | Leu | Pro | Ala | Tyr | Asp | Gly | Arg | Lys | Ser | Leu | Tyr | Thr |
| | | | | 245 | | | | | 250 | | | | | 255 | |
| Ala | Gly | Pro | Leu | Pro | Phe | Asn | Ser | Lys | Glu | Phe | Arg | Ile | Asn | Leu | Leu |
| | | | 260 | | | | | 265 | | | | | 270 | | |
| Asp | Glu | Glu | Val | Gly | Ala | Gly | Gly | Gln | Arg | Arg | Glu | Arg | Glu | Phe | Lys |
| | | 275 | | | | | 280 | | | | | 285 | | | |
| Val | Val | Ile | Lys | Leu | Val | Ala | Arg | Ala | Asp | Leu | His | His | Leu | Gly | Met |
| | 290 | | | | | 295 | | | | | 300 | | | | |
| Phe | Leu | Glu | Gly | Lys | Gln | Ser | Asp | Ala | Pro | Gln | Glu | Ala | Leu | Gln | Val |
| 305 | | | | | 310 | | | | | 315 | | | | | 320 |
| Leu | Asp | Ile | Val | Leu | Arg | Glu | Leu | Pro | Thr | Ser | Arg | Tyr | Ile | Pro | Val |
| | | | | 325 | | | | | 330 | | | | | 335 | |
| Gly | Arg | Ser | Phe | Tyr | Ser | Pro | Asp | Ile | Gly | Lys | Lys | Gln | Ser | Leu | Gly |
| | | | 340 | | | | | 345 | | | | | 350 | | |
| Asp | Gly | Leu | Glu | Ser | Trp | Arg | Gly | Phe | Tyr | Gln | Ser | Ile | Arg | Pro | Thr |
| | | 355 | | | | | 360 | | | | | 365 | | | |
| Gln | Met | Gly | Leu | Ser | Leu | Asn | Ile | Asp | Met | Ser | Ser | Thr | Ala | Phe | Ile |
| | 370 | | | | | 375 | | | | | 380 | | | | |
| Glu | Ala | Asn | Pro | Val | Ile | Gln | Phe | Val | Cys | Asp | Leu | Leu | Asn | Arg | Asp |

```
                385                 390                 395                 400
            Ile Ser Ser Arg Pro Leu Ser Asp Ala Asp Arg Val Lys Ile Lys Lys
                            405                 410                 415

Ala Leu Arg Gly Val Lys Val Glu Val Thr His Arg Gly Asn Met Arg
                            420                 425                 430

Arg Lys Tyr Arg Ile Ser Gly Leu Thr Ala Val Ala Thr Arg Glu Leu
                            435                 440                 445

Thr Phe Pro Val Asp Glu Arg Asn Thr Gln Lys Ser Val Val Glu Tyr
                        450                 455                 460

Phe His Glu Thr Tyr Gly Phe Arg Ile Gln His Thr Gln Leu Pro Cys
            465                 470                 475                 480

Leu Gln Val Gly Asn Ser Asn Arg Pro Asn Tyr Leu Pro Met Glu Val
                            485                 490                 495

Cys Lys Ile Val Glu Gly Gln Arg Tyr Ser Lys Arg Leu Asn Glu Arg
                            500                 505                 510

Gln Ile Thr Ala Leu Leu Lys Val Thr Cys Gln Arg Pro Ile Asp Arg
                        515                 520                 525

Glu Lys Asp Ile Leu Gln Thr Val Gln Leu Asn Asp Tyr Ala Lys Asp
                    530                 535                 540

Asn Tyr Ala Gln Glu Phe Gly Ile Lys Ile Ser Thr Ser Leu Ala Ser
            545                 550                 555                 560

Val Glu Ala Arg Ile Leu Pro Pro Trp Leu Lys Tyr His Glu Ser
                            565                 570                 575

Gly Arg Glu Gly Thr Cys Leu Pro Gln Val Gly Gln Trp Asn Met Met
                        580                 585                 590

Asn Lys Lys Met Ile Asn Gly Gly Thr Val Asn Asn Trp Ile Cys Ile
                    595                 600                 605

Asn Phe Ser Arg Gln Val Gln Asp Asn Leu Ala Arg Thr Phe Cys Gln
                    610                 615                 620

Glu Leu Ala Gln Met Cys Tyr Val Ser Gly Met Ala Phe Asn Pro Glu
            625                 630                 635                 640

Pro Val Leu Pro Pro Val Ser Ala Arg Pro Glu Gln Val Glu Lys Val
                            645                 650                 655

Leu Lys Thr Arg Tyr His Asp Ala Thr Ser Lys Leu Ser Gln Gly Lys
                        660                 665                 670

Glu Ile Asp Leu Leu Ile Val Ile Leu Pro Asp Asn Asn Gly Ser Leu
                    675                 680                 685

Tyr Gly Asp Leu Lys Arg Ile Cys Glu Thr Glu Leu Gly Ile Val Ser
                690                 695                 700

Gln Cys Cys Leu Thr Lys His Val Phe Lys Met Ser Lys Gln Tyr Met
            705                 710                 715                 720

Ala Asn Val Ala Leu Lys Ile Asn Val Lys Val Gly Gly Arg Asn Thr
                            725                 730                 735

Val Leu Val Asp Ala Leu Ser Arg Arg Ile Pro Leu Val Ser Asp Arg
                        740                 745                 750

Pro Thr Ile Ile Phe Gly Ala Asp Val Thr His Pro His Pro Gly Glu
                    755                 760                 765

Asp Ser Ser Pro Ser Ile Ala Ala Val Val Ala Ser Gln Asp Trp Pro
                    770                 775                 780

Glu Ile Thr Lys Tyr Ala Gly Leu Val Cys Ala Gln Ala His Arg Gln
            785                 790                 795                 800

Glu Leu Ile Gln Asp Leu Phe Lys Glu Trp Lys Asp Pro Gln Lys Gly
                            805                 810                 815
```

-continued

```
Val Val Thr Gly Gly Met Ile Lys Glu Leu Leu Ile Ala Phe Arg Arg
            820             825             830

Ser Thr Gly His Lys Pro Leu Arg Ile Ile Phe Tyr Arg Asp Gly Val
        835             840             845

Ser Glu Gly Gln Phe Tyr Gln Val Leu Leu Tyr Glu Leu Asp Ala Ile
850             855             860

Arg Lys Ala Cys Ala Ser Leu Glu Ala Gly Tyr Gln Pro Pro Val Thr
865             870             875             880

Phe Val Val Gln Lys Arg His His Thr Arg Leu Phe Ala Gln Asn
                885             890             895

His Asn Asp Arg His Ser Val Asp Arg Ser Gly Asn Ile Leu Pro Gly
            900             905             910

Thr Val Val Asp Ser Lys Ile Cys His Pro Thr Glu Phe Asp Phe Tyr
        915             920             925

Leu Cys Ser His Ala Gly Ile Gln Gly Thr Ser Arg Pro Ala His Tyr
    930             935             940

His Val Leu Trp Asp Glu Asn Asn Phe Thr Ala Asp Gly Leu Gln Ser
945             950             955             960

Leu Thr Asn Asn Leu Cys Tyr Thr Tyr Ala Arg Cys Thr Arg Ser Val
                965             970             975

Ser Ile Val Pro Pro Ala Tyr Tyr Ala His Leu Ala Ala Phe Arg Ala
            980             985             990

Arg Phe Tyr Met Glu Pro Glu Thr Ser Asp Ser Gly Ser Met Ala Ser
            995             1000            1005

Gly Ser Met Ala Arg Gly Gly Gly Met Ala Gly Arg Ser Thr Arg Gly
    1010            1015            1020

Pro Asn Val Asn Ala Ala Val Arg Pro Leu Pro Ala Leu Lys Glu Asn
1025            1030            1035            1040

Val Lys Arg Val Met Phe Tyr Cys
                1045
```